United States Patent
Morimoto et al.

(10) Patent No.: US 11,988,962 B2
(45) Date of Patent: May 21, 2024

(54) COLORED PHOTOSENSITIVE RESIN COMPOSITION

(71) Applicant: SUMITOMO CHEMICAL COMPANY, LIMITED, Tokyo (JP)

(72) Inventors: Jumpei Morimoto, Osaka (JP); Takakiyo Terakawa, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 949 days.

(21) Appl. No.: 16/965,430

(22) PCT Filed: Jan. 28, 2019

(86) PCT No.: PCT/JP2019/002633
§ 371 (c)(1),
(2) Date: Jul. 28, 2020

(87) PCT Pub. No.: WO2019/155923
PCT Pub. Date: Aug. 15, 2019

(65) Prior Publication Data
US 2021/0116806 A1 Apr. 22, 2021

(30) Foreign Application Priority Data

Feb. 6, 2018 (JP) ................. 2018-019555
Mar. 6, 2018 (JP) ................. 2018-039743

(51) Int. Cl.
| | |
|---|---|
| G03F 7/004 | (2006.01) |
| C09B 11/26 | (2006.01) |
| C09B 47/04 | (2006.01) |
| C09B 67/20 | (2006.01) |
| C09B 67/22 | (2006.01) |
| G02B 1/04 | (2006.01) |
| G03F 7/00 | (2006.01) |
| G03F 7/033 | (2006.01) |
| G02B 5/20 | (2006.01) |

(52) U.S. Cl.
CPC ............ *G03F 7/0045* (2013.01); *C09B 11/26* (2013.01); *C09B 47/04* (2013.01); *C09B 67/0033* (2013.01); *C09B 67/0064* (2013.01); *G02B 1/04* (2013.01); *G03F 7/0007* (2013.01); *G03F 7/033* (2013.01); *G02B 5/20* (2013.01)

(58) Field of Classification Search
CPC ..................................... C09B 11/26
See application file for complete search history.

(56) References Cited

U.S. PATENT DOCUMENTS

| | | |
|---|---|---|
| 2,922,690 A | 1/1960 | Mueller et al. |
| 4,074,967 A | 2/1978 | Fuchs et al. |

FOREIGN PATENT DOCUMENTS

| | | |
|---|---|---|
| CN | 107698536 A | 2/2018 |
| JP | S50-83577 A | 7/1975 |
| JP | 2005-049636 A | 2/2005 |
| JP | 2008-281636 A | 11/2008 |
| JP | 2011-059673 A | 3/2011 |
| JP | 2012-113218 A | 6/2012 |
| JP | 2012-220817 A | 11/2012 |
| JP | 2016-170324 A | 9/2016 |

(Continued)

OTHER PUBLICATIONS

Machine translation of PCT Written Opinion (no date).*
Machine translation of JP 2018-127596 (no date).*
Office Action issued in corresponding Japanese Patent Application No. JP2019-010998, dated Aug. 30, 2022.
International Searching Authority, "International Search Report," issued in connection with International Patent Application No. PCT/JP2019/002633, dated Mar. 26, 2019.
International Searching Authority, "Written Opinion," issued in connection with International Patent Application No. PCT/JP2019/002633, dated Mar. 26, 2019.

(Continued)

*Primary Examiner* — Amanda C. Walke
(74) *Attorney, Agent, or Firm* — Foley & Lardner LLP

(57) ABSTRACT

An object of the present invention is to provide a colored photosensitive resin composition capable of forming a color filter having a higher brightness than that of the color filter formed from the conventionally known colored photosensitive resin composition.
The colored photosensitive resin composition according to the present invention comprises a colorant, a resin, a polymerizable compound, and a polymerization initiator, the colorant comprising a compound represented by formula (1) and an α-type and/or β-type copper phthalocyanine pigment,

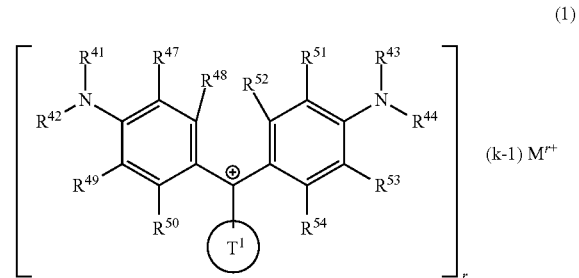

(1)

wherein $M^{r+}$ represents an r-valent metal ion; k represents the sum of the number of $-SO_3^-$ and the number of $-SO_2-N^--SO_2-R^f$ in the compound represented by formula (1); r represents an integer of 1 or more; $R^f$ represents a fluoroalkyl group having 1 to 12 carbon atoms; and the compound represented by formula (1) has at least one $-SO_3^-$ or $-SO_2-N^--SO_2-R^f$.

5 Claims, No Drawings

(56) References Cited

FOREIGN PATENT DOCUMENTS

| JP | 2018127596 A | * | 8/2018 | ........... C07D 277/38 |
|----|---|---|---|---|
| JP | 2018194747 A | * | 12/2018 | |
| KR | 20180016960 A | | 2/2018 | |
| TW | 201612635 A | | 4/2016 | |
| TW | I597330 B | | 9/2017 | |
| WO | WO-2014/155842 A1 | | 10/2014 | |
| WO | WO-2016/021525 A1 | | 2/2016 | |
| WO | WO-2021005997 A1 | * | 1/2021 | |

OTHER PUBLICATIONS

Office Action issued in corresponding Taiwanese Patent Application No. 108103657 dated Jun. 28, 2022.

\* cited by examiner

COLORED PHOTOSENSITIVE RESIN COMPOSITION

CROSS-REFERENCE TO RELATED APPLICATIONS

The present application claims priority under 37 U.S.C. § 371 to International Patent Application No. PCT/JP2019/002633, filed Jan. 28, 2019, which claims priority to and the benefit of Japanese Patent Application Nos. 2018-019555, filed on Feb. 6, 2018, and 2018-039743, filed on Mar. 6, 2018. The contents of these applications are hereby incorporated by reference in their entireties.

TECHNICAL FIELD

The present invention relates to a colored photosensitive resin composition.

BACKGROUND ART

A color filter used for display devices such as a liquid crystal display device, an electroluminescence display device, and a plasma display, and solid-state image sensors such as a CCD and a CMOS sensor is produced from a colored photosensitive resin composition. As such a colored photosensitive resin composition, a composition containing C.I. Pigment blue 15:6 has been known (Patent Literature 1).

CITATION LIST

Patent Literature

Patent Literature 1: International Publication No. WO 2014/155842

SUMMARY OF INVENTION

Technical Problem

An object of the present invention is to provide a colored photosensitive resin composition capable of forming a color filter having a higher brightness than that of the color filter formed from the conventionally known colored photosensitive resin composition.

Solution to Problem

The gist of the present invention is as follows.

[1] A colored photosensitive resin composition comprising a colorant, a resin, a polymerizable compound, and a polymerization initiator, the colorant comprising a compound represented by formula (1) and an α-type and/or β-type copper phthalocyanine pigment:

[Formula 1]

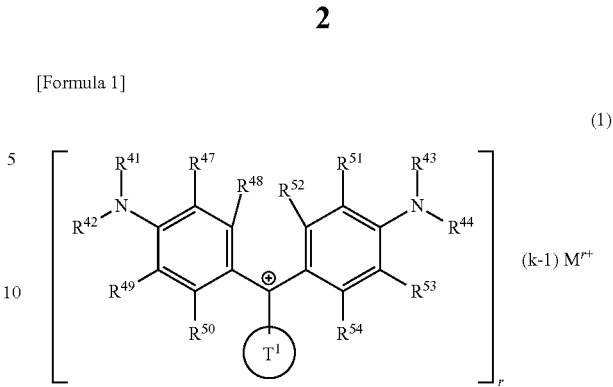

wherein $R^{41}$ to $R^{44}$ each independently represent a hydrogen atom, a saturated hydrocarbon group having 1 to 20 carbon atoms, an aromatic hydrocarbon group having 6 to 20 carbon atoms and optionally having a substituent, or an aralkyl group having 7 to 30 carbon atoms and optionally having a substituent; the substituent which is optionally contained in the aromatic hydrocarbon group and the aralkyl group may be $-SO_3^-$ or $-SO_2-N^--SO_2-R^f$; a hydrogen atom contained in the saturated hydrocarbon group is optionally replaced with a substituted or unsubstituted amino group or a halogen atom; when the number of carbon atoms of the saturated hydrocarbon group is 2 to 20, $-CH_2-$ contained in the saturated hydrocarbon group is optionally replaced with at least one of $-O-$ and $-CO-$, provided that in the saturated hydrocarbon group having 2 to 20 carbon atoms, $-CH_2-$ and $-CH_2-$ adjacent to each other are not simultaneously replaced with $-O-$, and terminal $-CH_2-$ is not replaced with $-O-$ or $-CO-$; $R^{41}$ and $R^{42}$ are optionally bonded to each other to form a ring together with a nitrogen atom to which they are attached; $R^{43}$ and $R^{44}$ are optionally bonded to each other to form a ring together with a nitrogen atom to which they are attached;

$R^{47}$ to $R^{54}$ each independently represent a hydrogen atom, a halogen atom, a nitro group, a hydroxy group, $-SO_3^-$, $-SO_2-N^--SO_2-R^f$, or a saturated hydrocarbon group having 1 to 20 carbon atoms; $-CH_2-$ constituting the saturated hydrocarbon group is optionally replaced with at least one of $-O-$ and $-CO-$; $R^{48}$ and $R^{52}$ are optionally bonded to each other to form $-NH-$, $-S-$, or $-SO_2^-$, provided that in the saturated hydrocarbon group, $-CH_2-$ and $-CH_2-$ adjacent to each other are not simultaneously replaced with $-O-$, and terminal $-CH_2-$ is not replaced with $-O-$ or $-CO-$;

a ring $T^1$ represents an aromatic heterocycle having 3 to 10 carbon atoms; the aromatic heterocycle optionally has a saturated hydrocarbon group having 1 to 20 carbon atoms, a substituted or unsubstituted amino group, or an aromatic hydrocarbon group having 6 to 20 carbon atoms and optionally having a substituent; the substituent which is optionally contained in the aromatic hydrocarbon group may be $-SO_3^-$ or $-SO_2-N^--SO_2-R^f$;

$M^{r+}$ represents an r-valent metal ion;

k represents the sum of the number of $-SO_3^-$ and the number of $-SO_2-N^--SO_2-R^f$ in the compound represented by formula (1);

r represents an integer of 1 or more; $R^f$ represents a fluoroalkyl group having 1 to 12 carbon atoms; and the compound represented by formula (1) has at least one —$SO_3^-$ or —$SO_2$—$N^-$—$SO_2$—$R^f$.

[2] The colored photosensitive resin composition according to [1], wherein a content rate of the copper phthalocyanine pigment is 10% by mass or more and 80% by mass or less in 100% by mass of the colorant.

[3] A color filter formed from the colored photosensitive resin composition according to [1] or [2].

[4] A display device comprising the color filter according to [3].

Advantageous Effects of Invention

According to a colored photosensitive resin composition of the present invention, a color filter having a high brightness can be formed.

DESCRIPTION OF EMBODIMENTS

A colored photosensitive resin composition of the present invention contains a colorant (hereinafter, sometimes referred to as colorant (A)), a resin (hereinafter, sometimes referred to as resin (B)), a polymerizable compound (hereinafter, sometimes referred to as polymerizable compound (C)), and a polymerization initiator (hereinafter, sometimes referred to as polymerization initiator (D)).

The colorant contains a compound represented by formula (1) (hereinafter, sometimes referred to as compound (1)) and an α-type and/or β-type copper phthalocyanine pigment.

It is preferable that the colored photosensitive resin composition of the present invention further contains a solvent (hereinafter, sometimes referred to as solvent (E)).

The colored photosensitive resin composition of the present invention may contain a leveling agent (hereinafter, sometimes referred to as leveling agent (F)).

Herein, compounds exemplified as components may be used singly or in combinations of a plurality thereof unless otherwise noted.

<Colorant (A)>

The colorant (A) contains a compound (1) and an α-type and/or β-type copper phthalocyanine pigment. The compound of the present invention includes tautomers of the compound and salts of the compound and the tautomers:

[Formula 2]

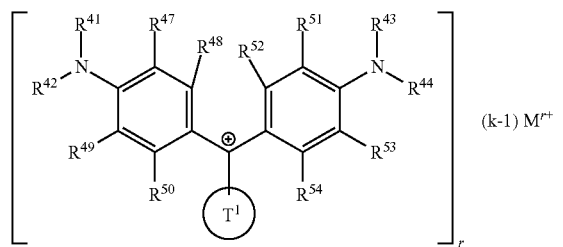

wherein $R^{41}$ to $R^{44}$ each independently represent a hydrogen atom, a saturated hydrocarbon group having 1 to 20 carbon atoms, an aromatic hydrocarbon group having 6 to 20 carbon atoms and optionally having a substituent, or an aralkyl group having 7 to 30 carbon atoms and optionally having a substituent; the substituent which is optionally contained in the aromatic hydrocarbon group and the aralkyl group may be —$SO_3^-$ or —$SO_2$—$N^-$—$SO_2$—$R^f$; a hydrogen atom contained in the saturated hydrocarbon group is optionally replaced with a substituted or unsubstituted amino group or a halogen atom; when the number of carbon atoms of the saturated hydrocarbon group is 2 to 20, —$CH_2$— contained in the saturated hydrocarbon group is optionally replaced with at least one of —O— and —CO—, provided that in the saturated hydrocarbon group having 2 to 20 carbon atoms, —$CH_2$— and —$CH_2$— adjacent to each other are not simultaneously replaced with —O—, and terminal —$CH_2$— is not replaced with —O— or —CO—; $R^{41}$ and $R^{42}$ are optionally bonded to each other to form a ring together with a nitrogen atom to which they are attached; $R^{43}$ and $R^{44}$ are optionally bonded to each other to form a ring together with a nitrogen atom to which they are attached;

$R^{47}$ to $R^{54}$ each independently represent a hydrogen atom, a halogen atom, a nitro group, a hydroxy group, —$SO_3^-$, —$SO_2$—$N^-$—$SO_2$—$R^f$, or a saturated hydrocarbon group having 1 to 20 carbon atoms; —$CH_2$— constituting the saturated hydrocarbon group is optionally replaced with at least one of —O— and —CO—; $R^{48}$ and $R^{52}$ are optionally bonded to each other to form —NH—, —S—, or —$SO_2^-$, provided that in the saturated hydrocarbon group, —$CH_2$— and —$CH_2$— adjacent to each other are not simultaneously replaced with —O—, and terminal —$CH_2$— is not replaced with —O— or —CO—;

a ring $T^1$ represents an aromatic heterocycle having 3 to 10 carbon atoms; the aromatic heterocycle optionally has a saturated hydrocarbon group having 1 to 20 carbon atoms, a substituted or unsubstituted amino group, or an aromatic hydrocarbon group having 6 to 20 carbon atoms and optionally having a substituent; the substituent which is optionally contained in the aromatic hydrocarbon group may be —$SO_3^-$ or —$SO_2$—$N^-$—$SO_2$—$R^f$;

$M^{r+}$ represents an r-valent metal ion;

k represents the sum of the number of —$SO_3^-$ and the number of —$SO_2$—$N^-$—$SO_2$—$R^f$ in the compound (1);

r represents an integer of 1 or more;

$R^f$ represents a fluoroalkyl group having 112 carbon atoms; and the compound (1) has at least one —$SO_3^-$ or —$SO_2$—$N^-$—$SO_2$—$R^f$.

The aromatic heterocycle represented by the ring $T^1$ may be a monocyclic ring or a fused ring. The aromatic heterocycle represented by the ring $T^1$ has preferably 3 to 10 carbon atoms, and more preferably 3 to 8 carbon atoms. The aromatic heterocycle is preferably a 5- to 10-membered ring, and more preferably a 5- to 9-membered ring. Examples of the aromatic heterocycle of the monocyclic ring include a 5-membered ring containing a nitrogen atom such as a pyrrole ring, an oxazole ring, a pyrazole ring, an imidazole ring, or a thiazole ring; a 5-membered ring containing no nitrogen atom such as a furan ring or a thiophen ring; and a 6-membered ring containing a nitrogen atom such as a pyridine ring, a pyrimidine ring, a pyridazine ring, or a pyrazine ring. Examples of the aromatic heterocycle of the fused ring include a fused ring containing a nitrogen atom such as an indole ring, a benzimidazole ring, a benzothiazole ring, or a quinoline ring; and a fused ring containing no nitrogen atom such as a benzofuran ring.

Examples of the substituent which is optionally contained in the aromatic heterocycle of the ring $T^1$ include a halogen atom, a cyano group, a saturated hydrocarbon group having 1 to 20 carbon atoms and optionally having a substituent, a substituted or unsubstituted amino group, or an aromatic hydrocarbon group having 6 to 20 carbon atoms and optionally having a substituent. Preferably, examples of the substituent include a saturated hydrocarbon group having 1 to 20 carbon atoms and optionally having a substituent, a substituted or unsubstituted amino group, or an aromatic hydrocarbon group having 6 to 20 carbon atoms and optionally having a substituent. More preferably, examples of the substituent include a saturated hydrocarbon group having 1 to 10 carbon atoms and optionally having a substituent, a substituted or unsubstituted amino group, or an aromatic hydrocarbon group having 6 to 10 carbon atoms and optionally having a substituent. The ring $T^1$ preferably has an amino group and optionally having a substituent. Preferably, examples of the substituent which is optionally contained in the amino group include a saturated hydrocarbon group having 1 to 20 carbon atoms, an aromatic hydrocarbon group having 6 to 10 carbon atoms and optionally having a substituent, and an aralkyl group having 7 to 30 carbon atoms and optionally having a substituent.

Among these, the aromatic heterocycle of the ring $T^1$ is preferably an aromatic heterocycle containing a nitrogen atom, and more preferably a 5-membered aromatic heterocycle containing a nitrogen atom.

The ring $T^1$ is preferably a ring represented by formula (t1):

[Formula 3]

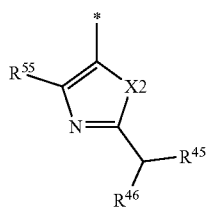

(t1)

wherein
X2 represents —O—, —N($R^{57}$)—, or —S—;
$R^{57}$ represents a hydrogen atom or an alkyl group having 1 to 10 carbon atoms;
$R^{45}$ and $R^{46}$ each independently represent a hydrogen atom, a saturated hydrocarbon group having 1 to 20 carbon atoms and optionally having a substituent, an aromatic hydrocarbon group having 6 to 20 carbon atoms and optionally having a substituent, or an aralkyl group having 7 to 30 carbon atoms and optionally having a substituent;
$R^{55}$ represents a hydrogen atom, a saturated hydrocarbon group having 1 to 20 carbon atoms, or an aromatic hydrocarbon group having 6 to 20 carbon atoms and optionally having a substituent;
when the number of carbon atoms of the saturated hydrocarbon group is 2 to 20 in $R^{45}$, $R^{46}$, and $R^{55}$, —CH$_2$— contained in the saturated hydrocarbon group is optionally replaced with at least one of —O— and —CO—, provided that in the saturated hydrocarbon group having 2 to 20 carbon atoms, —CH$_2$— and —CH$_2$— adjacent to each other are not simultaneously replaced with —O—, and terminal —CH$_2$— is not replaced with —O— or —CO—;
$R^{45}$ and $R^{46}$ are optionally bonded to each other to form a ring together with a nitrogen atom to which they are attached; and
* represents a point of attachment to with a carbocation.
The ring $T^1$ is also preferably a ring represented by formula (t2):

[Formula 4]

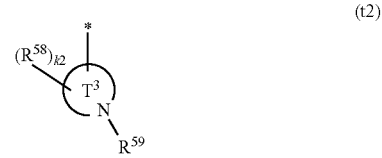

(t2)

wherein
a ring $T^3$ represents an aromatic heterocycle having 3 to 10 carbon atoms and having a nitrogen atom;
$R^{58}$ represents a saturated hydrocarbon group having 1 to 20 carbon atoms, an aromatic hydrocarbon group having 6 to 20 carbon atoms and optionally having a substituent, —SO$_3^-$, or —SO$_2$—N$^-$—SO$_2$—R$^f$;
$R^{59}$ represents a hydrogen atom, a saturated hydrocarbon group having 1 to 20 carbon atoms and optionally having a substituent, an aromatic hydrocarbon group having 6 to 20 carbon atoms and optionally having a substituent, or an aralkyl group having 7 to 30 carbon atoms and optionally having a substituent;
k2 represents 0 or 1; and
* represents a point of attachment to a carbocation.
The ring represented by formula (t2) is also more preferably a ring represented by formula (t2-1):

[Formula 5]

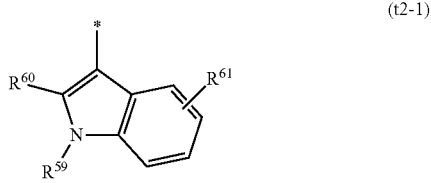

(t2-1)

wherein
$R^{60}$ represents a hydrogen atom, a saturated hydrocarbon group having 1 to 20 carbon atoms, or an aromatic hydrocarbon group having 6 to 20 carbon atoms and optionally having a substituent;
$R^{61}$ represents a hydrogen atom, —SO$_3^-$, or —SO$_2$—N$^-$—SO$_2$—R$^f$;
$R^{59}$ is the same as above; and
* represents a chemical hand with a carbocation.
The saturated hydrocarbon group having 1 to 20 carbon atoms represented by $R^{41}$ to $R^{55}$ and $R^{58}$ to $R^{60}$ and the saturated hydrocarbon group having 1 to 20 carbon atoms which may be contained in an amino group which may substitute the ring $T^1$ may be either linear, branched, or cyclic. Examples of the linear or branched saturated hydrocarbon group include linear alkyl groups such as a methyl group, an ethyl group, a propyl group, a butyl group, a pentyl group, a hexyl group, a heptyl group, an octyl group, a nonyl group, a decyl group, a dodecyl group, a hexadecyl group, and an icosyl group; and branched alkyl groups such as an isopropyl group, an isobutyl group, an isopentyl group, a neopentyl group, and a 2-ethylhexyl group. The number of carbon atoms of the saturated hydrocarbon group is preferably 1 to 10, more preferably 1 to 8, and still more preferably 1 to 6.

The cyclic saturated hydrocarbon group represented by $R^{41}$ to $R^{55}$ and $R^{58}$ to $R^{60}$ and the cyclic saturated hydrocarbon group which may be contained in an amino group which may be contained in the ring $T^1$ may be either monocyclic or polycyclic. Examples of the cyclic saturated hydrocarbon group include alicyclic saturated hydrocarbon groups such as a cyclopropyl group, a cyclobutyl group, a cyclopentyl group, a cyclohexyl group, and an adamantyl group. The number of carbon atoms of the cyclic saturated hydrocarbon group is preferably 3 to 10, and more preferably 6 to 10.

Examples of the saturated hydrocarbon group represented by $R^{41}$ to $R^{55}$ and $R^{58}$ to $R^{60}$ and the saturated hydrocarbon group which may be contained in an amino group which may be contained in the ring $T^1$ include a methyl group, an ethyl group, an isopropyl group, a propyl group, a butyl group, a pentyl group, a hexyl group, an isobutyl group, a 2-ethylhexyl group, a cyclohexyl group, and an adamantyl group.

The saturated hydrocarbon group represented by $R^{41}$ to $R^{55}$ and $R^{58}$ to $R^{60}$ and the saturated hydrocarbon group which may be contained in an amino group which may be contained in the ring $T^1$ may have a substituted or unsubstituted amino group or a halogen atom as a substituent. Examples of the substituted amino group include alkylamino groups such as a dimethylamino group and a diethylamino group. Examples of the halogen atom include fluoride, chlorine, bromine, and iodine. When the halogen atom is the fluorine atom, the saturated hydrocarbon group having the fluorine atom as a substituent is preferably a perfluoroalkyl group such as a trifluoromethyl group, a perfluoroethyl group, or a perfluoropropyl group.

Examples of the alkyl group having 1 to 10 carbon atoms represented by $R^{57}$ include groups having 1 to 10 carbon atoms among the linear or branched saturated hydrocarbon groups exemplified as the saturated hydrocarbon group represented by $R^{41}$.

When the number of carbon atoms of the saturated hydrocarbon group represented by $R^{41}$ to $R^{46}$ and $R^{55}$ is 2 to 20, $—CH_2—$ contained in the saturated hydrocarbon group is optionally replaced with at least one of $—O—$ and $—CO—$. However, in the saturated hydrocarbon group having 2 to 20 carbon atoms, $—CH_2—$ and $—CH_2—$ adjacent to each other are not simultaneously replaced with $—O—$, and terminal $—CH_2—$ is not replaced with $—O—$ or $—CO—$. In this case, the saturated hydrocarbon group is preferably a linear or branched saturated hydrocarbon group (that is, linear or branched alkyl group), and more preferably a linear saturated hydrocarbon group (that is, linear alkyl group). The number of carbon atoms of the saturated hydrocarbon group in which $—CH_2—$ is optionally replaced with at least one of $—O—$ and $—CO—$ is preferably 2 to 10, and more preferably 2 to 8. When $—CH_2—$ is replaced with at least one of $—O—$ and $—CO—$, the number of carbon atoms between a terminal and $—O—$ or $—CO—$, or between $—O—$ or $—CO—$ and $—O—$ or $—CO—$ is 1 or more, preferably 1 to 5, more preferably 2 and 3, and still more preferably 2.

The number of carbon atoms of the aromatic hydrocarbon group optionally having a substituent and is represented by $R^{41}$ to $R^{46}$, $R^{55}$, and $R^{58}$ to $R^{60}$ and the aromatic hydrocarbon group which may be contained in an amino group which may be contained in the ring $T^1$ (wherein the aromatic hydrocarbon group optionally has a substituent) is preferably 6 to 20, more preferably 6 to 15, and still more preferably 6 to 12. Examples of the aromatic hydrocarbon group include a phenyl group, a tolyl group, a xylyl group, a naphthyl group, an anthryl group, a phenanthryl group, a biphenyl group, and a terphenyl group. Preferably, the aromatic hydrocarbon group is a phenyl group, a naphthyl group, a tolyl group, and a xylyl group, and particularly preferably a phenyl group. The aromatic hydrocarbon group may have one or two or more substituents. Examples of the substituent include a halogen atom such as a fluorine atom, a chlorine atom, an iodine atom, or a bromine atom; an alkoxy group having 1 to 6 carbon atoms such as a methoxy group or an ethoxy group; a hydroxy group; a sulfamoyl group; an alkylsulfonyl group having 1 to 6 carbon atoms such as a methylsulfonyl group; an alkoxycarbonyl group having 1 to 6 carbon atoms such as a methoxy carbonyl group or an ethoxycarbonyl group; $—SO_3^-$; and $—SO_2—N^-—SO_2—R^f$. The substituent may be $—SO_3^-$ or $—SO_2—N^-—SO_2—R^f$. However, it is preferable that $—SO_3^-$ and $—SO_2—N^-—SO_2—R^f$ are directly bonded to the aromatic hydrocarbon ring of the aromatic hydrocarbon group, that is, substitute the hydrogen atom bonded to the aromatic hydrocarbon ring. The substituent in the aromatic hydrocarbon group represented by $R^{55}$ is preferably a halogen atom and a haloalkyl group having 1 to 6 carbon atoms.

Specific examples of the aromatic hydrocarbon group optionally having a substituent include a group represented by the following formula. In the following formula, * represents a chemical hand with a nitrogen atom or a carbon atom.

[Formula 6]

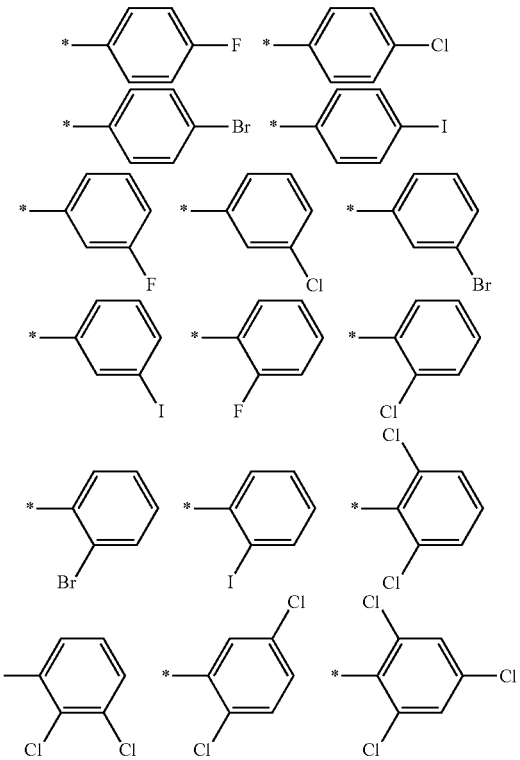

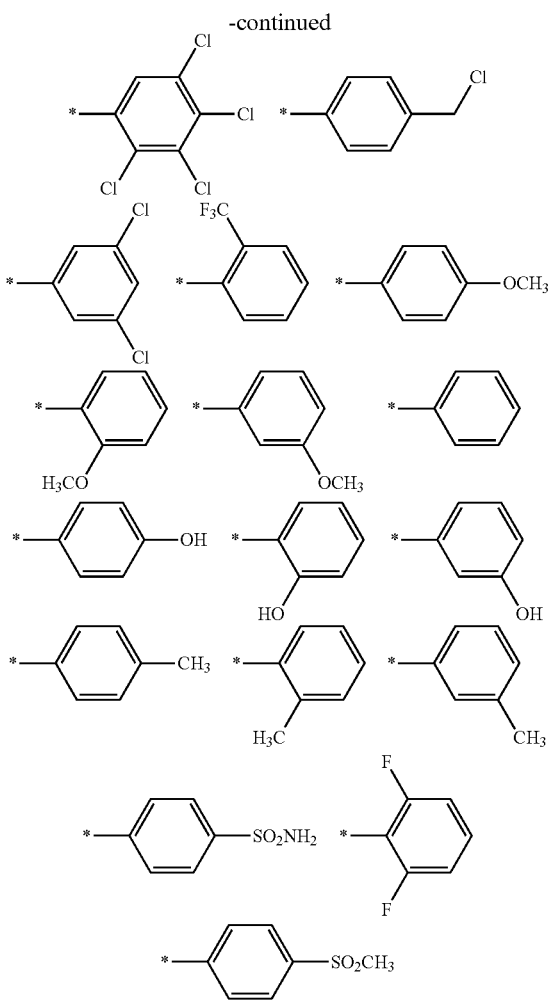

[Formula 7]

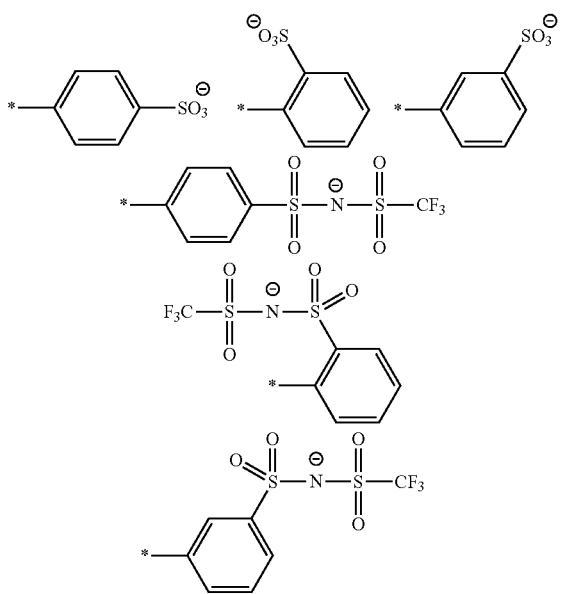

Examples of the aralkyl group optionally having a substituent and is represented by $R^{41}$ to $R^{46}$ and $R^{59}$ and the aralkyl group which may be contained in an amino group which may be contained in the ring $T^1$ (wherein the aralkyl group optionally has a substituent) include a group in which an alkanediyl group having 1 to 10 carbon atoms (preferably, 1 to 5 carbon atoms) such as a methylene group, an ethylene group, or a propylene group is bonded to each of the groups described as the above aromatic hydrocarbon group. The number of carbon atoms of the aralkyl group is preferably 7 to 30, more preferably 7 to 20, and still more preferably 7 to 17.

Examples of the ring which $R^{41}$ and $R^{42}$ are bonded to each other to form together with a nitrogen atom to which they are attached, the ring which $R^{43}$ and $R^{44}$ are bonded to each other to form together with a nitrogen atom to which they are attached, and the ring which $R^{45}$ and $R^{46}$ are bonded to each other to form together with a nitrogen atom to which they are attached include nitrogen-containing non-aromatic 4- to 7-membered rings such as a pyrrolidine ring, a morpholine ring, a piperidine ring, and a piperazine ring. Preferably, examples thereof include 4- to 7-membered rings having only one nitrogen atom as a hetero atom such as a pyrrolidine ring and a piperidine ring.

$R^{58}$ is preferably a saturated hydrocarbon group having 1 to 20 carbon atoms or an aromatic hydrocarbon group having 6 to 20 carbon atoms and optionally having a substituent.

Among these, it is preferable that $R^{41}$ to $R^{44}$, $R^{55}$, and $R^{58}$ to $R^{60}$ are a saturated hydrocarbon group having 1 to 20 carbon atoms or an aromatic hydrocarbon group optionally having a substituent. It is more preferable that $R^{41}$ to $R^{44}$, $R^{55}$, and $R^{58}$ to $R^{60}$ are each independently a saturated hydrocarbon group having 1 to 8 carbon atoms or a group represented by the following formula. In particular, it is preferable that $R^{41}$ and $R^{43}$ are each independently a saturated hydrocarbon group having 1 to 20 carbon atoms. It is more preferable that $R^{41}$ and $R^{43}$ are each independently a saturated hydrocarbon group having 1 to 10 carbon atoms. It is preferable that $R^{42}$ and $R^{44}$ are each independently an aromatic hydrocarbon group optionally having a substituent. It is more preferable that $R^{42}$ and $R^{44}$ are each independently a phenyl group optionally having a substituent. It is more preferable that $R^{55}$ is an aromatic hydrocarbon group optionally having a substituent.

$R^{55}$ and $R^{58}$ to $R^{60}$ are still more preferably a group represented by the following formula. In the following formula, * represents a point of attachment to a nitrogen atom or a carbon atom.

[Formula 8]

-continued

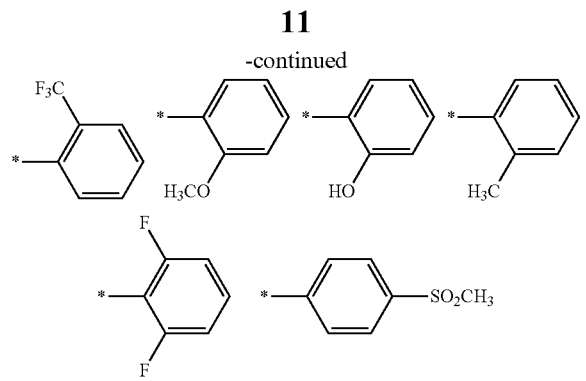

[Formula 9]

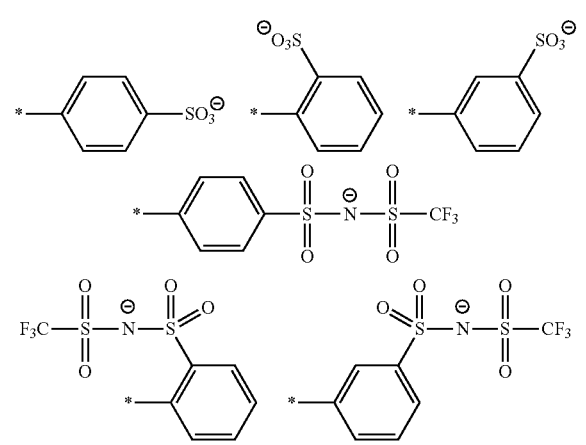

It is preferable that $R^{45}$ and $R^{46}$ are each independently a saturated hydrocarbon group having 1 to 20 carbon atoms, a group in which —$CH_2$— constituting an alkyl group having 2 to 20 carbon atoms is substituted at least one of —O— and —CO—, or an aromatic hydrocarbon group optionally having a substituent, or $R^{45}$ and $R^{46}$ are bonded to each other to form a ring together with a nitrogen atom to which they are attached. It is more preferable that $R^{45}$ and $R^{46}$ are each independently a saturated hydrocarbon group having 1 to 8 carbon atoms, an alkoxyalkyl group, or a group represented by the following formula, or $R^{45}$ and $R^{46}$ are bonded to each other to form a 4- to 7-membered ring having only one nitrogen atom as a hetero atom. It is still more preferable that $R^{45}$ and $R^{46}$ are each independently a saturated hydrocarbon group having 1 to 8 carbon atoms, an alkoxyalkyl group, or a group represented by the following formula. In the following formula, * represents a point of attachment to a nitrogen atom.

[Formula 10]

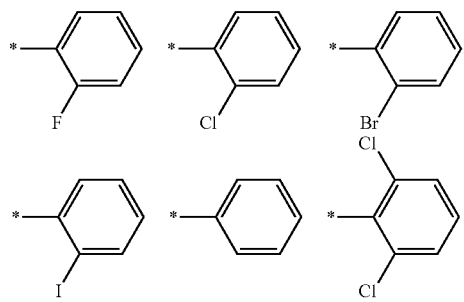

-continued

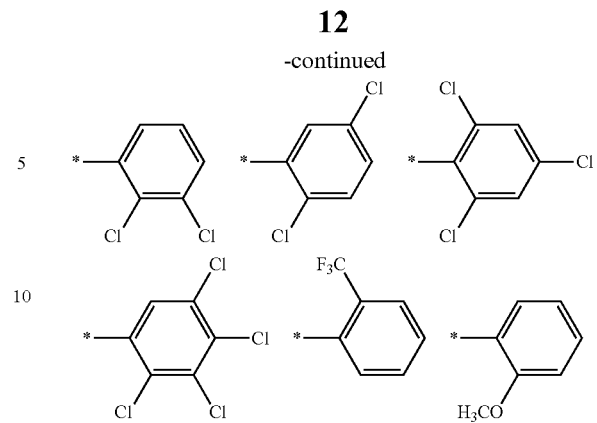

[Formula 11]

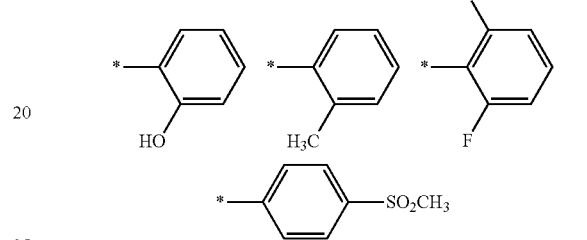

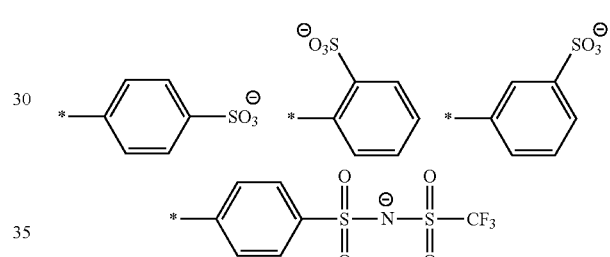

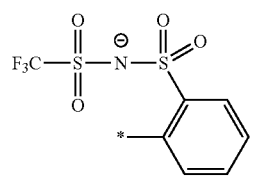

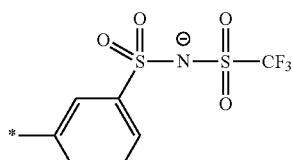

Among these, it is preferable that $R^{45}$ is a saturated hydrocarbon group having 1 to 4 carbon atoms, and $R^{46}$ is preferably an o-tolyl group.

Examples of the alkyl group having 1 to 8 carbon atoms represented by $R^{47}$ to $R^{54}$ include a group having 1 to 8 carbon atoms among the linear or branched saturated hydrocarbon groups exemplified as the saturated hydrocarbon group represented by $R^{41}$. Examples of the group in which —$CH_2$— constituting the alkyl group having 2 to 8 carbon atoms represented by $R^{47}$ to $R^{54}$ is replaced with at least one of —O— and —CO— (provided that in the alkyl group, —$CH_2$— and —$CH_2$— adjacent to each other are not simultaneously replaced with —O—, and terminal —$CH_2^-$ is not replaced with —O— or —CO—) include a group having 8 or less carbon atoms among the groups in which —$CH_2^-$ constituting the alkyl group having 2 to 20 carbon atoms represented by $R^{41}$ to $R^{46}$ is replaced with at least one of —O— and —CO—.

It is preferable that $R^{47}$ to $R^{54}$ are each independently a hydrogen atom, a halogen atom, or an alkyl group having 1 to 8 carbon atoms. It is more preferable that $R^{47}$ to $R^{54}$ are each independently a hydrogen atom, a methyl group, a fluorine atom, or a chlorine atom. It is still more preferable that $R^{47}$ to $R^{54}$ are each independently a hydrogen atom.

$R^{57}$ is preferably a hydrogen atom or an alkyl group having 1 to 5 carbon atom.

$R^{61}$ is preferably a hydrogen atom.

Examples of the r-valent metal ion represented by $M^{r+}$ include alkali metal ions such as a lithium ion, a sodium ion, and a potassium ion; alkaline-earth metal ions such as a beryllium ion, a magnesium ion, a calcium ion, a strontium ion, and a barium ion; transition metal ions such as a titanium ion, a zirconium ion, a chromium ion, a manganese ion, a ferric iron, a cobalt ion, a nickel ion, and a copper ion; and typical metal ions such as a zinc ion, a cadmium ion, an aluminum ion, an indium ion, a tin ion, a lead ion, and a bismuth ion. r is preferably 1 or more, and more preferably 2 or more. r is preferably 5 or less, more preferably 4 or less, and still more preferably 3 or less.

$M^{r+}$ is more preferably an alkaline-earth metal ion, a typical metal ion and the like, still more preferably an alkaline-earth metal ion and a zinc ion, and yet still more preferably an alkaline-earth metal ion.

In formula (1), the number of $M^{r+}$ is less by 1 than the sum (k) of the number of —$SO_3^-$ and the number of —$SO_2$—$N^-$—$SO_2$—$R^f$ in the compound (1). For this reason, the compound (1) is a zero-valent compound, i.e., an electrically neutral compound.

Examples of the fluoroalkyl group having 1 to 12 carbon atoms represented by $R^f$ include a monofluoromethyl group, a difluoromethyl group, a perfluoromethyl group, a monofluoroethyl group, a difluoroethyl group, a trifluoroethyl group, a tetrafluoroethyl group, a perfluoroethyl group, a monofluoropropyl group, a difluoropropyl group, a trifluoropropyl group, a tetrafluoropropyl group, a pentafluoropropyl group, a hexafluoropropyl group, a perfluoropropyl group, a monofluorobutyl group, a difluorobutyl group, a trifluorobutyl group, a tetrafluorobutyl group, a pentafluorobutyl group, a hexafluorobutyl group, a heptafluorobutyl group, an octafluorobutyl group, and a perfluorobutyl group. Among these, the fluoroalkyl group represented by $R^f$ is preferably a perfluoroalkyl group. The number of carbon atoms of the fluoroalkyl group represented by $R^f$ is preferably 1 to 10, more preferably 1 to 5, and still more preferably 1 to 3.

In formula (1), $R^{41}$ to $R^{44}$, $R^{47}$ to $R^{54}$, and the ring $T^1$ have at least one —$SO_3^-$ or —$SO_2$—$N^-$—$SO_2$—$R^f$. The sum (k) of the number of —$SO_3^-$ and the number of —$SO_2$—$N^-$—$SO_2$—$R^f$ in $R^{41}$ to $R^{44}$, $R^{47}$ to $R^{54}$, and the ring $T^1$ is 1 or more, preferably 1 to 7, more preferably 2 to 7, still more preferably 2 to 4, yet still more preferably 2 or 3, and particularly preferably 2.

—$SO_3^-$ or —$SO_2$—$N^-$—$SO_2$—$R^f$ preferably satisfies at least one or more conditions selected from the following (Ia) to (Id), and more preferably satisfies at least one or more conditions selected from (Ia) and (Ib):

(Ia) —$SO_3^-$ or —$SO_2$—$N^-$—$SO_2$—$R^f$ is contained as any of $R^{47}$ to $R^{54}$;

(Ib) —$SO_3^-$ or —$SO_2$—$N^-$—$SO_2$—$R^f$ is bonded to any of the aromatic hydrocarbon groups having 6 to 20 carbon atoms which optionally have a substituent and are represented by $R^{41}$ to $R^{44}$;

(Ic) —$SO_3^-$ or —$SO_2$—$N^-$—$SO_2$—$R^f$ is bonded to any of the aralkyl groups having 7 to 30 carbon atoms which optionally have a substituent and are represented by $R^{41}$ to $R^{44}$; and (Id) —$SO_3^-$ or —$SO_2$—$N^-$—$SO_2$—$R^f$ is bonded to any of the aromatic hydrocarbon groups having 6 to 20 carbon atoms which substitute the hydrogen atoms of the aromatic heterocycle represented by $T^1$.

However, it is preferable that, when —$SO_3^-$ or —$SO_2$—$N^-$—$SO_2$—$R^f$ is bonded to an aromatic hydrocarbon group or an aralkyl group, —$SO_3^-$ or —$SO_2$—$N^-$—$SO_2$—$R^f$ is directly bonded to the aromatic hydrocarbon ring of the aromatic hydrocarbon group or aralkyl group. That is, —$SO_3^-$ or —$SO_2$—$N^-$—$SO_2$—$R^f$ preferably substitutes the hydrogen atom bonded to the aromatic hydrocarbon ring.

—$SO_3^-$ or —$SO_2$—$N^-$—$SO_2$—$R^f$ is preferably bonded to a para position with respect to a bonding position with a nitrogen atom in the aromatic hydrocarbon ring (for example, benzene ring) in the aromatic hydrocarbon group having 6 to 20 carbon atoms and optionally having a substituent and represents $R^{41}$ to $R^{44}$ or the aralkyl group having 7 to 30 carbon atoms and optionally having a substituent and represents $R^{41}$ to $R^{44}$.

When a plurality of —$SO_3^-$ or —$SO_2$—$N^-$—$SO_2$—$R^f$ are contained in the compound (1), the plurality of —$SO_3^-$ or —$SO_2$—$N^-$—$SO_2$—$R^f$ may be bonded to the same aromatic hydrocarbon ring, but these are preferably bonded to different aromatic hydrocarbon rings.

The compound (1) preferably has no ethylenically unsaturated bond.

In the compound (1), it is preferable that $R^{41}$ and $R^{43}$ are each independently a saturated hydrocarbon group having 1 to 10 carbon atoms (a hydrogen atom contained in the saturated hydrocarbon group is optionally replaced with a substituted or unsubstituted amino group or a halogen atom; when the number of carbon atoms of the saturated hydrocarbon group is 2 to 20, —$CH_2$— contained in the saturated hydrocarbon group is optionally replaced with at least one of —O— and —CO—); $R^{42}$ and $R^{44}$ are each independently a phenyl group optionally having a substituent (the substituent which is optionally contained in the phenyl group may be —$SO_3^-$ or —$SO_2^-N^-$—$SO_2$—$R^f$); $R^{47}$ to $R^{54}$ are a hydrogen atom; the ring $T^1$ is a nitrogen atom-containing 5-membered ring (the 5-membered ring may have a saturated hydrocarbon group having 1 to 10 carbon atoms, a substituted or unsubstituted amino group, or an aromatic hydrocarbon group having 6 to 10 carbon atoms and optionally having a substituent; and the substituent which is optionally contained in the aromatic hydrocarbon group may be —$SO_3^-$ or —$SO_2$—$N^-$—$SO_2$—$R^f$) or a compound represented by formula (1-1) (hereinafter, sometimes referred to as "compound (1-1)"):

[Formula 12]

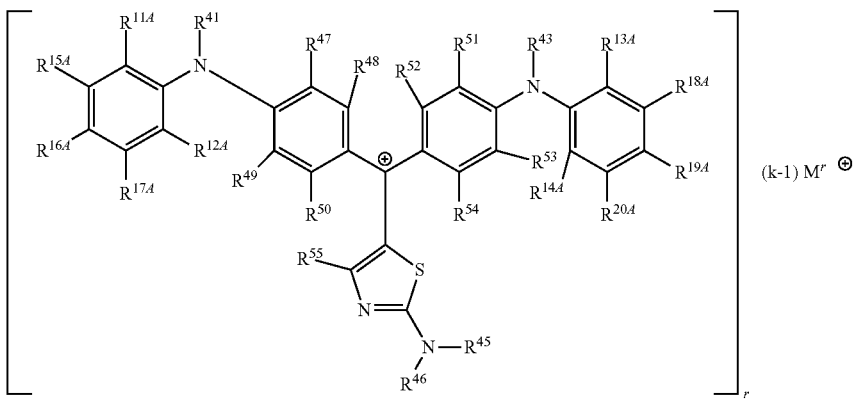

wherein
- $R^{47}$ to $R^{54}$ each independently represent a hydrogen atom, $—SO_3^-$, or a saturated hydrocarbon group having 1 to 10 carbon atoms;
- $R^{41}$ and $R^{43}$ each independently represent a hydrogen atom, a saturated hydrocarbon group having 1 to 10 carbon atoms, an aromatic hydrocarbon group having 6 to 20 carbon atoms and optionally having a substituent, or an aralkyl group having 7 to 30 carbon atoms and optionally having a substituent; the substituent which is optionally contained in the aromatic hydrocarbon group and the aralkyl group may be $—SO_3^-$;
- $R^{11A}$ to $R^{20A}$ each independently represent $—SO_3^-$, a hydrogen atom, a saturated hydrocarbon group having 1 to 10 carbon atoms, or a halogen atom;
- $R^{45}$, $R^{46}$, and $R^{55}$ each independently represent a hydrogen atom, a saturated hydrocarbon group having 1 to 10 carbon atoms and optionally having a substituent, or an aromatic hydrocarbon group having 6 to 20 carbon atoms and optionally having a substituent; the substituent which is optionally contained in the aromatic hydrocarbon group may be $—SO_3^-$;
- when the number of carbon atoms of the saturated hydrocarbon group is 2 to 10 in $R^{47}$ to $R^{54}$, $R^{41}$, $R^{43}$, $R^{11A}$ to $R^{20A}$, $R^{45}$, $R^{46}$, and $R^{55}$, $—CH_2—$ contained in the saturated hydrocarbon group is optionally replaced with at least one of $—O—$ and $—CO—$, provided that in the saturated hydrocarbon group having 2 to 10 carbon atoms, $—CH_2—$ and $—CH_2—$ adjacent to each other are not simultaneously replaced with $—O—$, and terminal $—CH_2—$ is not replaced with $—O—$ or $—CO—$;
- $M^{r+}$ represents an r-valent metal ion;
- k represents the number of a $SO_3^-$ group in the compound represented by formula (1-1);
- the compound represented by (1-1) has at least two $SO_3^-$ groups; and
- r represents an integer of 2 or more.

It is more preferable that $R^{47}$ to $R^{54}$ are each independently a hydrogen atom, $—SO_3^-$, or a methyl group. It is still more preferable that $R^{47}$ to $R^{54}$ are each independently a hydrogen atom or a methyl group.

It is preferable that $R^{41}$ and $R^{43}$ are each independently a saturated hydrocarbon group having 1 to 10 carbon atoms, an aromatic hydrocarbon group having 6 to 20 carbon atoms and optionally having a substituent, or an aralkyl group having 7 to 30 carbon atoms and optionally having a substituent. It is more preferable that $R^{41}$ and $R^{43}$ are each independently a saturated hydrocarbon group having 1 to 8 carbon atoms, a phenyl group, a tolyl group, a naphthyl group, a methyl naphthyl group; an unsubstituted aralkyl group; or an aralkyl group substituted with one or more, particularly one, selected from a halogen atom, a methoxy group, an ethoxy group, a sulfamoyl group, a methylsulfonyl group, a methoxy carbonyl group, and an ethoxycarbonyl group. It is still more preferable that $R^{41}$ and $R^{43}$ are each independently a linear alkyl group having 1 to 4 carbon atoms.

From the viewpoint of heat resistance and light resistance, it is preferable that at least any one of $R^{11A}$ and $R^{12A}$ is a halogen atom or a saturated hydrocarbon group having 1 to 10 carbon atoms; it is more preferable that at least any one of $R^{11A}$ and $R^{12A}$ is a halogen atom or a saturated hydrocarbon group having 1 to 8 carbon atoms; and it is still more preferable that at least any one of $R^{11A}$ and $R^{12A}$ is a fluorine atom or a saturated hydrocarbon group having 1 to 4 carbon atoms.

From the viewpoint of heat resistance and light resistance, it is preferable that at least any one of $R^{13A}$ and $R^{14A}$ is a halogen atom or a saturated hydrocarbon group having 1 to 10 carbon atoms; it is more preferable that at least any one of $R^{13A}$ and $R^{14A}$ is a halogen atom or a saturated hydrocarbon group having 1 to 8 carbon atoms; and it is still more preferable that at least any one of $R^{13A}$ and $R^{14A}$ is a fluorine atom or a saturated hydrocarbon group having 1 to 4 carbon atoms.

From the viewpoint of ease of synthesis, it is preferable that $R^{15A}$ to $R^{20A}$ are each independently a hydrogen atom or a saturated hydrocarbon group having 1 to 10 carbon atoms; it is more preferable that $R^{15A}$ to $R^{20A}$ are each independently a hydrogen atom or a saturated hydrocarbon group having 1 to 4 carbon atoms; and it is still more preferable that $R^{15A}$ to $R^{20A}$ are each independently a hydrogen atom or a methyl group.

Examples of the halogen atom represented by $R^{11A}$ to $R^{20A}$ include a fluorine atom, a chlorine atom, a bromine atom, an iodine atom, and a fluorine atom is preferable.

It is preferable that $R^{45}$, $R^{46}$, and $R^{55}$ are each independently a saturated hydrocarbon group having 1 to 10 carbon atoms or an aromatic hydrocarbon group having 6 to 20 carbon atoms and optionally having a substituent. It is more preferable that $R^{45}$, $R^{46}$, and $R^{55}$ are each independently an aromatic hydrocarbon group having 6 to 10 carbon atoms or a saturated hydrocarbon group having 1 to 8 carbon atoms which is optionally substituted with a halogen atom, a haloalkyl group having 1 to 4 carbon atoms, an alkoxy group having 1 to 4 carbon atoms, a hydroxy group, or a methyl-sulfonyl group. It is still more preferable that $R^{45}$, $R^{46}$, and $R^{55}$ are each independently a saturated hydrocarbon group having 1 to 8 carbon atoms or an aromatic hydrocarbon group represented by the following formula. It is particularly preferable that any one of $R^{45}$ and $R^{46}$ is a saturated hydrocarbon group having 1 to 6 carbon atoms, and the other is an aromatic hydrocarbon group having 6 to 10 carbon atoms and optionally having a substituent. It is preferable that $R^{55}$ is an aromatic hydrocarbon group having 6 to 20 carbon atoms and having a halogen atom. It is more preferable that $R^{55}$ is an aromatic hydrocarbon group having 6 to 20 carbon atoms and having two or more halogen atoms. The number of the halogen atoms contained in the aromatic hydrocarbon group represented by $R^{55}$ is preferably 1 to 6, more preferably 1 to 4, and still more preferably 2 and 3. The halogen atom is preferably a fluorine atom.

$R^{55}$ is particularly preferably an aromatic hydrocarbon group represented by the following formula. In the following formula, * represents a point of attachment to a carbon atom.

[Formula 13]

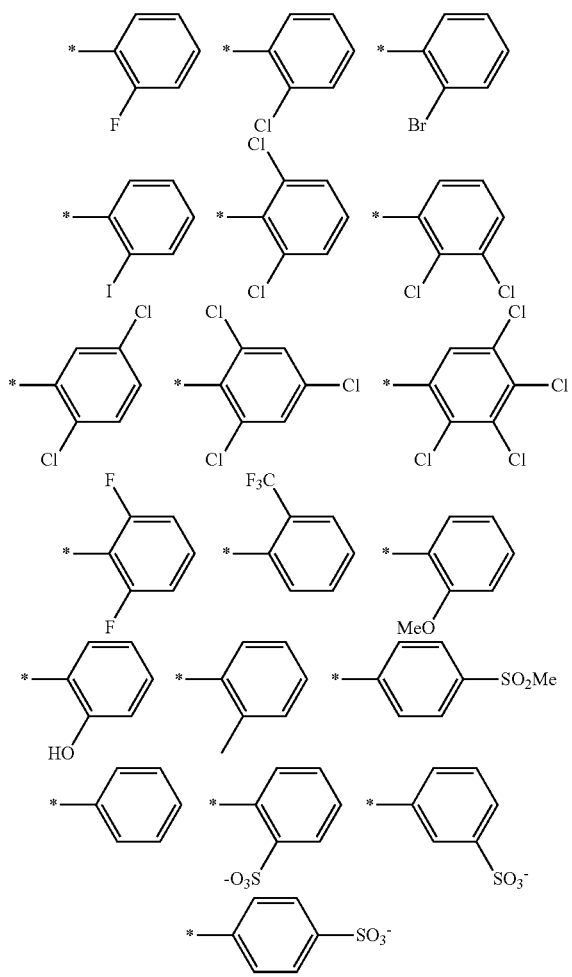

[Formula 14]

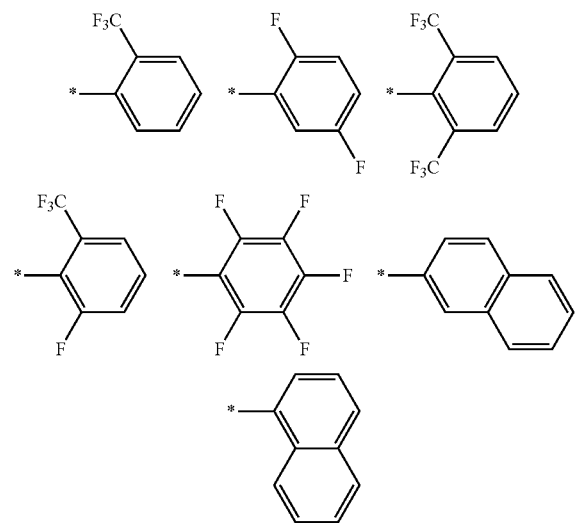

In formula (1-1), the number of —$SO_3^-$ is preferably 2 or more and 6 or less, and more preferably 4 or less.

It is preferable that —$SO_3^-$ (a) is contained as any of $R^{47}$ to $R^{54}$ and $R^{11A}$ to $R^{20A}$, (b) is bonded to any of the aromatic hydrocarbon groups having 6 to 20 carbon atoms which optionally have a substituent and is represented by $R^{41}$ and $R^{43}$, and the aralkyl group having 7 to 30 carbon atoms and optionally having a substituent and is represented by $R^{41}$ and $R^{43}$, (c) is bonded to any of the aromatic hydrocarbon groups having 6 to 20 carbon atoms which optionally have a substituent and are represented by $R^{45}$, $R^{46}$, and $R^{55}$, or is present as a combination of (a) to (c).

It is more preferable that —$SO_3^-$ is present as (a), (b), or a combination of (a) and (b).

It is still more preferable that —$SO_3^-$ is present as (a).

Among $R^{47}$ to $R^{54}$ and $R^{11A}$ to $R^{20A}$, $R^{16A}$ and $R^{19A}$ are particularly preferable.

In the above (a) to (c), it is preferable that —$SO_3^-$ is directly bonded to the aromatic hydrocarbon ring of the aromatic hydrocarbon group or aralkyl group. That is, —$SO_3^-$ preferably substitutes the hydrogen atom bonded to the aromatic hydrocarbon ring.

Two or more —$SO_3^-$ may be bonded to the same aromatic hydrocarbon ring, but these are preferably bonded to different aromatic hydrocarbon rings.

Examples of the compound (1) include compounds 1 to 514 represented by formula (1-2), as shown in following Tables 1 to 9.

However, the compound represented by formula (1-2) has two —$SO_3^-$. The two —$SO_3^-$ substitute any two of the hydrogen atoms represented by $R^h$ and $R^{11A}$ to $R^{14A}$, preferably substitute any two of the hydrogen atoms represented by $R^h$, and more preferably substitute $R^h$ located at a para position with respect to a bonding position with a nitrogen atom in a benzene ring bonded to the nitrogen atom.

[Formula 15]

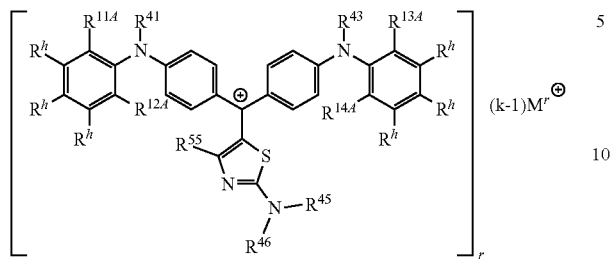

TABLE 1

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 1 | Me | Me | H | H | H | H | H | Bt | Bt | Ph1 | 1 | 2 | $Ba^{2+}$ |
| 2 | Et | Et | H | H | H | H | H | Bt | Bt | Ph1 | 1 | 2 | $Ba^{2+}$ |
| 3 | Bt | Bt | H | H | H | H | H | Bt | Bt | Ph1 | 1 | 2 | $Ba^{2+}$ |
| 4 | Et | Et | Me | H | Me | H | H | Bt | Bt | Ph1 | 1 | 2 | $Ba^{2+}$ |
| 5 | Bt | Bt | Me | H | Me | H | H | Bt | Bt | Ph1 | 1 | 2 | $Ba^{2+}$ |
| 6 | Et | Et | Me | Me | Me | Me | H | Bt | Bt | Ph1 | 1 | 2 | $Ba^{2+}$ |
| 7 | Bt | Bt | Me | Me | Me | Me | H | Bt | Bt | Ph1 | 1 | 2 | $Ba^{2+}$ |
| 8 | Et | Et | iPr | H | iPr | H | H | Bt | Bt | Ph1 | 1 | 2 | $Ba^{2+}$ |
| 9 | Bt | Bt | iPr | H | iPr | H | H | Bt | Bt | Ph1 | 1 | 2 | $Ba^{2+}$ |
| 10 | Et | Et | iPr | iPr | iPr | iPr | H | Bt | Bt | Ph1 | 1 | 2 | $Ba^{2+}$ |
| 11 | Bt | Bt | iPr | iPr | iPr | iPr | H | Bt | Bt | Ph1 | 1 | 2 | $Ba^{2+}$ |
| 12 | Et | Et | F | H | F | H | H | Bt | Bt | Ph1 | 1 | 2 | $Ba^{2+}$ |
| 13 | Bt | Bt | F | H | F | H | H | Bt | Bt | Ph1 | 1 | 2 | $Ba^{2+}$ |
| 14 | Et | Et | F | F | F | F | H | Bt | Bt | Ph1 | 1 | 2 | $Ba^{2+}$ |
| 15 | Bt | Bt | F | F | F | F | H | Bt | Bt | Ph1 | 1 | 2 | $Ba^{2+}$ |
| 16 | Me | Me | H | H | H | H | H | Et | Ph2 | Ph1 | 1 | 2 | $Ba^{2+}$ |
| 17 | Et | Et | H | H | H | H | H | Et | Ph2 | Ph1 | 1 | 2 | $Ba^{2+}$ |
| 18 | Bt | Bt | H | H | H | H | H | Et | Ph2 | Ph1 | 1 | 2 | $Ba^{2+}$ |
| 19 | Et | Et | Me | H | Me | H | H | Et | Ph2 | Ph1 | 1 | 2 | $Ba^{2+}$ |
| 20 | Bt | Bt | Me | H | Me | H | H | Et | Ph2 | Ph1 | 1 | 2 | $Ba^{2+}$ |
| 21 | Et | Et | Me | Me | Me | Me | H | Et | Ph2 | Ph1 | 1 | 2 | $Ba^{2+}$ |
| 22 | Bt | Bt | Me | Me | Me | Me | H | Et | Ph2 | Ph1 | 1 | 2 | $Ba^{2+}$ |
| 23 | Et | Et | iPr | H | iPr | H | H | Et | Ph2 | Ph1 | 1 | 2 | $Ba^{2+}$ |
| 24 | Bt | Bt | iPr | H | iPr | H | H | Et | Ph2 | Ph1 | 1 | 2 | $Ba^{2+}$ |
| 25 | Et | Et | iPr | iPr | iPr | iPr | H | Et | Ph2 | Ph1 | 1 | 2 | $Ba^{2+}$ |
| 26 | Bt | Bt | iPr | iPr | iPr | iPr | H | Et | Ph2 | Ph1 | 1 | 2 | $Ba^{2+}$ |
| 27 | Et | Et | F | H | F | H | H | Et | Ph2 | Ph1 | 1 | 2 | $Ba^{2+}$ |
| 28 | Bt | Bt | F | H | F | H | H | Et | Ph2 | Ph1 | 1 | 2 | $Ba^{2+}$ |
| 29 | Et | Et | F | F | F | F | H | Et | Ph2 | Ph1 | 1 | 2 | $Ba^{2+}$ |
| 30 | Bt | Bt | F | F | F | F | H | Et | Ph2 | Ph1 | 1 | 2 | $Ba^{2+}$ |
| 31 | Me | Me | H | H | H | H | H | Bt | Bt | Ph3 | 1 | 2 | $Ba^{2+}$ |
| 32 | Et | Et | H | H | H | H | H | Bt | Bt | Ph3 | 1 | 2 | $Ba^{2+}$ |
| 33 | Bt | Bt | H | H | H | H | H | Bt | Bt | Ph3 | 1 | 2 | $Ba^{2+}$ |
| 34 | Et | Et | Me | H | Me | H | H | Bt | Bt | Ph3 | 1 | 2 | $Ba^{2+}$ |
| 35 | Bt | Bt | Me | H | Me | H | H | Bt | Bt | Ph3 | 1 | 2 | $Ba^{2+}$ |
| 36 | Et | Et | Me | Me | Me | Me | H | Bt | Bt | Ph3 | 1 | 2 | $Ba^{2+}$ |
| 37 | Bt | Bt | Me | Me | Me | Me | H | Bt | Bt | Ph3 | 1 | 2 | $Ba^{2+}$ |
| 38 | Et | Et | iPr | H | iPr | H | H | Bt | Bt | Ph3 | 1 | 2 | $Ba^{2+}$ |
| 39 | Bt | Bt | iPr | H | iPr | H | H | Bt | Bt | Ph3 | 1 | 2 | $Ba^{2+}$ |
| 40 | Et | Et | iPr | iPr | iPr | iPr | H | Bt | Bt | Ph3 | 1 | 2 | $Ba^{2+}$ |
| 41 | Bt | Bt | iPr | iPr | iPr | iPr | H | Bt | Bt | Ph3 | 1 | 2 | $Ba^{2+}$ |
| 42 | Et | Et | F | H | F | H | H | Bt | Bt | Ph3 | 1 | 2 | $Ba^{2+}$ |
| 43 | Bt | Bt | F | H | F | H | H | Bt | Bt | Ph3 | 1 | 2 | $Ba^{2+}$ |
| 44 | Et | Et | F | F | F | F | H | Bt | Bt | Ph3 | 1 | 2 | $Ba^{2+}$ |
| 45 | Bt | Bt | F | F | F | F | H | Bt | Bt | Ph3 | 1 | 2 | $Ba^{2+}$ |
| 46 | Me | Me | H | H | H | H | H | Et | Ph2 | Ph3 | 1 | 2 | $Ba^{2+}$ |
| 47 | Et | Et | H | H | H | H | H | Et | Ph2 | Ph3 | 1 | 2 | $Ba^{2+}$ |
| 48 | Bt | Bt | H | H | H | H | H | Et | Ph2 | Ph3 | 1 | 2 | $Ba^{2+}$ |
| 49 | Et | Et | Me | H | Me | H | H | Et | Ph2 | Ph3 | 1 | 2 | $Ba^{2+}$ |
| 50 | Bt | Bt | Me | H | Me | H | H | Et | Ph2 | Ph3 | 1 | 2 | $Ba^{2+}$ |
| 51 | Et | Et | Me | Me | Me | Me | H | Et | Ph2 | Ph3 | 1 | 2 | $Ba^{2+}$ |
| 52 | Bt | Bt | Me | Me | Me | Me | H | Et | Ph2 | Ph3 | 1 | 2 | $Ba^{2+}$ |
| 53 | Et | Et | iPr | H | iPr | H | H | Et | Ph2 | Ph3 | 1 | 2 | $Ba^{2+}$ |
| 54 | Bt | Bt | iPr | H | iPr | H | H | Et | Ph2 | Ph3 | 1 | 2 | $Ba^{2+}$ |
| 55 | Et | Et | iPr | iPr | iPr | iPr | H | Et | Ph2 | Ph3 | 1 | 2 | $Ba^{2+}$ |
| 56 | Bt | Bt | iPr | iPr | iPr | iPr | H | Et | Ph2 | Ph3 | 1 | 2 | $Ba^{2+}$ |
| 57 | Et | Et | F | H | F | H | H | Et | Ph2 | Ph3 | 1 | 2 | $Ba^{2+}$ |
| 58 | Bt | Bt | F | H | F | H | H | Et | Ph2 | Ph3 | 1 | 2 | $Ba^{2+}$ |

TABLE 1-continued

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 59 | Et | Et | F | F | F | F | H | Et | Ph2 | Ph3 | 1 | 2 | $Ba^{2+}$ |
| 60 | Bt | Bt | F | F | F | F | H | Et | Ph2 | Ph3 | 1 | 2 | $Ba^{2+}$ |

TABLE 2

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 61 | Me | Me | H | H | H | H | H | Et | Ph2 | Ph4 | 1 | 2 | $Ba^{2+}$ |
| 62 | Et | Et | H | H | H | H | H | Et | Ph2 | Ph4 | 1 | 2 | $Ba^{2+}$ |
| 63 | Bt | Bt | H | H | H | H | H | Et | Ph2 | Ph4 | 1 | 2 | $Ba^{2+}$ |
| 64 | Et | Et | Me | H | Me | H | H | Et | Ph2 | Ph4 | 1 | 2 | $Ba^{2+}$ |
| 65 | Bt | Bt | Me | H | Me | H | H | Et | Ph2 | Ph4 | 1 | 2 | $Ba^{2+}$ |
| 66 | Et | Et | Me | Me | Me | Me | H | Et | Ph2 | Ph4 | 1 | 2 | $Ba^{2+}$ |
| 67 | Bt | Bt | Me | Me | Me | Me | H | Et | Ph2 | Ph4 | 1 | 2 | $Ba^{2+}$ |
| 68 | Et | Et | iPr | H | iPr | H | H | Et | Ph2 | Ph4 | 1 | 2 | $Ba^{2+}$ |
| 69 | Bt | Bt | iPr | H | iPr | H | H | Et | Ph2 | Ph4 | 1 | 2 | $Ba^{2+}$ |
| 70 | Et | Et | iPr | iPr | iPr | iPr | H | Et | Ph2 | Ph4 | 1 | 2 | $Ba^{2+}$ |
| 71 | Bt | Bt | iPr | iPr | iPr | iPr | H | Et | Ph2 | Ph4 | 1 | 2 | $Ba^{2+}$ |
| 72 | Et | Et | F | H | F | H | H | Et | Ph2 | Ph4 | 1 | 2 | $Ba^{2+}$ |
| 73 | Bt | Bt | F | H | F | H | H | Et | Ph2 | Ph4 | 1 | 2 | $Ba^{2+}$ |
| 74 | Et | Et | F | F | F | F | H | Et | Ph2 | Ph4 | 1 | 2 | $Ba^{2+}$ |
| 75 | Bt | Bt | F | F | F | F | H | Et | Ph2 | Ph4 | 1 | 2 | $Ba^{2+}$ |
| 76 | Me | Me | H | H | H | H | H | Et | Ph2 | Ph5 | 1 | 2 | $Ba^{2+}$ |
| 77 | Et | Et | H | H | H | H | H | Et | Ph2 | Ph5 | 1 | 2 | $Ba^{2+}$ |
| 78 | Bt | Bt | H | H | H | H | H | Et | Ph2 | Ph5 | 1 | 2 | $Ba^{2+}$ |
| 79 | Et | Et | Me | H | Me | H | H | Et | Ph2 | Ph5 | 1 | 2 | $Ba^{2+}$ |
| 80 | Bt | Bt | Me | H | Me | H | H | Et | Ph2 | Ph5 | 1 | 2 | $Ba^{2+}$ |
| 81 | Et | Et | Me | Me | Me | Me | H | Et | Ph2 | Ph5 | 1 | 2 | $Ba^{2+}$ |
| 82 | Bt | Bt | Me | Me | Me | Me | H | Et | Ph2 | Ph5 | 1 | 2 | $Ba^{2+}$ |
| 83 | Et | Et | iPr | H | iPr | H | H | Et | Ph2 | Ph5 | 1 | 2 | $Ba^{2+}$ |
| 84 | Bt | Bt | iPr | H | iPr | H | H | Et | Ph2 | Ph5 | 1 | 2 | $Ba^{2+}$ |
| 85 | Et | Et | iPr | iPr | iPr | iPr | H | Et | Ph2 | Ph5 | 1 | 2 | $Ba^{2+}$ |
| 86 | Bt | Bt | iPr | iPr | iPr | iPr | H | Et | Ph2 | Ph5 | 1 | 2 | $Ba^{2+}$ |
| 87 | Et | Et | F | H | F | H | H | Et | Ph2 | Ph5 | 1 | 2 | $Ba^{2+}$ |
| 88 | Bt | Bt | F | H | F | H | H | Et | Ph2 | Ph5 | 1 | 2 | $Ba^{2+}$ |
| 89 | Et | Et | F | F | F | F | H | Et | Ph2 | Ph5 | 1 | 2 | $Ba^{2+}$ |
| 90 | Bt | Bt | F | F | F | F | H | Et | Ph2 | Ph5 | 1 | 2 | $Ba^{2+}$ |
| 91 | Me | Me | H | H | H | H | H | Bt | Bt | Ph1 | 1 | 2 | $Mg^{2+}$ |
| 92 | Et | Et | H | H | H | H | H | Bt | Bt | Ph1 | 1 | 2 | $Mg^{2+}$ |
| 93 | Bt | Bt | H | H | H | H | H | Bt | Bt | Ph1 | 1 | 2 | $Mg^{2+}$ |
| 94 | Et | Et | Me | H | Me | H | H | Bt | Bt | Ph1 | 1 | 2 | $Mg^{2+}$ |
| 95 | Bt | Bt | Me | H | Me | H | H | Bt | Bt | Ph1 | 1 | 2 | $Mg^{2+}$ |
| 96 | Et | Et | Me | Me | Me | Me | H | Bt | Bt | Ph1 | 1 | 2 | $Mg^{2+}$ |
| 97 | Bt | Bt | Me | Me | Me | Me | H | Bt | Bt | Ph1 | 1 | 2 | $Mg^{2+}$ |
| 98 | Et | Et | iPr | H | iPr | H | H | Bt | Bt | Ph1 | 1 | 2 | $Mg^{2+}$ |
| 99 | Bt | Bt | iPr | H | iPr | H | H | Bt | Bt | Ph1 | 1 | 2 | $Mg^{2+}$ |
| 100 | Et | Et | iPr | iPr | iPr | iPr | H | Bt | Bt | Ph1 | 1 | 2 | $Mg^{2+}$ |
| 101 | Bt | Bt | iPr | iPr | iPr | iPr | H | Bt | Bt | Ph1 | 1 | 2 | $Mg^{2+}$ |
| 102 | Et | Et | F | H | F | H | H | Bt | Bt | Ph1 | 1 | 2 | $Mg^{2+}$ |
| 103 | Bt | Bt | F | H | F | H | H | Bt | Bt | Ph1 | 1 | 2 | $Mg^{2+}$ |
| 104 | Et | Et | F | F | F | F | H | Bt | Bt | Ph1 | 1 | 2 | $Mg^{2+}$ |
| 105 | Bt | Bt | F | F | F | F | H | Bt | Bt | Ph1 | 1 | 2 | $Mg^{2+}$ |
| 106 | Me | Me | H | H | H | H | H | Et | Ph2 | Ph1 | 1 | 2 | $Mg^{2+}$ |
| 107 | Et | Et | H | H | H | H | H | Et | Ph2 | Ph1 | 1 | 2 | $Mg^{2+}$ |
| 108 | Bt | Bt | H | H | H | H | H | Et | Ph2 | Ph1 | 1 | 2 | $Mg^{2+}$ |
| 109 | Et | Et | Me | H | Me | H | H | Et | Ph2 | Ph1 | 1 | 2 | $Mg^{2+}$ |
| 110 | Bt | Bt | Me | H | Me | H | H | Et | Ph2 | Ph1 | 1 | 2 | $Mg^{2+}$ |
| 111 | Et | Et | Me | Me | Me | Me | H | Et | Ph2 | Ph1 | 1 | 2 | $Mg^{2+}$ |
| 112 | Bt | Bt | Me | Me | Me | Me | H | Et | Ph2 | Ph1 | 1 | 2 | $Mg^{2+}$ |
| 113 | Et | Et | iPr | H | iPr | H | H | Et | Ph2 | Ph1 | 1 | 2 | $Mg^{2+}$ |
| 114 | Bt | Bt | iPr | H | iPr | H | H | Et | Ph2 | Ph1 | 1 | 2 | $Mg^{2+}$ |
| 115 | Et | Et | iPr | iPr | iPr | iPr | H | Et | Ph2 | Ph1 | 1 | 2 | $Mg^{2+}$ |
| 116 | Bt | Bt | iPr | iPr | iPr | iPr | H | Et | Ph2 | Ph1 | 1 | 2 | $Mg^{2+}$ |
| 117 | Et | Et | F | H | F | H | H | Et | Ph2 | Ph1 | 1 | 2 | $Mg^{2+}$ |
| 118 | Bt | Bt | F | H | F | H | H | Et | Ph2 | Ph1 | 1 | 2 | $Mg^{2+}$ |
| 119 | Et | Et | F | F | F | F | H | Et | Ph2 | Ph1 | 1 | 2 | $Mg^{2+}$ |
| 120 | Bt | Bt | F | F | F | F | H | Et | Ph2 | Ph1 | 1 | 2 | $Mg^{2+}$ |

TABLE 3

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 121 | Me | Me | H | H | H | H | H | Bt | Bt | Ph3 | 1 | 2 | $Mg^{2+}$ |
| 122 | Et | Et | H | H | H | H | H | Bt | Bt | Ph3 | 1 | 2 | $Mg^{2+}$ |
| 123 | Bt | Bt | H | H | H | H | H | Bt | Bt | Ph3 | 1 | 2 | $Mg^{2+}$ |
| 124 | Et | Et | Me | H | Me | H | H | Bt | Bt | Ph3 | 1 | 2 | $Mg^{2+}$ |
| 125 | Bt | Bt | Me | H | Me | H | H | Bt | Bt | Ph3 | 1 | 2 | $Mg^{2+}$ |
| 126 | Et | Et | Me | Me | Me | Me | H | Bt | Bt | Ph3 | 1 | 2 | $Mg^{2+}$ |
| 127 | Bt | Bt | Me | Me | Me | Me | H | Bt | Bt | Ph3 | 1 | 2 | $Mg^{2+}$ |
| 128 | Et | Et | iPr | H | iPr | H | H | Bt | Bt | Ph3 | 1 | 2 | $Mg^{2+}$ |
| 129 | Bt | Bt | iPr | H | iPr | H | H | Bt | Bt | Ph3 | 1 | 2 | $Mg^{2+}$ |
| 130 | Et | Et | iPr | iPr | iPr | iPr | H | Bt | Bt | Ph3 | 1 | 2 | $Mg^{2+}$ |
| 131 | Bt | Bt | iPr | iPr | iPr | iPr | H | Bt | Bt | Ph3 | 1 | 2 | $Mg^{2+}$ |
| 132 | Et | Et | F | H | F | H | H | Bt | Bt | Ph3 | 1 | 2 | $Mg^{2+}$ |
| 133 | Bt | Bt | F | H | F | H | H | Bt | Bt | Ph3 | 1 | 2 | $Mg^{2+}$ |
| 134 | Et | Et | F | F | F | F | H | Bt | Bt | Ph3 | 1 | 2 | $Mg^{2+}$ |
| 135 | Bt | Bt | F | F | F | F | H | Bt | Bt | Ph3 | 1 | 2 | $Mg^{2+}$ |
| 136 | Me | Me | H | H | H | H | H | Et | Ph2 | Ph3 | 1 | 2 | $Mg^{2+}$ |
| 137 | Et | Et | H | H | H | H | H | Et | Ph2 | Ph3 | 1 | 2 | $Mg^{2+}$ |
| 138 | Bt | Bt | H | H | H | H | H | Et | Ph2 | Ph3 | 1 | 2 | $Mg^{2+}$ |
| 139 | Et | Et | Me | H | Me | H | H | Et | Ph2 | Ph3 | 1 | 2 | $Mg^{2+}$ |
| 140 | Bt | Bt | Me | H | Me | H | H | Et | Ph2 | Ph3 | 1 | 2 | $Mg^{2+}$ |
| 141 | Et | Et | Me | Me | Me | Me | H | Et | Ph2 | Ph3 | 1 | 2 | $Mg^{2+}$ |
| 142 | Bt | Bt | Me | Me | Me | Me | H | Et | Ph2 | Ph3 | 1 | 2 | $Mg^{2+}$ |
| 143 | Et | Et | iPr | H | iPr | H | H | Et | Ph2 | Ph3 | 1 | 2 | $Mg^{2+}$ |
| 144 | Bt | Bt | iPr | H | iPr | H | H | Et | Ph2 | Ph3 | 1 | 2 | $Mg^{2+}$ |
| 145 | Et | Et | iPr | iPr | iPr | iPr | H | Et | Ph2 | Ph3 | 1 | 2 | $Mg^{2+}$ |
| 146 | Bt | Bt | iPr | iPr | iPr | iPr | H | Et | Ph2 | Ph3 | 1 | 2 | $Mg^{2+}$ |
| 147 | Et | Et | F | H | F | H | H | Et | Ph2 | Ph3 | 1 | 2 | $Mg^{2+}$ |
| 148 | Bt | Bt | F | H | F | H | H | Et | Ph2 | Ph3 | 1 | 2 | $Mg^{2+}$ |
| 149 | Et | Et | F | F | F | F | H | Et | Ph2 | Ph3 | 1 | 2 | $Mg^{2+}$ |
| 150 | Bt | Bt | F | F | F | F | H | Et | Ph2 | Ph3 | 1 | 2 | $Mg^{2+}$ |
| 151 | Me | Me | H | H | H | H | H | Et | Ph2 | Ph4 | 1 | 2 | $Mg^{2+}$ |
| 152 | Et | Et | H | H | H | H | H | Et | Ph2 | Ph4 | 1 | 2 | $Mg^{2+}$ |
| 153 | Bt | Bt | H | H | H | H | H | Et | Ph2 | Ph4 | 1 | 2 | $Mg^{2+}$ |
| 154 | Et | Et | Me | H | Me | H | H | Et | Ph2 | Ph4 | 1 | 2 | $Mg^{2+}$ |
| 155 | Bt | Bt | Me | H | Me | H | H | Et | Ph2 | Ph4 | 1 | 2 | $Mg^{2+}$ |
| 156 | Et | Et | Me | Me | Me | Me | H | Et | Ph2 | Ph4 | 1 | 2 | $Mg^{2+}$ |
| 157 | Bt | Bt | Me | Me | Me | Me | H | Et | Ph2 | Ph4 | 1 | 2 | $Mg^{2+}$ |
| 158 | Et | Et | iPr | H | iPr | H | H | Et | Ph2 | Ph4 | 1 | 2 | $Mg^{2+}$ |
| 159 | Bt | Bt | iPr | H | iPr | H | H | Et | Ph2 | Ph4 | 1 | 2 | $Mg^{2+}$ |
| 160 | Et | Et | iPr | iPr | iPr | iPr | H | Et | Ph2 | Ph4 | 1 | 2 | $Mg^{2+}$ |
| 161 | Bt | Bt | iPr | iPr | iPr | iPr | H | Et | Ph2 | Ph4 | 1 | 2 | $Mg^{2+}$ |
| 162 | Et | Et | F | H | F | H | H | Et | Ph2 | Ph4 | 1 | 2 | $Mg^{2+}$ |
| 163 | Bt | Bt | F | H | F | H | H | Et | Ph2 | Ph4 | 1 | 2 | $Mg^{2+}$ |
| 164 | Et | Et | F | F | F | F | H | Et | Ph2 | Ph4 | 1 | 2 | $Mg^{2+}$ |
| 165 | Bt | Bt | F | F | F | F | H | Et | Ph2 | Ph4 | 1 | 2 | $Mg^{2+}$ |
| 166 | Me | Me | H | H | H | H | H | Et | Ph2 | Ph5 | 1 | 2 | $Mg^{2+}$ |
| 167 | Et | Et | H | H | H | H | H | Et | Ph2 | Ph5 | 1 | 2 | $Mg^{2+}$ |
| 168 | Bt | Bt | H | H | H | H | H | Et | Ph2 | Ph5 | 1 | 2 | $Mg^{2+}$ |
| 169 | Et | Et | Me | H | Me | H | H | Et | Ph2 | Ph5 | 1 | 2 | $Mg^{2+}$ |
| 170 | Bt | Bt | Me | H | Me | H | H | Et | Ph2 | Ph5 | 1 | 2 | $Mg^{2+}$ |
| 171 | Et | Et | Me | Me | Me | Me | H | Et | Ph2 | Ph5 | 1 | 2 | $Mg^{2+}$ |
| 172 | Bt | Bt | Me | Me | Me | Me | H | Et | Ph2 | Ph5 | 1 | 2 | $Mg^{2+}$ |
| 173 | Et | Et | iPr | H | iPr | H | H | Et | Ph2 | Ph5 | 1 | 2 | $Mg^{2+}$ |
| 174 | Bt | Bt | iPr | H | iPr | H | H | Et | Ph2 | Ph5 | 1 | 2 | $Mg^{2+}$ |
| 175 | Et | Et | iPr | iPr | iPr | iPr | H | Et | Ph2 | Ph5 | 1 | 2 | $Mg^{2+}$ |
| 176 | Bt | Bt | iPr | iPr | iPr | iPr | H | Et | Ph2 | Ph5 | 1 | 2 | $Mg^{2+}$ |
| 177 | Et | Et | F | H | F | H | H | Et | Ph2 | Ph5 | 1 | 2 | $Mg^{2+}$ |
| 178 | Bt | Bt | F | H | F | H | H | Et | Ph2 | Ph5 | 1 | 2 | $Mg^{2+}$ |
| 179 | Et | Et | F | F | F | F | H | Et | Ph2 | Ph5 | 1 | 2 | $Mg^{2+}$ |
| 180 | Bt | Bt | F | F | F | F | H | Et | Ph2 | Ph5 | 1 | 2 | $Mg^{2+}$ |

TABLE 4

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 181 | Me | Me | H | H | H | H | H | Bt | Bt | Ph1 | 1 | 2 | $Zn^{2+}$ |
| 182 | Et | Et | H | H | H | H | H | Bt | Bt | Ph1 | 1 | 2 | $Zn^{2+}$ |
| 183 | Bt | Bt | H | H | H | H | H | Bt | Bt | Ph1 | 1 | 2 | $Zn^{2+}$ |
| 184 | Et | Et | Me | H | Me | H | H | Bt | Bt | Ph1 | 1 | 2 | $Zn^{2+}$ |
| 185 | Bt | Bt | Me | H | Me | H | H | Bt | Bt | Ph1 | 1 | 2 | $Zn^{2+}$ |
| 186 | Et | Et | Me | Me | Me | Me | H | Bt | Bt | Ph1 | 1 | 2 | $Zn^{2+}$ |
| 187 | Bt | Bt | Me | Me | Me | Me | H | Bt | Bt | Ph1 | 1 | 2 | $Zn^{2+}$ |
| 188 | Et | Et | iPr | H | iPr | H | H | Bt | Bt | Ph1 | 1 | 2 | $Zn^{2+}$ |
| 189 | Bt | Bt | iPr | H | iPr | H | H | Bt | Bt | Ph1 | 1 | 2 | $Zn^{2+}$ |
| 190 | Et | Et | iPr | iPr | iPr | iPr | H | Bt | Bt | Ph1 | 1 | 2 | $Zn^{2+}$ |

TABLE 4-continued

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 191 | Bt | Bt | iPr | iPr | iPr | iPr | H | Bt | Bt | Ph1 | 1 | 2 | $Zn^{2+}$ |
| 192 | Et | Et | F | H | F | H | H | Bt | Bt | Ph1 | 1 | 2 | $Zn^{2+}$ |
| 193 | Bt | Bt | F | H | F | H | H | Bt | Bt | Ph1 | 1 | 2 | $Zn^{2+}$ |
| 194 | Et | Et | F | F | F | F | H | Bt | Bt | Ph1 | 1 | 2 | $Zn^{2+}$ |
| 195 | Bt | Bt | F | F | F | F | H | Bt | Bt | Ph1 | 1 | 2 | $Zn^{2+}$ |
| 196 | Me | Me | H | H | H | H | H | Et | Ph2 | Ph1 | 1 | 2 | $Zn^{2+}$ |
| 197 | Et | Et | H | H | H | H | H | Et | Ph2 | Ph1 | 1 | 2 | $Zn^{2+}$ |
| 198 | Bt | Bt | H | H | H | H | H | Et | Ph2 | Ph1 | 1 | 2 | $Zn^{2+}$ |
| 199 | Et | Et | Me | H | Me | H | H | Et | Ph2 | Ph1 | 1 | 2 | $Zn^{2+}$ |
| 200 | Bt | Bt | Me | H | Me | H | H | Et | Ph2 | Ph1 | 1 | 2 | $Zn^{2+}$ |
| 201 | Et | Et | Me | Me | Me | Me | H | Et | Ph2 | Ph1 | 1 | 2 | $Zn^{2+}$ |
| 202 | Bt | Bt | Me | Me | Me | Me | H | Et | Ph2 | Ph1 | 1 | 2 | $Zn^{2+}$ |
| 203 | Et | Et | iPr | H | iPr | H | H | Et | Ph2 | Ph1 | 1 | 2 | $Zn^{2+}$ |
| 204 | Bt | Bt | iPr | H | iPr | H | H | Et | Ph2 | Ph1 | 1 | 2 | $Zn^{2+}$ |
| 205 | Et | Et | iPr | iPr | iPr | iPr | H | Et | Ph2 | Ph1 | 1 | 2 | $Zn^{2+}$ |
| 206 | Bt | Bt | iPr | iPr | iPr | iPr | H | Et | Ph2 | Ph1 | 1 | 2 | $Zn^{2+}$ |
| 207 | Et | Et | F | H | F | H | H | Et | Ph2 | Ph1 | 1 | 2 | $Zn^{2+}$ |
| 208 | Bt | Bt | F | H | F | H | H | Et | Ph2 | Ph1 | 1 | 2 | $Zn^{2+}$ |
| 209 | Et | Et | F | F | F | F | H | Et | Ph2 | Ph1 | 1 | 2 | $Zn^{2+}$ |
| 210 | Bt | Bt | F | F | F | F | H | Et | Ph2 | Ph1 | 1 | 2 | $Zn^{2+}$ |
| 211 | Me | Me | H | H | H | H | H | Bt | Bt | Ph3 | 1 | 2 | $Zn^{2+}$ |
| 212 | Et | Et | H | H | H | H | H | Bt | Bt | Ph3 | 1 | 2 | $Zn^{2+}$ |
| 213 | Bt | Bt | H | H | H | H | H | Bt | Bt | Ph3 | 1 | 2 | $Zn^{2+}$ |
| 214 | Et | Et | Me | H | Me | H | H | Bt | Bt | Ph3 | 1 | 2 | $Zn^{2+}$ |
| 215 | Bt | Bt | Me | H | Me | H | H | Bt | Bt | Ph3 | 1 | 2 | $Zn^{2+}$ |
| 216 | Et | Et | Me | Me | Me | Me | H | Bt | Bt | Ph3 | 1 | 2 | $Zn^{2+}$ |
| 217 | Bt | Bt | Me | Me | Me | Me | H | Bt | Bt | Ph3 | 1 | 2 | $Zn^{2+}$ |
| 218 | Et | Et | iPr | H | iPr | H | H | Bt | Bt | Ph3 | 1 | 2 | $Zn^{2+}$ |
| 219 | Bt | Bt | iPr | H | iPr | H | H | Bt | Bt | Ph3 | 1 | 2 | $Zn^{2+}$ |
| 220 | Et | Et | iPr | iPr | iPr | iPr | H | Bt | Bt | Ph3 | 1 | 2 | $Zn^{2+}$ |
| 221 | Bt | Bt | iPr | iPr | iPr | iPr | H | Bt | Bt | Ph3 | 1 | 2 | $Zn^{2+}$ |
| 222 | Et | Et | F | H | F | H | H | Bt | Bt | Ph3 | 1 | 2 | $Zn^{2+}$ |
| 223 | Bt | Bt | F | H | F | H | H | Bt | Bt | Ph3 | 1 | 2 | $Zn^{2+}$ |
| 224 | Et | Et | F | F | F | F | H | Bt | Bt | Ph3 | 1 | 2 | $Zn^{2+}$ |
| 225 | Bt | Bt | F | F | F | F | H | Bt | Bt | Ph3 | 1 | 2 | $Zn^{2+}$ |
| 226 | Me | Me | H | H | H | H | H | Et | Ph2 | Ph3 | 1 | 2 | $Zn^{2+}$ |
| 227 | Et | Et | H | H | H | H | H | Et | Ph2 | Ph3 | 1 | 2 | $Zn^{2+}$ |
| 228 | Bt | Bt | H | H | H | H | H | Et | Ph2 | Ph3 | 1 | 2 | $Zn^{2+}$ |
| 229 | Et | Et | Me | H | Me | H | H | Et | Ph2 | Ph3 | 1 | 2 | $Zn^{2+}$ |
| 230 | Bt | Bt | Me | H | Me | H | H | Et | Ph2 | Ph3 | 1 | 2 | $Zn^{2+}$ |
| 231 | Et | Et | Me | Me | Me | Me | H | Et | Ph2 | Ph3 | 1 | 2 | $Zn^{2+}$ |
| 232 | Bt | Bt | Me | Me | Me | Me | H | Et | Ph2 | Ph3 | 1 | 2 | $Zn^{2+}$ |
| 233 | Et | Et | iPr | H | iPr | H | H | Et | Ph2 | Ph3 | 1 | 2 | $Zn^{2+}$ |
| 234 | Bt | Bt | iPr | H | iPr | H | H | Et | Ph2 | Ph3 | 1 | 2 | $Zn^{2+}$ |
| 235 | Et | Et | iPr | iPr | iPr | iPr | H | Et | Ph2 | Ph3 | 1 | 2 | $Zn^{2+}$ |
| 236 | Bt | Bt | iPr | iPr | iPr | iPr | H | Et | Ph2 | Ph3 | 1 | 2 | $Zn^{2+}$ |
| 237 | Et | Et | F | H | F | H | H | Et | Ph2 | Ph3 | 1 | 2 | $Zn^{2+}$ |
| 238 | Bt | Bt | F | H | F | H | H | Et | Ph2 | Ph3 | 1 | 2 | $Zn^{2+}$ |
| 239 | Et | Et | F | F | F | F | H | Et | Ph2 | Ph3 | 1 | 2 | $Zn^{2+}$ |
| 240 | Bt | Bt | F | F | F | F | H | Et | Ph2 | Ph3 | 1 | 2 | $Zn^{2+}$ |

TABLE 5

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 241 | Me | Me | H | H | H | H | H | Et | Ph2 | Ph4 | 1 | 2 | $Zn^{2+}$ |
| 242 | Et | Et | H | H | H | H | H | Et | Ph2 | Ph4 | 1 | 2 | $Zn^{2+}$ |
| 243 | Bt | Bt | H | H | H | H | H | Et | Ph2 | Ph4 | 1 | 2 | $Zn^{2+}$ |
| 244 | Et | Et | Me | H | Me | H | H | Et | Ph2 | Ph4 | 1 | 2 | $Zn^{2+}$ |
| 245 | Bt | Bt | Me | H | Me | H | H | Et | Ph2 | Ph4 | 1 | 2 | $Zn^{2+}$ |
| 246 | Et | Et | Me | Me | Me | Me | H | Et | Ph2 | Ph4 | 1 | 2 | $Zn^{2+}$ |
| 247 | Bt | Bt | Me | Me | Me | Me | H | Et | Ph2 | Ph4 | 1 | 2 | $Zn^{2+}$ |
| 248 | Et | Et | iPr | H | iPr | H | H | Et | Ph2 | Ph4 | 1 | 2 | $Zn^{2+}$ |
| 249 | Bt | Bt | iPr | H | iPr | H | H | Et | Ph2 | Ph4 | 1 | 2 | $Zn^{2+}$ |
| 250 | Et | Et | iPr | iPr | iPr | iPr | H | Et | Ph2 | Ph4 | 1 | 2 | $Zn^{2+}$ |
| 251 | Bt | Bt | iPr | iPr | iPr | iPr | H | Et | Ph2 | Ph4 | 1 | 2 | $Zn^{2+}$ |
| 252 | Et | Et | F | H | F | H | H | Et | Ph2 | Ph4 | 1 | 2 | $Zn^{2+}$ |
| 253 | Bt | Bt | F | H | F | H | H | Et | Ph2 | Ph4 | 1 | 2 | $Zn^{2+}$ |
| 254 | Et | Et | F | F | F | F | H | Et | Ph2 | Ph4 | 1 | 2 | $Zn^{2+}$ |
| 255 | Bt | Bt | F | F | F | F | H | Et | Ph2 | Ph4 | 1 | 2 | $Zn^{2+}$ |
| 256 | Me | Me | H | H | H | H | H | Et | Ph2 | Ph5 | 1 | 2 | $Zn^{2+}$ |
| 257 | Et | Et | H | H | H | H | H | Et | Ph2 | Ph5 | 1 | 2 | $Zn^{2+}$ |
| 258 | Bt | Bt | H | H | H | H | H | Et | Ph2 | Ph5 | 1 | 2 | $Zn^{2+}$ |
| 259 | Et | Et | Me | H | Me | H | H | Et | Ph2 | Ph5 | 1 | 2 | $Zn^{2+}$ |
| 260 | Bt | Bt | Me | H | Me | H | H | Et | Ph2 | Ph5 | 1 | 2 | $Zn^{2+}$ |

TABLE 5-continued

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 261 | Et | Et | Me | Me | Me | Me | H | Et | Ph2 | Ph5 | 1 | 2 | $Zn^{2+}$ |
| 262 | Bt | Bt | Me | Me | Me | Me | H | Et | Ph2 | Ph5 | 1 | 2 | $Zn^{2+}$ |
| 263 | Et | Et | iPr | H | iPr | H | H | Et | Ph2 | Ph5 | 1 | 2 | $Zn^{2+}$ |
| 264 | Bt | Bt | iPr | H | iPr | H | H | Et | Ph2 | Ph5 | 1 | 2 | $Zn^{2+}$ |
| 265 | Et | Et | iPr | iPr | iPr | iPr | H | Et | Ph2 | Ph5 | 1 | 2 | $Zn^{2+}$ |
| 266 | Bt | Bt | iPr | iPr | iPr | iPr | H | Et | Ph2 | Ph5 | 1 | 2 | $Zn^{2+}$ |
| 267 | Et | Et | F | H | F | H | H | Et | Ph2 | Ph5 | 1 | 2 | $Zn^{2+}$ |
| 268 | Bt | Bt | F | H | F | H | H | Et | Ph2 | Ph5 | 1 | 2 | $Zn^{2+}$ |
| 269 | Et | Et | F | F | F | F | H | Et | Ph2 | Ph5 | 1 | 2 | $Zn^{2+}$ |
| 270 | Bt | Bt | F | F | F | F | H | Et | Ph2 | Ph5 | 1 | 2 | $Zn^{2+}$ |
| 271 | Et | Et | Me | Me | Me | Me | H | Et | Ph10 | Ph3 | 1 | 2 | $Ba^{2+}$ |
| 272 | Et | Et | Me | Me | Me | Me | H | Bt | Ph10 | Ph3 | 1 | 2 | $Ba^{2+}$ |
| 273 | Et | Et | Me | Me | Me | Me | H | Ph1 | Ph10 | Ph3 | 1 | 2 | $Ba^{2+}$ |
| 274 | Et | Et | Me | Me | Me | Me | H | Ph2 | Ph10 | Ph3 | 1 | 2 | $Ba^{2+}$ |
| 275 | Me | Me | H | H | H | H | H | Et | Ph10 | Ph3 | 1 | 2 | $Ba^{2+}$ |
| 276 | Me | Me | H | H | H | H | H | Bt | Ph10 | Ph3 | 1 | 2 | $Ba^{2+}$ |
| 277 | Me | Me | H | H | H | H | H | Ph1 | Ph10 | Ph3 | 1 | 2 | $Ba^{2+}$ |
| 278 | Me | Me | H | H | H | H | H | Ph2 | Ph10 | Ph3 | 1 | 2 | $Ba^{2+}$ |
| 279 | Et | Et | Me | Me | Me | Me | H | Et | Ph10 | Ph4 | 1 | 2 | $Ba^{2+}$ |
| 280 | Et | Et | Me | Me | Me | Me | H | Bt | Ph10 | Ph4 | 1 | 2 | $Ba^{2+}$ |
| 281 | Et | Et | Me | Me | Me | Me | H | Ph1 | Ph10 | Ph4 | 1 | 2 | $Ba^{2+}$ |
| 282 | Et | Et | Me | Me | Me | Me | H | Ph2 | Ph10 | Ph4 | 1 | 2 | $Ba^{2+}$ |
| 283 | Me | Me | H | H | H | H | H | Et | Ph10 | Ph4 | 1 | 2 | $Ba^{2+}$ |
| 284 | Me | Me | H | H | H | H | H | Bt | Ph10 | Ph4 | 1 | 2 | $Ba^{2+}$ |
| 285 | Me | Me | H | H | H | H | H | Ph1 | Ph10 | Ph4 | 1 | 2 | $Ba^{2+}$ |
| 286 | Me | Me | H | H | H | H | H | Ph2 | Ph10 | Ph4 | 1 | 2 | $Ba^{2+}$ |
| 287 | Et | Et | Me | Me | Me | Me | H | Et | Ph10 | Ph5 | 1 | 2 | $Ba^{2+}$ |
| 288 | Et | Et | Me | Me | Me | Me | H | Bt | Ph10 | Ph5 | 1 | 2 | $Ba^{2+}$ |
| 289 | Et | Et | Me | Me | Me | Me | H | Ph1 | Ph10 | Ph5 | 1 | 2 | $Ba^{2+}$ |
| 290 | Et | Et | Me | Me | Me | Me | H | Ph2 | Ph10 | Ph5 | 1 | 2 | $Ba^{2+}$ |
| 291 | Me | Me | H | H | H | H | H | Et | Ph10 | Ph5 | 1 | 2 | $Ba^{2+}$ |
| 292 | Me | Me | H | H | H | H | H | Bt | Ph10 | Ph5 | 1 | 2 | $Ba^{2+}$ |
| 293 | Me | Me | H | H | H | H | H | Ph1 | Ph10 | Ph5 | 1 | 2 | $Ba^{2+}$ |
| 294 | Me | Me | H | H | H | H | H | Ph2 | Ph10 | Ph5 | 1 | 2 | $Ba^{2+}$ |
| 295 | Et | Et | Me | Me | Me | Me | H | Et | Ph10 | Ph6 | 1 | 2 | $Ba^{2+}$ |
| 296 | Et | Et | Me | Me | Me | Me | H | Bt | Ph10 | Ph6 | 1 | 2 | $Ba^{2+}$ |
| 297 | Et | Et | Me | Me | Me | Me | H | Ph1 | Ph10 | Ph6 | 1 | 2 | $Ba^{2+}$ |
| 298 | Et | Et | Me | Me | Me | Me | H | Ph2 | Ph10 | Ph6 | 1 | 2 | $Ba^{2+}$ |
| 299 | Et | Et | Me | Me | Me | Me | H | Et | Ph2 | Ph6 | 1 | 2 | $Ba^{2+}$ |
| 300 | Me | Me | H | H | H | H | H | Et | Ph10 | Ph6 | 1 | 2 | $Ba^{2+}$ |

TABLE 6

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 301 | Me | Me | H | H | H | H | H | Bt | Ph10 | Ph6 | 1 | 2 | $Ba^{2+}$ |
| 302 | Me | Me | H | H | H | H | H | Ph1 | Ph10 | Ph6 | 1 | 2 | $Ba^{2+}$ |
| 303 | Me | Me | H | H | H | H | H | Ph2 | Ph10 | Ph6 | 1 | 2 | $Ba^{2+}$ |
| 304 | Me | Me | H | H | H | H | H | Et | Ph2 | Ph6 | 1 | 2 | $Ba^{2+}$ |
| 305 | Et | Et | Me | Me | Me | Me | H | Et | Ph10 | Ph7 | 1 | 2 | $Ba^{2+}$ |
| 306 | Et | Et | Me | Me | Me | Me | H | Bt | Ph10 | Ph7 | 1 | 2 | $Ba^{2+}$ |
| 307 | Et | Et | Me | Me | Me | Me | H | Ph1 | Ph10 | Ph7 | 1 | 2 | $Ba^{2+}$ |
| 308 | Et | Et | Me | Me | Me | Me | H | Ph2 | Ph10 | Ph7 | 1 | 2 | $Ba^{2+}$ |
| 309 | Et | Et | Me | Me | Me | Me | H | Et | Ph2 | Ph7 | 1 | 2 | $Ba^{2+}$ |
| 310 | Me | Me | H | H | H | H | H | Et | Bt | Ph7 | 1 | 2 | $Ba^{2+}$ |
| 311 | Me | Me | H | H | H | H | H | Bt | Bt | Ph7 | 1 | 2 | $Ba^{2+}$ |
| 312 | Me | Me | H | H | H | H | H | Ph1 | Ph10 | Ph7 | 1 | 2 | $Ba^{2+}$ |
| 313 | Me | Me | H | H | H | H | H | Ph2 | Ph10 | Ph7 | 1 | 2 | $Ba^{2+}$ |
| 314 | Me | Me | H | H | H | H | H | Et | Ph2 | Ph7 | 1 | 2 | $Ba^{2+}$ |
| 315 | Et | Et | Me | Me | Me | Me | H | Et | Ph10 | Ph8 | 1 | 2 | $Ba^{2+}$ |
| 316 | Et | Et | Me | Me | Me | Me | H | Bt | Ph10 | Ph8 | 1 | 2 | $Ba^{2+}$ |
| 317 | Et | Et | Me | Me | Me | Me | H | Ph1 | Ph10 | Ph8 | 1 | 2 | $Ba^{2+}$ |
| 318 | Et | Et | Me | Me | Me | Me | H | Ph2 | Ph10 | Ph8 | 1 | 2 | $Ba^{2+}$ |
| 319 | Et | Et | Me | Me | Me | Me | H | Et | Ph2 | Ph8 | 1 | 2 | $Ba^{2+}$ |
| 320 | Me | Me | H | H | H | H | H | Et | Bt | Ph8 | 1 | 2 | $Ba^{2+}$ |
| 321 | Me | Me | H | H | H | H | H | Bt | Bt | Ph8 | 1 | 2 | $Ba^{2+}$ |
| 322 | Me | Me | H | H | H | H | H | Ph1 | Ph10 | Ph8 | 1 | 2 | $Ba^{2+}$ |
| 323 | Me | Me | H | H | H | H | H | Ph2 | Ph10 | Ph8 | 1 | 2 | $Ba^{2+}$ |
| 324 | Me | Me | H | H | H | H | H | Et | Ph2 | Ph8 | 1 | 2 | $Ba^{2+}$ |
| 325 | Et | Et | Me | Me | Me | Me | H | Et | Ph10 | Ph9 | 1 | 2 | $Ba^{2+}$ |
| 326 | Et | Et | Me | Me | Me | Me | H | Bt | Ph10 | Ph9 | 1 | 2 | $Ba^{2+}$ |
| 327 | Et | Et | Me | Me | Me | Me | H | Ph1 | Ph10 | Ph9 | 1 | 2 | $Ba^{2+}$ |
| 328 | Et | Et | Me | Me | Me | Me | H | Ph2 | Ph10 | Ph9 | 1 | 2 | $Ba^{2+}$ |
| 329 | Et | Et | Me | Me | Me | Me | H | Et | Ph2 | Ph9 | 1 | 2 | $Ba^{2+}$ |

TABLE 6-continued

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 330 | Me | Me | H | H | H | H | H | Et | Ph2 | Ph9 | 1 | 2 | $Ba^{2+}$ |
| 331 | Me | Me | H | H | H | H | H | Bt | Ph10 | Ph9 | 1 | 2 | $Ba^{2+}$ |
| 332 | Me | Me | H | H | H | H | H | Ph1 | Ph10 | Ph9 | 1 | 2 | $Ba^{2+}$ |
| 333 | Me | Me | H | H | H | H | H | Ph2 | Ph10 | Ph9 | 1 | 2 | $Ba^{2+}$ |
| 334 | Me | Me | H | H | H | H | H | Et | Ph2 | Ph9 | 1 | 2 | $Ba^{2+}$ |

TABLE 7

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 335 | Me | Me | H | H | H | H | H | Bt | Bt | Ph1 | 1 | 2 | $Mn^{2+}$ |
| 336 | Et | Et | H | H | H | H | H | Bt | Bt | Ph1 | 1 | 2 | $Mn^{2+}$ |
| 337 | Bt | Bt | H | H | H | H | H | Bt | Bt | Ph1 | 1 | 2 | $Mn^{2+}$ |
| 338 | Et | Et | Me | H | Me | H | H | Bt | Bt | Ph1 | 1 | 2 | $Mn^{2+}$ |
| 339 | Bt | Bt | Me | H | Me | H | H | Bt | Bt | Ph1 | 1 | 2 | $Mn^{2+}$ |
| 340 | Et | Et | Me | Me | Me | Me | H | Bt | Bt | Ph1 | 1 | 2 | $Mn^{2+}$ |
| 341 | Bt | Bt | Me | Me | Me | Me | H | Bt | Bt | Ph1 | 1 | 2 | $Mn^{2+}$ |
| 342 | Et | Et | iPr | H | iPr | H | H | Bt | Bt | Ph1 | 1 | 2 | $Mn^{2+}$ |
| 343 | Bt | Bt | iPr | H | iPr | H | H | Bt | Bt | Ph1 | 1 | 2 | $Mn^{2+}$ |
| 344 | Et | Et | iPr | iPr | iPr | iPr | H | Bt | Bt | Ph1 | 1 | 2 | $Mn^{2+}$ |
| 345 | Bt | Bt | iPr | iPr | iPr | iPr | H | Bt | Bt | Ph1 | 1 | 2 | $Mn^{2+}$ |
| 346 | Et | Et | F | H | F | H | H | Bt | Bt | Ph1 | 1 | 2 | $Mn^{2+}$ |
| 347 | Bt | Bt | F | H | F | H | H | Bt | Bt | Ph1 | 1 | 2 | $Mn^{2+}$ |
| 348 | Et | Et | F | F | F | F | H | Bt | Bt | Ph1 | 1 | 2 | $Mn^{2+}$ |
| 349 | Bt | Bt | F | F | F | F | H | Bt | Bt | Ph1 | 1 | 2 | $Mn^{2+}$ |
| 350 | Me | Me | H | H | H | H | H | Et | Ph2 | Ph1 | 1 | 2 | $Mn^{2+}$ |
| 351 | Et | Et | H | H | H | H | H | Et | Ph2 | Ph1 | 1 | 2 | $Mn^{2+}$ |
| 352 | Bt | Bt | H | H | H | H | H | Et | Ph2 | Ph1 | 1 | 2 | $Mn^{2+}$ |
| 353 | Et | Et | Me | H | Me | H | H | Et | Ph2 | Ph1 | 1 | 2 | $Mn^{2+}$ |
| 354 | Bt | Bt | Me | H | Me | H | H | Et | Ph2 | Ph1 | 1 | 2 | $Mn^{2+}$ |
| 355 | Et | Et | Me | Me | Me | Me | H | Et | Ph2 | Ph1 | 1 | 2 | $Mn^{2+}$ |
| 356 | Bt | Bt | Me | Me | Me | Me | H | Et | Ph2 | Ph1 | 1 | 2 | $Mn^{2+}$ |
| 357 | Et | Et | iPr | H | iPr | H | H | Et | Ph2 | Ph1 | 1 | 2 | $Mn^{2+}$ |
| 358 | Bt | Bt | iPr | H | iPr | H | H | Et | Ph2 | Ph1 | 1 | 2 | $Mn^{2+}$ |
| 359 | Et | Et | iPr | iPr | iPr | iPr | H | Et | Ph2 | Ph1 | 1 | 2 | $Mn^{2+}$ |
| 360 | Bt | Bt | iPr | iPr | iPr | iPr | H | Et | Ph2 | Ph1 | 1 | 2 | $Mn^{2+}$ |
| 361 | Et | Et | F | H | F | H | H | Et | Ph2 | Ph1 | 1 | 2 | $Mn^{2+}$ |
| 362 | Bt | Bt | F | H | F | H | H | Et | Ph2 | Ph1 | 1 | 2 | $Mn^{2+}$ |
| 363 | Et | Et | F | F | F | F | H | Et | Ph2 | Ph1 | 1 | 2 | $Mn^{2+}$ |
| 364 | Bt | Bt | F | F | F | F | H | Et | Ph2 | Ph1 | 1 | 2 | $Mn^{2+}$ |
| 365 | Me | Me | H | H | H | H | H | Bt | Bt | Ph3 | 1 | 2 | $Mn^{2+}$ |
| 366 | Et | Et | H | H | H | H | H | Bt | Bt | Ph3 | 1 | 2 | $Mn^{2+}$ |
| 367 | Bt | Bt | H | H | H | H | H | Bt | Bt | Ph3 | 1 | 2 | $Mn^{2+}$ |
| 368 | Et | Et | Me | H | Me | H | H | Bt | Bt | Ph3 | 1 | 2 | $Mn^{2+}$ |
| 369 | Bt | Bt | Me | H | Me | H | H | Bt | Bt | Ph3 | 1 | 2 | $Mn^{2+}$ |
| 370 | Et | Et | Me | Me | Me | Me | H | Bt | Bt | Ph3 | 1 | 2 | $Mn^{2+}$ |
| 371 | Bt | Bt | Me | Me | Me | Me | H | Bt | Bt | Ph3 | 1 | 2 | $Mn^{2+}$ |
| 372 | Et | Et | iPr | H | iPr | H | H | Bt | Bt | Ph3 | 1 | 2 | $Mn^{2+}$ |
| 373 | Bt | Bt | iPr | H | iPr | H | H | Bt | Bt | Ph3 | 1 | 2 | $Mn^{2+}$ |
| 374 | Et | Et | iPr | iPr | iPr | iPr | H | Bt | Bt | Ph3 | 1 | 2 | $Mn^{2+}$ |
| 375 | Bt | Bt | iPr | iPr | iPr | iPr | H | Bt | Bt | Ph3 | 1 | 2 | $Mn^{2+}$ |
| 376 | Et | Et | F | H | F | H | H | Bt | Bt | Ph3 | 1 | 2 | $Mn^{2+}$ |
| 377 | Bt | Bt | F | H | F | H | H | Bt | Bt | Ph3 | 1 | 2 | $Mn^{2+}$ |
| 378 | Et | Et | F | F | F | F | H | Bt | Bt | Ph3 | 1 | 2 | $Mn^{2+}$ |
| 379 | Bt | Bt | F | F | F | F | H | Bt | Bt | Ph3 | 1 | 2 | $Mn^{2+}$ |
| 380 | Me | Me | H | H | H | H | H | Et | Ph2 | Ph3 | 1 | 2 | $Mn^{2+}$ |
| 381 | Et | Et | H | H | H | H | H | Et | Ph2 | Ph3 | 1 | 2 | $Mn^{2+}$ |
| 382 | Bt | Bt | H | H | H | H | H | Et | Ph2 | Ph3 | 1 | 2 | $Mn^{2+}$ |
| 383 | Et | Et | Me | H | Me | H | H | Et | Ph2 | Ph3 | 1 | 2 | $Mn^{2+}$ |
| 384 | Bt | Bt | Me | H | Me | H | H | Et | Ph2 | Ph3 | 1 | 2 | $Mn^{2+}$ |
| 385 | Et | Et | Me | Me | Me | Me | H | Et | Ph2 | Ph3 | 1 | 2 | $Mn^{2+}$ |
| 386 | Bt | Bt | Me | Me | Me | Me | H | Et | Ph2 | Ph3 | 1 | 2 | $Mn^{2+}$ |
| 387 | Et | Et | iPr | H | iPr | H | H | Et | Ph2 | Ph3 | 1 | 2 | $Mn^{2+}$ |
| 388 | Bt | Bt | iPr | H | iPr | H | H | Et | Ph2 | Ph3 | 1 | 2 | $Mn^{2+}$ |
| 389 | Et | Et | iPr | iPr | iPr | iPr | H | Et | Ph2 | Ph3 | 1 | 2 | $Mn^{2+}$ |
| 390 | Bt | Bt | iPr | iPr | iPr | iPr | H | Et | Ph2 | Ph3 | 1 | 2 | $Mn^{2+}$ |
| 391 | Et | Et | F | H | F | H | H | Et | Ph2 | Ph3 | 1 | 2 | $Mn^{2+}$ |
| 392 | Bt | Bt | F | H | F | H | H | Et | Ph2 | Ph3 | 1 | 2 | $Mn^{2+}$ |
| 393 | Et | Et | F | F | F | F | H | Et | Ph2 | Ph3 | 1 | 2 | $Mn^{2+}$ |
| 394 | Bt | Bt | F | F | F | F | H | Et | Ph2 | Ph3 | 1 | 2 | $Mn^{2+}$ |

TABLE 8

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 395 | Me | Me | H | H | H | H | H | Et | Ph2 | Ph4 | 1 | 2 | $Mn^{2+}$ |
| 396 | Et | Et | H | H | H | H | H | Et | Ph2 | Ph4 | 1 | 2 | $Mn^{2+}$ |
| 397 | Bt | Bt | H | H | H | H | H | Et | Ph2 | Ph4 | 1 | 2 | $Mn^{2+}$ |
| 398 | Et | Et | Me | H | Me | H | H | Et | Ph2 | Ph4 | 1 | 2 | $Mn^{2+}$ |
| 399 | Bt | Bt | Me | H | Me | H | H | Et | Ph2 | Ph4 | 1 | 2 | $Mn^{2+}$ |
| 400 | Et | Et | Me | Me | Me | Me | H | Et | Ph2 | Ph4 | 1 | 2 | $Mn^{2+}$ |
| 401 | Bt | Bt | Me | Me | Me | Me | H | Et | Ph2 | Ph4 | 1 | 2 | $Mn^{2+}$ |
| 402 | Et | Et | iPr | H | iPr | H | H | Et | Ph2 | Ph4 | 1 | 2 | $Mn^{2+}$ |
| 403 | Bt | Bt | iPr | H | iPr | H | H | Et | Ph2 | Ph4 | 1 | 2 | $Mn^{2+}$ |
| 404 | Et | Et | iPr | iPr | iPr | iPr | H | Et | Ph2 | Ph4 | 1 | 2 | $Mn^{2+}$ |
| 405 | Bt | Bt | iPr | iPr | iPr | iPr | H | Et | Ph2 | Ph4 | 1 | 2 | $Mn^{2+}$ |
| 406 | Et | Et | F | H | F | H | H | Et | Ph2 | Ph4 | 1 | 2 | $Mn^{2+}$ |
| 407 | Bt | Bt | F | H | F | H | H | Et | Ph2 | Ph4 | 1 | 2 | $Mn^{2+}$ |
| 408 | Et | Et | F | F | F | F | H | Et | Ph2 | Ph4 | 1 | 2 | $Mn^{2+}$ |
| 409 | Bt | Bt | F | F | F | F | H | Et | Ph2 | Ph4 | 1 | 2 | $Mn^{2+}$ |
| 410 | Me | Me | H | H | H | H | H | Et | Ph2 | Ph5 | 1 | 2 | $Mn^{2+}$ |
| 411 | Et | Et | H | H | H | H | H | Et | Ph2 | Ph5 | 1 | 2 | $Mn^{2+}$ |
| 412 | Bt | Bt | H | H | H | H | H | Et | Ph2 | Ph5 | 1 | 2 | $Mn^{2+}$ |
| 413 | Et | Et | Me | H | Me | H | H | Et | Ph2 | Ph5 | 1 | 2 | $Mn^{2+}$ |
| 414 | Bt | Bt | Me | H | Me | H | H | Et | Ph2 | Ph5 | 1 | 2 | $Mn^{2+}$ |
| 415 | Et | Et | Me | Me | Me | Me | H | Et | Ph2 | Ph5 | 1 | 2 | $Mn^{2+}$ |
| 416 | Bt | Bt | Me | Me | Me | Me | H | Et | Ph2 | Ph5 | 1 | 2 | $Mn^{2+}$ |
| 417 | Et | Et | iPr | H | iPr | H | H | Et | Ph2 | Ph5 | 1 | 2 | $Mn^{2+}$ |
| 418 | Bt | Bt | iPr | H | iPr | H | H | Et | Ph2 | Ph5 | 1 | 2 | $Mn^{2+}$ |
| 419 | Et | Et | iPr | iPr | iPr | iPr | H | Et | Ph2 | Ph5 | 1 | 2 | $Mn^{2+}$ |
| 420 | Bt | Bt | iPr | iPr | iPr | iPr | H | Et | Ph2 | Ph5 | 1 | 2 | $Mn^{2+}$ |
| 421 | Et | Et | F | H | F | H | H | Et | Ph2 | Ph5 | 1 | 2 | $Mn^{2+}$ |
| 422 | Bt | Bt | F | H | F | H | H | Et | Ph2 | Ph5 | 1 | 2 | $Mn^{2+}$ |
| 423 | Et | Et | F | F | F | F | H | Et | Ph2 | Ph5 | 1 | 2 | $Mn^{2+}$ |
| 424 | Bt | Bt | F | F | F | F | H | Et | Ph2 | Ph5 | 1 | 2 | $Mn^{2+}$ |
| 425 | Me | Me | H | H | H | H | H | Bt | Bt | Ph1 | 1 | 2 | $Sr^{2+}$ |
| 426 | Et | Et | H | H | H | H | H | Bt | Bt | Ph1 | 1 | 2 | $Sr^{2+}$ |
| 427 | Bt | Bt | H | H | H | H | H | Bt | Bt | Ph1 | 1 | 2 | $Sr^{2+}$ |
| 428 | Et | Et | Me | H | Me | H | H | Bt | Bt | Ph1 | 1 | 2 | $Sr^{2+}$ |
| 429 | Bt | Bt | Me | H | Me | H | H | Bt | Bt | Ph1 | 1 | 2 | $Sr^{2+}$ |
| 430 | Et | Et | Me | Me | Me | Me | H | Bt | Bt | Ph1 | 1 | 2 | $Sr^{2+}$ |
| 431 | Bt | Bt | Me | Me | Me | Me | H | Bt | Bt | Ph1 | 1 | 2 | $Sr^{2+}$ |
| 432 | Et | Et | iPr | H | iPr | H | H | Bt | Bt | Ph1 | 1 | 2 | $Sr^{2+}$ |
| 433 | Bt | Bt | iPr | H | iPr | H | H | Bt | Bt | Ph1 | 1 | 2 | $Sr^{2+}$ |
| 434 | Et | Et | iPr | iPr | iPr | iPr | H | Bt | Bt | Ph1 | 1 | 2 | $Sr^{2+}$ |
| 435 | Bt | Bt | iPr | iPr | iPr | iPr | H | Bt | Bt | Ph1 | 1 | 2 | $Sr^{2+}$ |
| 436 | Et | Et | F | H | F | H | H | Bt | Bt | Ph1 | 1 | 2 | $Sr^{2+}$ |
| 437 | Bt | Bt | F | H | F | H | H | Bt | Bt | Ph1 | 1 | 2 | $Sr^{2+}$ |
| 438 | Et | Et | F | F | F | F | H | Bt | Bt | Ph1 | 1 | 2 | $Sr^{2+}$ |
| 439 | Bt | Bt | F | F | F | F | H | Bt | Bt | Ph1 | 1 | 2 | $Sr^{2+}$ |
| 440 | Me | Me | H | H | H | H | H | Et | Ph2 | Ph1 | 1 | 2 | $Sr^{2+}$ |
| 441 | Et | Et | H | H | H | H | H | Et | Ph2 | Ph1 | 1 | 2 | $Sr^{2+}$ |
| 442 | Bt | Bt | H | H | H | H | H | Et | Ph2 | Ph1 | 1 | 2 | $Sr^{2+}$ |
| 443 | Et | Et | Me | H | Me | H | H | Et | Ph2 | Ph1 | 1 | 2 | $Sr^{2+}$ |
| 444 | Bt | Bt | Me | H | Me | H | H | Et | Ph2 | Ph1 | 1 | 2 | $Sr^{2+}$ |
| 445 | Et | Et | Me | Me | Me | Me | H | Et | Ph2 | Ph1 | 1 | 2 | $Sr^{2+}$ |
| 446 | Bt | Bt | Me | Me | Me | Me | H | Et | Ph2 | Ph1 | 1 | 2 | $Sr^{2+}$ |
| 447 | Et | Et | iPr | H | iPr | H | H | Et | Ph2 | Ph1 | 1 | 2 | $Sr^{2+}$ |
| 448 | Bt | Bt | iPr | H | iPr | H | H | Et | Ph2 | Ph1 | 1 | 2 | $Sr^{2+}$ |
| 449 | Et | Et | iPr | iPr | iPr | iPr | H | Et | Ph2 | Ph1 | 1 | 2 | $Sr^{2+}$ |
| 450 | Bt | Bt | iPr | iPr | iPr | iPr | H | Et | Ph2 | Ph1 | 1 | 2 | $Sr^{2+}$ |
| 451 | Et | Et | F | H | F | H | H | Et | Ph2 | Ph1 | 1 | 2 | $Sr^{2+}$ |
| 452 | Bt | Bt | F | H | F | H | H | Et | Ph2 | Ph1 | 1 | 2 | $Sr^{2+}$ |
| 453 | Et | Et | F | F | F | F | H | Et | Ph2 | Ph1 | 1 | 2 | $Sr^{2+}$ |
| 454 | Bt | Bt | F | F | F | F | H | Et | Ph2 | Ph1 | 1 | 2 | $Sr^{2+}$ |

TABLE 9

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 455 | Me | Me | H | H | H | H | H | Bt | Bt | Ph3 | 1 | 2 | $Sr^{2+}$ |
| 456 | Et | Et | H | H | H | H | H | Bt | Bt | Ph3 | 1 | 2 | $Sr^{2+}$ |
| 457 | Bt | Bt | H | H | H | H | H | Bt | Bt | Ph3 | 1 | 2 | $Sr^{2+}$ |
| 458 | Et | Et | Me | H | Me | H | H | Bt | Bt | Ph3 | 1 | 2 | $Sr^{2+}$ |
| 459 | Bt | Bt | Me | H | Me | H | H | Bt | Bt | Ph3 | 1 | 2 | $Sr^{2+}$ |
| 460 | Et | Et | Me | Me | Me | Me | H | Bt | Bt | Ph3 | 1 | 2 | $Sr^{2+}$ |
| 461 | Bt | Bt | Me | Me | Me | Me | H | Bt | Bt | Ph3 | 1 | 2 | $Sr^{2+}$ |
| 462 | Et | Et | iPr | H | iPr | H | H | Bt | Bt | Ph3 | 1 | 2 | $Sr^{2+}$ |
| 463 | Bt | Bt | iPr | H | iPr | H | H | Bt | Bt | Ph3 | 1 | 2 | $Sr^{2+}$ |
| 464 | Et | Et | iPr | iPr | iPr | iPr | H | Bt | Bt | Ph3 | 1 | 2 | $Sr^{2+}$ |

TABLE 9-continued

| | $R^{41}$ | $R^{43}$ | $R^{11A}$ | $R^{12A}$ | $R^{13A}$ | $R^{14A}$ | $R^h$ | $R^{45}$ | $R^{46}$ | $R^{55}$ | k-1 | r | $M^{r+}$ |
|---|---|---|---|---|---|---|---|---|---|---|---|---|---|
| 465 | Bt | Bt | iPr | iPr | iPr | iPr | H | Bt | Bt | Ph3 | 1 | 2 | $Sr^{2+}$ |
| 466 | Et | Et | F | H | F | H | H | Bt | Bt | Ph3 | 1 | 2 | $Sr^{2+}$ |
| 467 | Bt | Bt | F | H | F | H | H | Bt | Bt | Ph3 | 1 | 2 | $Sr^{2+}$ |
| 468 | Et | Et | F | F | F | F | H | Bt | Bt | Ph3 | 1 | 2 | $Sr^{2+}$ |
| 469 | Bt | Bt | F | F | F | F | H | Bt | Bt | Ph3 | 1 | 2 | $Sr^{2+}$ |
| 470 | Me | Me | H | H | H | H | H | Et | Ph2 | Ph3 | 1 | 2 | $Sr^{2+}$ |
| 471 | Et | Et | H | H | H | H | H | Et | Ph2 | Ph3 | 1 | 2 | $Sr^{2+}$ |
| 472 | Bt | Bt | H | H | H | H | H | Et | Ph2 | Ph3 | 1 | 2 | $Sr^{2+}$ |
| 473 | Et | Et | Me | H | Me | H | H | Et | Ph2 | Ph3 | 1 | 2 | $Sr^{2+}$ |
| 474 | Bt | Bt | Me | H | Me | H | H | Et | Ph2 | Ph3 | 1 | 2 | $Sr^{2+}$ |
| 475 | Et | Et | Me | Me | Me | Me | H | Et | Ph2 | Ph3 | 1 | 2 | $Sr^{2+}$ |
| 476 | Bt | Bt | Me | Me | Me | Me | H | Et | Ph2 | Ph3 | 1 | 2 | $Sr^{2+}$ |
| 477 | Et | Et | iPr | H | iPr | H | H | Et | Ph2 | Ph3 | 1 | 2 | $Sr^{2+}$ |
| 478 | Bt | Bt | iPr | H | iPr | H | H | Et | Ph2 | Ph3 | 1 | 2 | $Sr^{2+}$ |
| 479 | Et | Et | iPr | iPr | iPr | iPr | H | Et | Ph2 | Ph3 | 1 | 2 | $Sr^{2+}$ |
| 480 | Bt | Bt | iPr | iPr | iPr | iPr | H | Et | Ph2 | Ph3 | 1 | 2 | $Sr^{2+}$ |
| 481 | Et | Et | F | H | F | H | H | Et | Ph2 | Ph3 | 1 | 2 | $Sr^{2+}$ |
| 482 | Bt | Bt | F | H | F | H | H | Et | Ph2 | Ph3 | 1 | 2 | $Sr^{2+}$ |
| 483 | Et | Et | F | F | F | F | H | Et | Ph2 | Ph3 | 1 | 2 | $Sr^{2+}$ |
| 484 | Bt | Bt | F | F | F | F | H | Et | Ph2 | Ph3 | 1 | 2 | $Sr^{2+}$ |
| 485 | Me | Me | H | H | H | H | H | Et | Ph2 | Ph4 | 1 | 2 | $Sr^{2+}$ |
| 486 | Et | Et | H | H | H | H | H | Et | Ph2 | Ph4 | 1 | 2 | $Sr^{2+}$ |
| 487 | Bt | Bt | H | H | H | H | H | Et | Ph2 | Ph4 | 1 | 2 | $Sr^{2+}$ |
| 488 | Et | Et | Me | H | Me | H | H | Et | Ph2 | Ph4 | 1 | 2 | $Sr^{2+}$ |
| 489 | Bt | Bt | Me | H | Me | H | H | Et | Ph2 | Ph4 | 1 | 2 | $Sr^{2+}$ |
| 490 | Et | Et | Me | Me | Me | Me | H | Et | Ph2 | Ph4 | 1 | 2 | $Sr^{2+}$ |
| 491 | Bt | Bt | Me | Me | Me | Me | H | Et | Ph2 | Ph4 | 1 | 2 | $Sr^{2+}$ |
| 492 | Et | Et | iPr | H | iPr | H | H | Et | Ph2 | Ph4 | 1 | 2 | $Sr^{2+}$ |
| 493 | Bt | Bt | iPr | H | iPr | H | H | Et | Ph2 | Ph4 | 1 | 2 | $Sr^{2+}$ |
| 494 | Et | Et | iPr | iPr | iPr | iPr | H | Et | Ph2 | Ph4 | 1 | 2 | $Sr^{2+}$ |
| 495 | Bt | Bt | iPr | iPr | iPr | iPr | H | Et | Ph2 | Ph4 | 1 | 2 | $Sr^{2+}$ |
| 496 | Et | Et | F | H | F | H | H | Et | Ph2 | Ph4 | 1 | 2 | $Sr^{2+}$ |
| 497 | Bt | Bt | F | H | F | H | H | Et | Ph2 | Ph4 | 1 | 2 | $Sr^{2+}$ |
| 498 | Et | Et | F | F | F | F | H | Et | Ph2 | Ph4 | 1 | 2 | $Sr^{2+}$ |
| 499 | Bt | Bt | F | F | F | F | H | Et | Ph2 | Ph4 | 1 | 2 | $Sr^{2+}$ |
| 500 | Me | Me | H | H | H | H | H | Et | Ph2 | Ph5 | 1 | 2 | $Sr^{2+}$ |
| 501 | Et | Et | H | H | H | H | H | Et | Ph2 | Ph5 | 1 | 2 | $Sr^{2+}$ |
| 502 | Bt | Bt | H | H | H | H | H | Et | Ph2 | Ph5 | 1 | 2 | $Sr^{2+}$ |
| 503 | Et | Et | Me | H | Me | H | H | Et | Ph2 | Ph5 | 1 | 2 | $Sr^{2+}$ |
| 504 | Bt | Bt | Me | H | Me | H | H | Et | Ph2 | Ph5 | 1 | 2 | $Sr^{2+}$ |
| 505 | Et | Et | Me | Me | Me | Me | H | Et | Ph2 | Ph5 | 1 | 2 | $Sr^{2+}$ |
| 506 | Bt | Bt | Me | Me | Me | Me | H | Et | Ph2 | Ph5 | 1 | 2 | $Sr^{2+}$ |
| 507 | Et | Et | iPr | H | iPr | H | H | Et | Ph2 | Ph5 | 1 | 2 | $Sr^{2+}$ |
| 508 | Bt | Bt | iPr | H | iPr | H | H | Et | Ph2 | Ph5 | 1 | 2 | $Sr^{2+}$ |
| 509 | Et | Et | iPr | iPr | iPr | iPr | H | Et | Ph2 | Ph5 | 1 | 2 | $Sr^{2+}$ |
| 510 | Bt | Bt | iPr | iPr | iPr | iPr | H | Et | Ph2 | Ph5 | 1 | 2 | $Sr^{2+}$ |
| 511 | Et | Et | F | H | F | H | H | Et | Ph2 | Ph5 | 1 | 2 | $Sr^{2+}$ |
| 512 | Bt | Bt | F | H | F | H | H | Et | Ph2 | Ph5 | 1 | 2 | $Sr^{2+}$ |
| 513 | Et | Et | F | F | F | F | H | Et | Ph2 | Ph5 | 1 | 2 | $Sr^{2+}$ |
| 514 | Bt | Bt | F | F | F | F | H | Et | Ph2 | Ph5 | 1 | 2 | $Sr^{2+}$ |

In Tables 1 to 9, Me represents a methyl group; Et represents an ethyl group; iPr represents an isopropyl group; Bt represents a n-butyl group; and Ph1 to Ph10 represent groups represented by the following formulas. In Ph1 to Ph10, * represents a point of attachment.

[Formula 16]

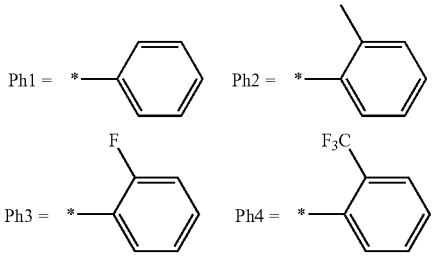

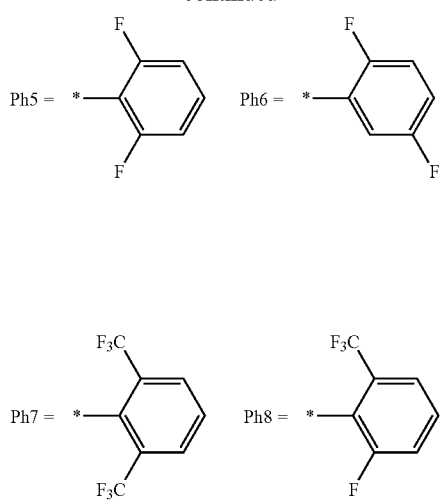

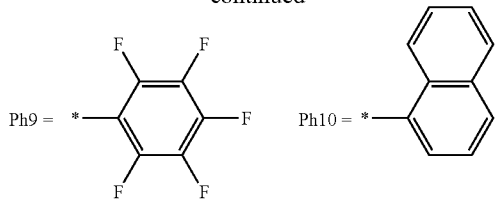

Among these, the compound (1)

is preferably compounds 31 to 90, compounds 121 to 180, compounds 211 to 334, compounds 365 to 424, and compounds 455 to 514, more preferably compounds 46 to 60, compounds 61 to 90, compounds 136 to 150, compounds 226 to 240, compounds 271 to 334, compounds 380 to 394, and compounds 470 to 484, still more preferably compounds 46 to 60, compounds 61 to 90, compounds 136 to 150, compounds 226 to 240, compounds 271 to 304, compounds 380 to 394, and compounds 470 to 484, yet still more preferably compounds 46 to 60, compounds 61 to 90, compounds 136 to 150, compounds 226 to 240, compounds 271 to 294, compounds 380 to 394, and compounds 470 to 484, and particularly preferably compounds 46 to 60, compounds 61 to 90, compounds 136 to 150, compounds 226 to 240, compounds 279 to 294, compounds 380 to 394, and compounds 470 to 484.

These compounds particularly achieve both high heat resistance and high light resistance, and provide a good brightness.

The compound (1) having $-SO_3^-$ can be produced by, for example, sulfonating a compound represented by formula (IC) (hereinafter, sometimes referred to as compound (IC)), and then reacting the sulfonated product with a halide (preferably chloride), acetate, phosphate, sulfate, silicate, cyanide or the like containing an r-valent metal ion:

[Formula 17]

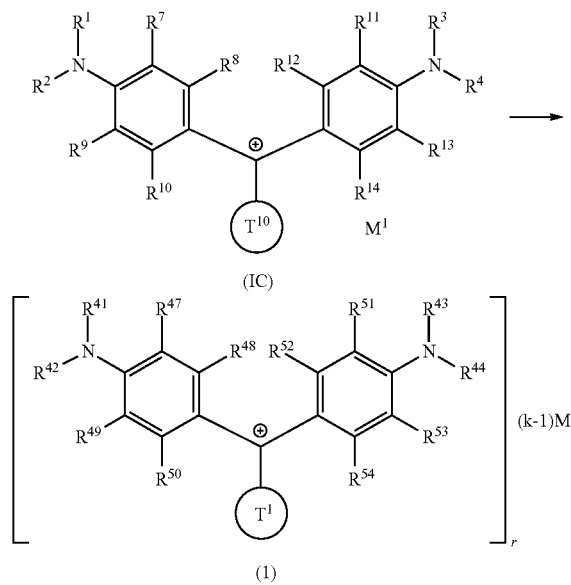

wherein $R^1$ to $R^4$ each independently represent a hydrogen atom, a saturated hydrocarbon group having 1 to 20 carbon atoms, an aromatic hydrocarbon group having 6 to 20 carbon atoms and optionally having a substituent, or an aralkyl group having 7 to 30 carbon atoms and optionally having a substituent; in the saturated hydrocarbon group having 1 to 20 carbon atoms, a hydrogen atom contained in the saturated hydrocarbon group is optionally replaced with a substituted or unsubstituted amino group or a halogen atom; $-CH_2-$ contained in the saturated hydrocarbon group is optionally replaced with at least one of $-O-$ and $-CO-$; $R^1$ and $R^2$ are optionally bonded to each other to form a ring together with a nitrogen atom to which they are attached; and $R^3$ and $R^4$ are optionally bonded to each other to form a ring together with a nitrogen atom to which they are attached;

$R^7$ to $R^{14}$ each independently represent a hydrogen atom, a halogen atom, a nitro group, a hydroxy group, or an alkyl group having 1 to 8 carbon atoms; $-CH_2-$ constituting the alkyl group is optionally replaced with at least one of $-O-$ and $-CO-$; $R^8$ and $R^{12}$ are optionally bonded to each other to form $-NH-$, $-S-$, or $-SO_2^-$;

a ring $T^{10}$ represents an aromatic heterocycle having 3 to 10 carbon atoms; and the aromatic heterocycle optionally has a saturated hydrocarbon group having 1 to 20 carbon atoms, or an aromatic hydrocarbon group having 6 to 20 carbon atoms and optionally having a substituent;

and $M^1$ represents $Cl^-$, a phosphate ion, a perchlorate ion, $BF_4^-$, or $PF_6^-$.

The compound (1) having $-SO_2-N^--SO_2-R^f$ can be produced by reacting a compound (1) which has a $-SO_3^-$ group and does not have $-SO_2-N^--SO_2-R^f$ with a compound represented by formula (IB), and then reacting the reaction product with a halide (preferably chloride), acetate, phosphate, sulfate, silicate, cyanide or the like containing an r-valent metal ion:

[Formula 18]

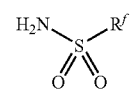

wherein $R^f$ is the same as above.

Examples of the sulfonation method include various known techniques, for example, a technique described in Journal of Organic Chemistry, (1994), vol. 59, #11, p. 3232-3236.

The copper phthalocyanine pigment contained as the colorant is preferably represented by formula (2).

[Formula 19]

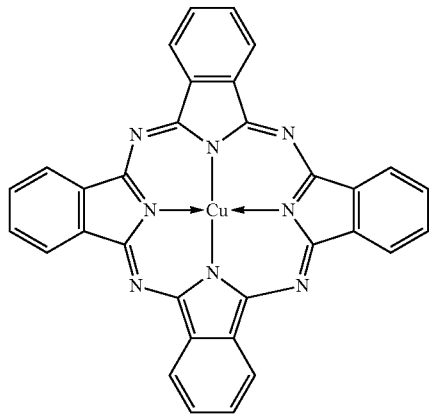

(2)

As the α-type and/or β-type copper phthalocyanine pigment, α-type copper phthalocyanine pigments such as C.I. Pigment blue 15, C.I. Pigment blue 15:1, and C.I. Pigment blue 15:2; and β-type copper phthalocyanine pigments such as C.I. Pigment blue 15:3 and C.I. Pigment blue 15:4 are preferably exemplified, and more preferably C.I. Pigment blue 15 or C.I. Pigment blue 15:3. The α-type and/or β-type copper phthalocyanine pigments may be used singly or in combinations of a plurality thereof.

A dispersant is added to the compound (1) and the α-type and/or β-type copper phthalocyanine pigment, followed by performing a dispersion treatment, whereby a dispersion in which the compound (1) and the copper phthalocyanine pigments are uniformly dispersed in a solution can be produced.

Examples of the dispersant include surfactants such as cationic, anionic, non-ionic, amphoteric, polyester-based, polyamine-based, and acrylic surfactants. These dispersants may be used singly or in combinations of two or more thereof. Examples of the dispersant include KP (trade name) (manufactured by Shin-Etsu Chemical Co., Ltd.), Flowlen (manufactured by Kyoeisha Chemical Co., Ltd.), Solsperse (manufactured by Zeneca Ltd.), EFKA (manufactured by CIBA Corporation), AJISPER (manufactured by Ajinomoto Fine-Techno Co., Inc.), and Disperbyk (manufactured by BYK-Chemie Corporation). As the other dispersant, a resin (B) to be described later (preferably resin [K1]) may be used.

When the dispersant is used, the amount of the dispersant used is preferably 1% by mass or more and 100% by mass or less, and more preferably 15% by mass or more and 100% by mass or less, relative to the whole amount of the colorant. When the amount of the dispersant used falls within the above-mentioned range, there is a tendency that a dispersion having a uniform dispersion state is obtained.

The colorant (A) may contain one or both of other dye (hereinafter, sometimes referred to as dye (A1)) and other pigment (hereinafter, sometimes referred to as pigment (A2)) in addition to the compound (1) and the α-type and/or β-type copper phthalocyanine pigment.

The dye (A1) is not particularly limited, and any known dye can be used. Examples of the dye include a solvent dye, an acid dye, a direct dye, and a mordant dye. Examples of the dye include a compound which is not a pigment but classified into a compound having a hue in the Color Index (published by The Society of Dyers and Colourists), and a known dye as described in Dying note (Shikisensha Co., Ltd.). According to chemical structures, it includes an azo dye, a cyanine dye, a triphenylmethane dye, a xanthene dye, a phthalocyanine dye, an anthraquinone dye, a naphthoquinone dye, a quinonimine dye, a methine dye, an azomethine dye, a squarylium dye, an acridine dye, a styryl dye, a coumarin dye, a quinoline dye, and a nitro dye. Among these, a dye which is soluble in an organic solvent is preferable.

Specific examples include
C. I. Solvent dyes such as:
C. I. Solvent Yellows 4 (hereinafter, the term "C. I. Solvent Yellow" is omitted and only the number is described), 14, 15, 23, 24, 38, 62, 63, 68, 82, 94, 98, 99, 117, 162, 163, 167, and 189;
C. I. Solvent Reds 45, 49, 111, 125, 130, 143, 145, 146, 150, 151, 155, 168, 169, 172, 175, 181, 207, 218, 222, 227, 230, 245, 247;
C. I. Solvent Oranges 2, 7, 11, 15, 26, 56, 77, and 86;
C. I. Solvent Violets 11, 13, 14, 26, 31, 36, 37, 38, 45, 47, 48, 51, 59, and 60;
C. I. Solvent Blues 4, 5, 14, 18, 35, 36, 37, 45, 58, 59, 59:1, 63, 67, 68, 69, 70, 78, 79, 83, 90, 94, 97, 98, 100, 101, 102, 104, 105, 111, 112, 122, 128, 132, 136, 139;
C. I. Solvent Greens 1, 3, 4, 5, 7, 28, 29, 32, 33, 34, and 35,
C. I. Acid dyes such as:
C. I. Acid Yellows 1, 3, 7, 9, 11, 17, 23, 25, 29, 34, 36, 38, 40, 42, 54, 65, 72, 73, 76, 79, 98, 99, 111, 112, 113, 114, 116, 119, 123, 128, 134, 135, 138, 139, 140, 144, 150, 155, 157, 160, 161, 163, 168, 169, 172, 177, 178, 179, 184, 190, 193, 196, 197, 199, 202, 203, 204, 205, 207, 212, 214, 220, 221, 228, 230, 232, 235, 238, 240, 242, 243, 251;
C. I. Acid Reds 1, 4, 8, 14, 17, 18, 26, 27, 29, 31, 33, 34, 35, 37, 40, 42, 44, 50, 51, 52, 57, 66, 73, 76, 80, 87, 88, 91, 92, 94, 95, 97, 98, 103, 106, 111, 114, 129, 133, 134, 138, 143, 145, 150, 151, 155, 158, 160, 172, 176, 182, 183, 195, 198, 206, 211, 215, 216, 217, 227, 228, 249, 252, 257, 258, 260, 261, 266, 268, 270, 274, 277, 280, 281, 289, 308, 312, 315, 316, 339, 341, 345, 346, 349, 382, 383, 388, 394, 401, 412, 417, 418, 422, 426;
C. I. Acid Oranges 6, 7, 8, 10, 12, 26, 50, 51, 52, 56, 62, 63, 64, 74, 75, 94, 95, 107, 108, 169, and 173;
C. I. Acid Violets 6B, 7, 9, 15, 16, 17, 19, 21, 23, 24, 25, 30, 34, 38, 49, 72, 102;
C.I. acid blue 1, 3, 5, 7, 9, 11, 13, 15, 17, 18, 22, 23, 24, 25, 26, 27, 29, 34, 38, 40, 41, 42, 43, 45, 48, 51, 54, 59, 60, 62, 70, 72, 74, 75, 78, 80, 82, 83, 86, 87, 88, 90, 90:1, 91, 92, 93, 93:1, 96, 99, 100, 102, 103, 104, 108, 109, 110, 112, 113, 117, 119, 120, 123, 126, 127, 129, 130, 131, 138, 140, 142, 143, 147, 150, 151, 154, 158, 161, 166, 167, 168, 170, 171, 175, 182, 183, 184, 187, 192, 199, 203, 204, 205, 210, 213, 229, 234, 236, 242, 243, 256, 259, 267, 269, 278, 280, 285, 290, 296, 315, 324:1, 335, 340;
C. I. Acid Greens 1, 3, 5, 6, 7, 8, 9, 11, 13, 14, 15, 16, 22, 25, 27, 28, 41, 50, 50:1, 58, 63, 65, 80, 104, 105, 106, and 109,
C. I. Direct dyes such as:
C. I. Direct Yellows 2, 33, 34, 35, 38, 39, 43, 47, 50, 54, 58, 68, 69, 70, 71, 86, 93, 94, 95, 98, 102, 108, 109, 129, 136, 138, 141;
C. I. Direct Reds 79, 82, 83, 84, 91, 92, 96, 97, 98, 99, 105, 106, 107, 172, 173, 176, 177, 179, 181, 182, 184, 204, 207, 211, 213, 218, 220, 221, 222, 232, 233, 234, 241, 243, 246, 250;

C. I. Direct Oranges 26, 34, 39, 41, 46, 50, 52, 56, 57, 61, 64, 65, 68, 70, 96, 97, 106, and 107;
C. I. Direct Violets 47, 52, 54, 59, 60, 65, 66, 79, 80, 81, 82, 84, 89, 90, 93, 95, 96, 103, and 104;
C. I. Direct Blues 1, 2, 3, 6, 8, 15, 22, 25, 28, 29, 40, 41, 42, 47, 52, 55, 57, 71, 76, 77, 78, 80, 81, 84, 85, 86, 90, 93, 94, 95, 97, 98, 99, 100, 101, 106, 107, 108, 109, 113, 114, 115, 117, 119, 120, 137, 149, 150, 153, 155, 156, 158, 159, 160, 161, 162, 163, 164, 165, 166, 167, 168, 170, 171, 172, 173, 188, 189, 190, 192, 193, 194, 195, 196, 198, 199, 200, 201, 202, 203, 207, 209, 210, 212, 213, 214, 222, 225, 226, 228, 229, 236, 237, 238, 242, 243, 244, 245, 246, 247, 248, 249, 250, 251, 252, 256, 257, 259, 260, 268, 274, 275, 293;
C. I. Direct Greens 25, 27, 31, 32, 34, 37, 63, 65, 66, 67, 68, 69, 72, 77, 79, and 82,
C. I. Disperse dyes such as:
C. I. Disperse Yellows 51, 54, and 76;
C. I. Disperse Violets 26 and 27;
C. I. Disperse Blues 1, 14, 56, and 60,
C. I. Basic dyes such as:
C. I. Basic Reds 1 and 10;
C. I. Basic Blues 1, 3, 5, 7, 9, 19, 21, 22, 24, 25, 26, 28, 29, 40, 41, 45, 47, 54, 58, 59, 60, 64, 65, 66, 67, 68, 81, 83, 88, and 89;
C. I. Basic Violet 2;
C. I. Basic Red 9;
C. I. Basic Green 1,
C. I. Reactive dyes such as:
C. I. Reactive Yellows 2, 76, and 116;
C. I. Reactive Orange 16;
C. I. Reactive Red 36,
C. I. Mordant dyes such as:
C. I. Mordant Yellows 5, 8, 10, 16, 20, 26, 30, 31, 33, 42, 43, 45, 56, 61, 62, and 65;
C. I. Mordant Reds 1, 2, 3, 4, 9, 11, 12, 14, 17, 18, 19, 22, 23, 24, 25, 26, 27, 29, 30, 32, 33, 36, 37, 38, 39, 41, 42, 43, 45, 46, 48, 52, 53, 56, 62, 63, 71, 74, 76, 78, 85, 86, 88, 90, 94, 95;
C. I. Mordant Oranges 3, 4, 5, 8, 12, 13, 14, 20, 21, 23, 24, 28, 29, 32, 34, 35, 36, 37, 42, 43, 47, and 48;
C. I. Mordant Violets 1, 1:1, 2, 3, 4, 5, 6, 7, 8, 10, 11, 14, 15, 16, 17, 18, 19, 21, 22, 23, 24, 27, 28, 30, 31, 32, 33, 36, 37, 39, 40, 41, 44, 45, 47, 48, 49, 53, 58;
C. I. Mordant Blues 1, 2, 3, 7, 8, 9, 12, 13, 15, 16, 19, 20, 21, 22, 23, 24, 26, 30, 31, 32, 39, 40, 41, 43, 44, 48, 49, 53, 61, 74, 77, 83, 84;
C. I. Mordant Greens 1, 3, 4, 5, 10, 13, 15, 19, 21, 23, 26, 29, 31, 33, 34, 35, 41, 43, and 53; and
C. I. Vat dyes such as:
C. I. Vat Green 1.

These dyes may be appropriately selected depending on the spectral spectrum of a desired color filter.

Known pigments can be used as the pigment (A2) without particular limitation. Examples thereof include a pigment which is classified into a pigment in the Color Index (published by The Society of Dyers and Colourists).

Examples of the pigment include yellow pigments such as C.I. Pigment Yellows 1, 3, 12, 13, 14, 15, 16, 17, 20, 24, 31, 53, 83, 86, 93, 94, 109, 110, 117, 125, 128, 137, 138, 139, 147, 148, 150, 153, 154, 166, 173, 194, and 214;
orange pigments such as C.I. Pigment Oranges 13, 31, 36, 38, 40, 42, 43, 51, 55, 59, 61, 64, 65, 71, and 73; red pigments such as C.I. Pigment Reds 9, 97, 105, 122, 123, 144, 149, 166, 168, 176, 177, 180, 192, 209, 215, 216, 224, 242, 254, 255, 264, and 265;
blue pigments such as C.I. Pigment Blues 15:6 and 60; violet pigments such as C.I. Pigment Violets 1, 19, 23, 29, 32, 36, and 38;
green pigments such as C.I. Pigment Greens 7, 36, and 58;
brown pigments such as C.I. Pigment Browns 23 and 25; and
black pigments such as C.I. Pigment Blacks 1 and 7.

These pigments may be subjected to a rosin treatment, a surface treatment using a pigment derivative or the like having an introduced acidic group or basic group, a pigment surface graft treatment with a polymeric compound or the like, a particle micronization treatment with a sulfuric acid micronization method or the like, a washing treatment with an organic solvent, water or the like for removing impurities, a removing treatment with an ionic exchange method or the like of ionic impurities or the like, if required.

The pigment preferably has a uniform particle diameter. A pigment dispersant is added, followed by performing a dispersion treatment, whereby a pigment dispersion in which the pigment is uniformly dispersed in a solution can be produced.

Examples of the pigment dispersant include surfactants such as cationic, anionic, non-ionic, amphoteric, polyester-based, polyamine-based, and acrylic surfactants. These pigment dispersants may be used singly or in combinations of two or more thereof. Examples of the pigment dispersant include KP (trade name) (manufactured by Shin-Etsu Chemical Co., Ltd.), Flowlen (manufactured by Kyoeisha Chemical Co., Ltd.), Solsperse (manufactured by Zeneca Ltd.), EFKA (manufactured by CIBA Corporation), AJIS-PER (manufactured by Ajinomoto Fine-Techno Co., Inc.), and Disperbyk (manufactured by BYK-Chemie Corporation).

When the pigment dispersant is used, the amount of the pigment dispersant used is preferably 1% by mass or more and 100% by mass or less, and more preferably 5% by mass or more and 50% by mass or less, relative to the whole amount of the pigment (A2). When the amount of the pigment dispersant used falls within the above-mentioned range, there is a tendency that the pigment dispersion having a uniform dispersion state is obtained.

The content ratio of the dye (A1) and pigment (A2) in the colorant (A) is commonly 1:99 to 99:1, preferably 5:95 to 95:5, and more preferably 10:90 to 90:10, on a mass basis.

The term "whole amount of solid content" as used herein means an amount obtained by excluding the content of the solvent from the whole amount of the colored photosensitive resin composition. The whole amount of the solid content and the content of each of the components with respect thereto can be measured by known analysis means such as liquid chromatography or gas chromatography.

The content rate of the compound (1) in the colored photosensitive resin composition of the present invention is preferably 10 to 99% by mass, more preferably 15 to 95% by mass, and still more preferably 20 to 90% by mass, in the whole amount of the colorant (A).

The content rate of the compound (1) is preferably 1 to 80% by mass, more preferably 1 to 70% by mass, and still more preferably 1 to 60% by mass, in the dispersion.

The content rate of the α-type and/or β-type copper phthalocyanine pigment in the colored photosensitive resin composition of the present invention is preferably 1% by mass or more, more preferably 5% by mass or more, and still more preferably 10% by mass or more, in 100% by mass of the colorant (A). The content rate is preferably 90% by mass or less, more preferably 85% by mass or less, and still more preferably 80% by mass or less.

As used herein, "the content rate (content) of the α-type and/or β-type copper phthalocyanine pigment" means the total content rate (content) of the α-type and β-type copper phthalocyanine pigments when both the α-type and β-type copper phthalocyanine pigments are contained as the copper phthalocyanine pigment, and the content rate (content) of the α-type copper phthalocyanine pigment or the content rate (content) of the β-type copper phthalocyanine pigment when any one of the α-type or β-type copper phthalocyanine pigment is contained as the copper phthalocyanine pigment.

In the colorant (A), the content ratio of the compound (1) and the α-type and/or β-type copper phthalocyanine pigment is commonly 1:99 to 99:1, preferably 5:95 to 95:5, more preferably 10:90 to 90:10, and still more preferably 20:80 to 90:10, on a mass basis.

The content rate of an ε-type copper phthalocyanine pigment in the colored photosensitive resin composition of the present invention is preferably 10% by mass or less, more preferably 5% by mass or less, still more preferably 1% by mass or less, yet still more preferably 0.5% by mass or less, and particularly preferably 0% by mass, in 100% by mass of the colorant (A). Examples of the 6-type copper phthalocyanine pigment include C.I. Pigment Blue 15:6.

The content rate of the 6-type copper phthalocyanine pigment is preferably 10% by mass or less, more preferably 5% by mass or less, still more preferably 1% by mass or less, yet still more preferably 0.5% by mass or less, and particularly preferably 0% by mass, relative to the total content rate of the α-type and/or β-type copper phthalocyanine pigment.

The content rate of the anthraquinone dye in the colored photosensitive resin composition of the present invention is preferably 20% by mass or less, more preferably 10% by mass or less, still more preferably 5% by mass or less, yet still more preferably 1% by mass or less, and particularly preferably 0% by mass, in 100% by mass of the colorant (A).

The content rate of the colorant (A) is preferably 5 to 60% by mass, more preferably 8 to 55% by mass, and still more preferably 10 to 50% by mass, relative to the whole amount of the solid content. When the content of the colorant (A) falls within the above-mentioned range, the color density of the color filter to be produced is sufficient, and necessary amounts of the resin (B) and polymerizable compound (C) can be contained in the composition, whereby a pattern having sufficient mechanical strength can be formed.

<Resin (B)>

The resin (B) is not particularly limited, and is preferably an alkali soluble resin. Examples of the resin (B) include the following resins [K1] to [K6].

Resin [K1]; a copolymer having a structural unit derived from at least one (a) selected from the group consisting of an unsaturated carboxylic acid and an unsaturated carboxylic anhydride (hereinafter, sometimes referred to as "(a)") and a structural unit derived from a monomer (b) having a cyclic ether structure having 2 to 4 carbon atoms and an ethylenically unsaturated bond (hereinafter, sometimes referred to as "(b)");

Resin [K2]; a copolymer having a structural unit derived from (a), a structural unit derived from (b), and a monomer (c) copolymerizable with (a) (provided that (c) is different from (a) and (b)) (hereinafter, sometimes referred to as "(c)");

Resin [K3]; a copolymer having a structural unit derived from (a) and a structural unit derived from (c);

Resin [K4]; a copolymer having a structural unit produced by adding (b) to a structural unit derived from (a) and a structural unit derived from (c);

Resin [K5]; a copolymer having a structural unit produced by adding (a) to a structural unit derived from (b) and a structural unit derived from (c); and Resin [K6]; a copolymer having a structural unit produced by adding (a) to a structural unit derived from (b) and further adding a carboxylic anhydride thereto and a structural unit derived from (c).

Specific examples of (a) include unsaturated monocarboxylic acids such as acrylic acid, methacrylic acid, crotonic acid, and o-, m- or p-vinylbenzoic acid;

unsaturated dicarboxylic acids such as maleic acid, fumaric acid, citraconic acid, mesaconic acid, itaconic acid, 3-vinylphthalic acid, 4-vinylphthalic acid, 3,4,5,6-tetrahydrophthalic acid, 1,2,3,6-tetrahydrophthalic acid, dimethyltetrahydrophthalic acid, and 1,4-cyclohexenedicarboxylic acid;

carboxy group-containing bicyclo unsaturated compounds such as methyl-5-norbornene-2,3-dicarboxylic acid, 5-carboxybicyclo[2.2.1]hept-2-ene, 5,6-dicarboxybicyclo[2.2.1]hept-2-ene, 5-carboxy-5-methylbicyclo[2.2.1]hept-2-ene, 5-carboxy-5-ethylbicyclo[2.2.1]hept-2-ene, 5-carboxy-6-methylbicyclo[2.2.1]hept-2-ene, and 5-carboxy-6-ethylbicyclo[2.2.1]hept-2-ene;

unsaturated dicarboxylic anhydrides such as maleic anhydride, citraconic anhydride, itaconic anhydride, 3-vinylphthalic anhydride, 4-vinylphthalic anhydride, 3,4,5,6-tetrahydrophthalic anhydride, 1,2,3,6-tetrahydrophthalic anhydride, dimethyltetrahydrophthalic anhydride, and 5,6-dicarboxybicyclo[2.2.1]hept-2-ene anhydride;

unsaturated mono[(meth)acryloyloxyalkyl]esters of a polyvalent carboxylic acid having a valence of 2 or more such as succinic acid mono[2-(meth)acryloyloxyethyl], and phthalic acid mono[2-(meth)acryloyloxyethyl]; and unsaturated acrylates containing a hydroxy group and a carboxy group in the same molecule such as α-(hydroxymethyl) acrylic acid.

Among these, from the viewpoint of copolymerization reactivity and solubility of a resin to be produced to an alkaline aqueous solution, acrylic acid, methacrylic acid, maleic anhydride and the like are preferable.

(b) means a polymerizable compound having, for example, a cyclic ether structure having 2 to 4 carbon atoms (for example, at least one selected from the group consisting of an oxirane ring, an oxetane ring, and a tetrahydrofuran ring) and an ethylenically unsaturated bond. (b) is preferably a monomer having a cyclic ether having 2 to 4 carbon atoms and a (meth)acryloyloxy group.

As used herein, "(meth)acrylic acid" represents at least one selected from the group consisting of acrylic acid and methacrylic acid. The terms "(meth)acryloyl", "(meth)acrylate" and the like also have similar meanings.

Examples of (b) include a monomer having an oxiranyl group and an ethylenically unsaturated bond (b1) (hereinafter, sometimes referred to as "(b1)"), a monomer having an oxetanyl group and an ethylenically unsaturated bond (b2) (hereinafter, sometimes referred to as "(b2)"), and a monomer having a tetrahydrofuryl group and an ethylenically unsaturated bond (b3) (hereinafter, sometimes referred to as "(b3)").

Examples of (b1) include a monomer having a structure where a linear or branched aliphatic unsaturated hydrocarbon is epoxidized (b1-1) (hereinafter, sometimes referred to as "(b1-1)") and a monomer having a structure where an alicyclic unsaturated hydrocarbon is epoxidized (b1-2) (hereinafter, sometimes referred to as "b1-2").

Examples of (b1-1) include glycidyl(meth)acrylate, β-methylglycidyl(meth)acrylate, β-ethylglycidyl(meth)

acrylate, glycidyl vinyl ether, o-vinylbenzyl glycidyl ether, m-vinylbenzyl glycidyl ether, p-vinylbenzyl glycidyl ether, α-methyl-o-vinylbenzyl glycidyl ether, α-methyl-m-vinylbenzyl glycidyl ether, α-methyl-p-vinylbenzyl glycidyl ether, 2,3-bis(glycidyloxymethyl)styrene, 2,4-bis(glycidyloxymethyl)styrene, 2,5-bis(glycidyloxymethyl)styrene, 2,6-bis(glycidyloxymethyl)styrene, 2,3,4-tris(glycidyloxymethyl)styrene, 2,3,5-tris(glycidyloxymethyl)styrene, 2,3,6-tris(glycidyloxymethyl)styrene, 3,4,5-tris(glycidyloxymethyl)styrene, and 2,4,6-tris(glycidyloxymethyl)styrene.

Examples of (b1-2) include vinylcyclohexene monoxide, 1,2-epoxy-4-vinylcyclohexane (for example, CELLOXIDE 2000; manufactured by Daicel Corporation), 3,4-epoxycyclohexylmethyl(meth)acrylate (for example, Cyclomer A400; manufactured by Daicel Corporation), 3,4-epoxycyclohexylmethyl(meth)acrylate (for example, Cyclomer M100; manufactured by Daicel Corporation), a compound represented by formula (I), and a compound represented by formula (II):

[Formula 20]

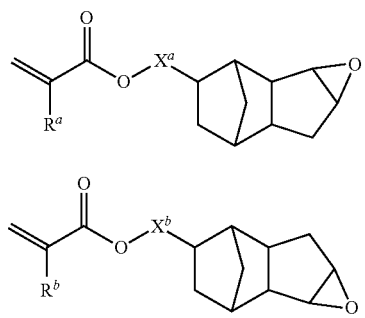

wherein
$R^a$ and $R^b$ represent a hydrogen atom or an alkyl group having 1 to 4 carbon atoms; the hydrogen atom contained in the alkyl group is optionally replaced with a hydroxy group;
$X^a$ and $X^b$ represent a single bond, *—$R^c$—, *—$R^c$—O—, *—$R^c$—S—, or *—$R^c$—NH—;
$R^c$ represents an alkanediyl group having 1 to 6 carbon atoms; and
* represents a point of attachment to O.

Examples of the alkyl group having 1 to 4 carbon atoms include a methyl group, an ethyl group, a n-propyl group, an isopropyl group, a n-butyl group, a sec-butyl group, and a tert-butyl group.

Examples of the alkyl group in which the hydrogen atom is replaced with the hydroxy group include a hydroxymethyl group, a 1-hydroxyethyl group, a 2-hydroxyethyl group, a 1-hydroxypropyl group, a 2-hydroxypropyl group, a 3-hydroxypropyl group, a 1-hydroxy-1-methylethyl group, a 2-hydroxy-1-methylethyl group, a 1-hydroxybutyl group, a 2-hydroxybutyl group, a 3-hydroxybutyl group, and a 4-hydroxybutyl group.

Preferably, examples of $R^a$ and $R^b$ include a hydrogen atom, a methyl group, a hydroxymethyl group, a 1-hydroxyethyl group, and a 2-hydroxyethyl group. More preferably, examples thereof include a hydrogen atom and a methyl group.

Examples of the alkanediyl group include a methylene group, an ethylene group, a propane-1,2-diyl group, a propane-1,3-diyl group, a butane-1,4-diyl group, a pentane-1,5-diyl group, and a hexane-1,6-diyl group.

Preferably, examples of $X^a$ and $X^b$ include a single bond, a methylene group, an ethylene group, *—$CH_2$—O—, and *—$CH_2CH_2$—O—. More preferably, examples thereof include a single bond and *—$CH_2CH_2$—O— (* represents a point of attachment to O).

Examples of the compound represented by formula (I) include a compound represented by any of formulas (I-1) to (I-15). Among these, the compound represented by formula (I-1), formula (I-3), formula (I-5), formula (I-7), formula (I-9), or formula (I-11) to formula (I-15) is preferable, and the compound represented by formula (I-1), formula (I-7), formula (I-9), or formula (I-15) is more preferable.

[Formula 21]

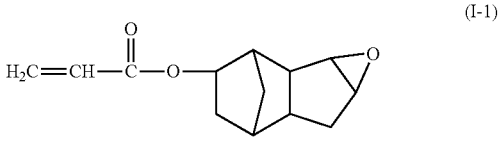

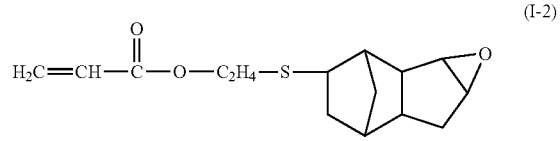

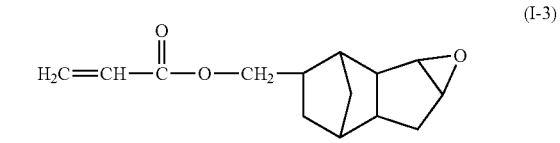

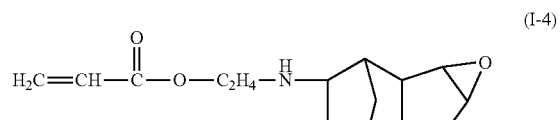

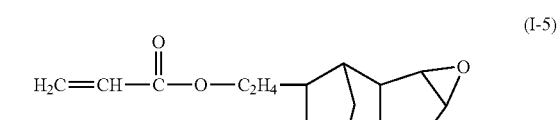

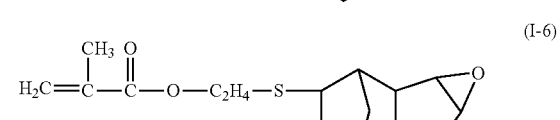

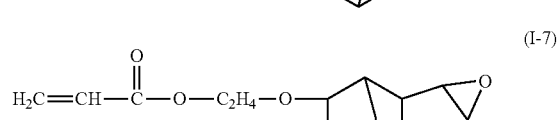

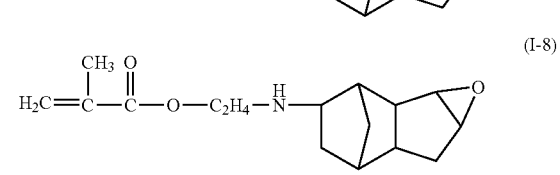

[Formula 22]

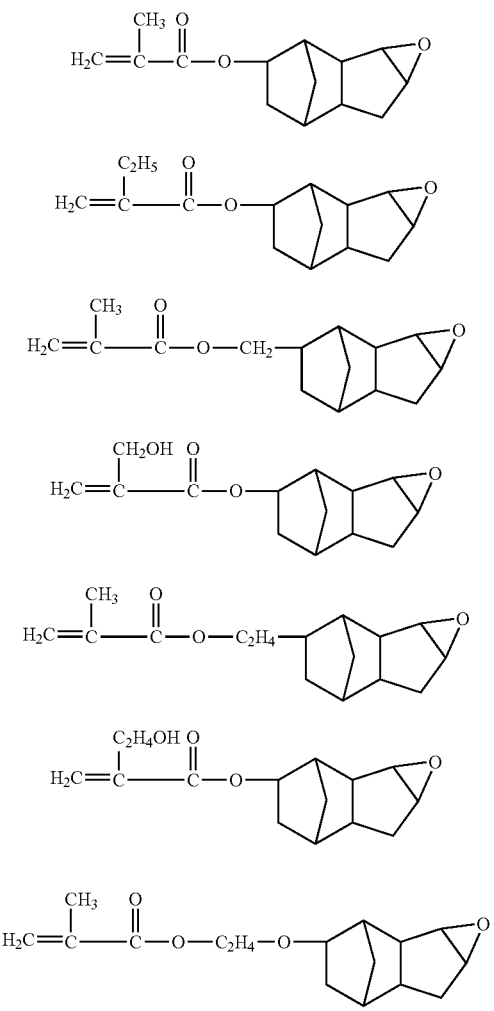

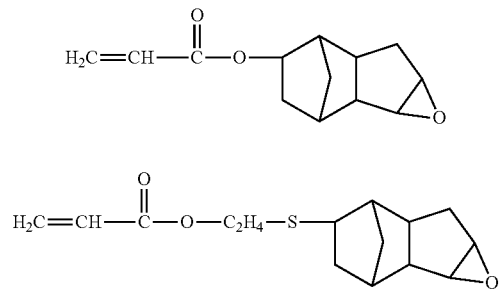

Examples of the compound represented by formula (II) include a compound represented by any of formula (II-1) to formula (II-15). Among these, the compound represented by formula (II-1), formula (II-3), formula (II-5), formula (II-7), formula (II-9), or formula (II-11) to formula (II-15) is preferable, and the compound represented by formula (II-1), formula (II-7), formula (II-9), or formula (II-15) is more preferable.

[Formula 23]

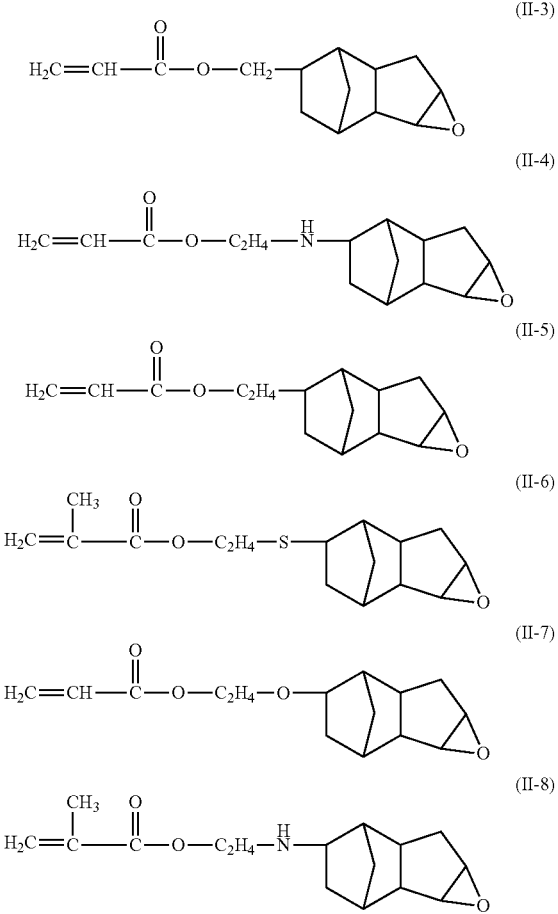

[Formula 24]

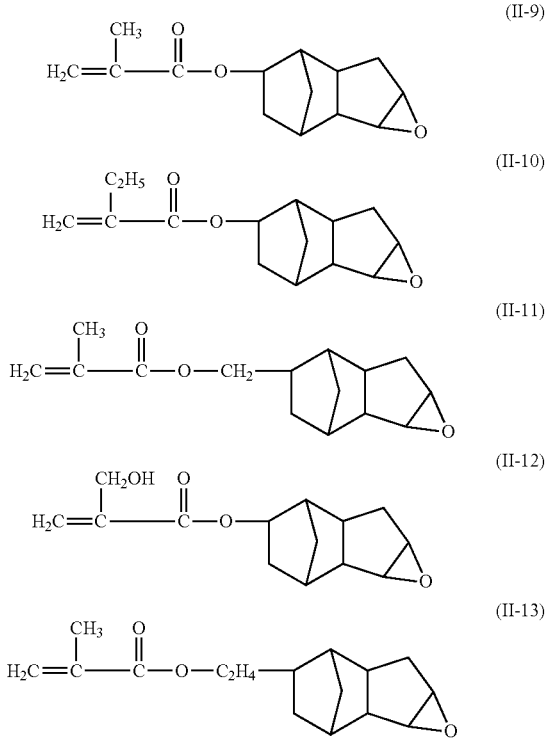

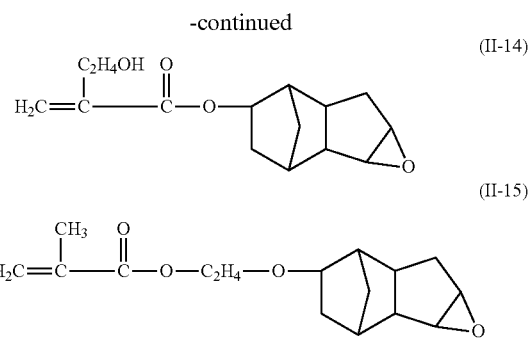

The compound represented by formula (I) and the compound represented by formula (II) may be used singly or in combinations of two or more thereof. When the compound represented by formula (I) and the compound represented by formula (II) are used in combination, the content ratio thereof [compound represented by formula (I): compound represented by formula (II)] is preferably 5:95 to 95:5, and more preferably 20:80 to 80:20, on a molar basis.

(b2) is more preferably a monomer having an oxetanyl group and a (meth)acryloyloxy group. Examples of (b2) include 3-methyl-3-methacryloyloxy methyl oxetane, 3-methyl-3-acryloyloxy methyl oxetane, 3-ethyl-3-methacryloyloxy methyl oxetane, 3-ethyl-3-acryloyloxy methyl oxetane, 3-methyl-3-methacryloyloxy ethyl oxetane, 3-methyl-3-acryloyloxy ethyl oxetane, 3-ethyl-3-methacryloyloxy ethyl oxetane, and 3-ethyl-3-acryloyloxy ethyl oxetane.

(b3) is more preferably a monomer having a tetrahydrofuryl group and a (meth)acryloyloxy group. Specific examples of (b3) include tetrahydrofurfuryl acrylate (for example, Viscoat V #150, manufactured by Osaka Organic Chemical Industry Ltd.) and tetrahydrofurfuryl methacrylate.

(b) is preferably (b1) since reliabilities such as heat resistance and chemical resistance of a color filter to be produced can be further improved. Furthermore, (b1-2) is more preferable since the storage stability of the colored photosensitive resin composition is excellent.

Examples of (c) include (meth)acrylic esters such as methyl(meth)acrylate, ethyl(meth)acrylate, n-butyl(meth)acrylate, sec-butyl(meth)acrylate, tert-butyl(meth)acrylate, 2-ethylhexyl(meth)acrylate, dodecyl(meth)acrylate, lauryl (meth)acrylate, stearyl(meth)acrylate, cyclopentyl(meth)acrylate, cyclohexyl(meth)acrylate, 2-methylcyclohexyl (meth)acrylate, tricyclo[5.2.1.0$^{2,6}$]decan-8-yl(meth)acrylate (referred to as "dicyclopentanyl(meth)acrylate" (common name) in the art or sometimes referred to as "tricyclodecyl (meth)acrylate"), tricyclo[5.2.1.0$^{2,6}$]decene-8-yl(meth)acrylate (which is referred to as "dicyclopentenyl(meth)acrylate" (common name) in the art), dicyclopentanyloxyethyl(meth) acrylate, isobornyl(meth)acrylate, adamantyl(meth)acrylate, allyl(meth)acrylate, propargyl(meth)acrylate, phenyl(meth) acrylate, naphthyl(meth)acrylate, and benzyl(meth)acrylate;

hydroxy group-containing (meth)acrylic esters such as 2-hydroxyethyl(meth)acrylate and 2-hydroxypropyl(meth) acrylate;

dicarboxylic diesters such as diethyl maleate, diethyl fumarate, and diethyl itaconate;

bicyclo unsaturated compounds such as bicyclo[2.2.1] hept-2-ene, 5-methylbicyclo[2.2.1]hept-2-ene, 5-ethylbicyclo[2.2.1]hept-2-ene, 5-hydroxybicyclo[2.2.1]hept-2-ene, 5-hydroxymethylbicyclo[2.2.1]hept-2-ene, 5-(2'-hydroxyethyl)bicyclo[2.2.1]hept-2-ene, 5-methoxybicyclo[2.2.1] hept-2-ene, 5-ethoxybicyclo[2.2.1]hept-2-ene, 5,6-dihydroxybicyclo[2.2.1]hept-2-ene, 5,6-di(hydroxymethyl) bicyclo[2.2.1]hept-2-ene, 5,6-di(2'-hydroxyethyl)bicyclo [2.2.1]hept-2-ene, 5,6-dimethoxybicyclo[2.2.1]hept-2-ene, 5,6-diethoxybicyclo[2.2.1]hept-2-ene, 5-hydroxy-5-methylbicyclo[2.2.1]hept-2-ene, 5-hydroxy-5-ethylbicyclo[2.2.1] hept-2-ene, 5-hydroxymethyl-5-methylbicyclo[2.2.1]hept-2-ene, 5-tert-butoxycarbonylbicyclo[2.2.1]hept-2-ene, 5-cyclohexyloxycarbonylbicyclo[2.2.1]hept-2-ene, 5-phenoxycarbonylbicyclo[2.2.1]hept-2-ene, 5,6-bis(tert-butoxycarbonyl)bicyclo[2.2.1]hept-2-ene, and 5,6-bis(cyclohexyloxycarbonyl)bicyclo[2.2.1]hept-2-ene;

dicarbonylimide derivatives such as N-phenylmaleimide, N-cyclohexylmaleimide, N-benzylmaleimide, N-succinimidyl-3-maleimidobenzoate, N-succinimidyl-4-maleimidobutyrate, N-succinimidyl-6-maleimide caproate, N-succinimidyl-3-maleimide propionate, and N-(9-acridinyl) maleimide;

styrene, α-methylstyrene, m-methylstyrene, p-methylstyrene, vinyltoluene, p-methoxystyrene, acrylonitrile, methacrylonitrile, vinyl chloride, vinylidene chloride, acrylamide, methacrylamide, vinyl acetate, 1,3-butadiene, isoprene, and 2,3-dimethyl-1,3-butadiene.

Among these, from the viewpoint of copolymerization reactivity and heat resistance, 2-hydroxyethyl(meth)acrylate, styrene, vinyltoluene, N-phenylmaleimide, N-cyclohexylmaleimide, N-benzylmaleimide, bicyclo[2.2.1]hept-2-ene and the like are preferable.

In the resin [K1], the ratio of the structural unit derived from each of (a) and (b) in the total structural units constituting the resin [K1] is preferably the following:
the structural unit derived from (a); 2 to 60 mol %; and
the structural unit derived from (b); 40 to 98 mol %, and more preferably the following:
the structural unit derived from (a); 10 to 50 mol %; and
the structural unit derived from (b); 50 to 90 mol %.

When the ratio of the structural unit of the resin [K1] falls within the above-mentioned range, there is a tendency that the storage stability of the colored photosensitive resin composition, that the developability thereof during the formation of a colored pattern, and that the solvent resistance of a color filter to be produced are excellent.

The resin [K1] can be produced with reference to the method described in for example, a document "Experimental Method for Polymer Synthesis" (edited by Takayuki Otsu, published by Kagaku Dojin Publishing Co., Ltd., First Edition, First Printed on Mar. 1, 1972) and cited documents described in the above-mentioned document.

Specific examples thereof include the following method: predetermined amounts of (a) and (b), a polymerization initiator, a solvent and the like are placed in a reaction vessel; for example, a deoxidization atmosphere is formed by substituting oxygen with nitrogen; and these are heated or kept warm during stirring. The polymerization initiator, the solvent and the like which are used here are not particularly limited, and those commonly used in the art can be used. Examples of the polymerization initiator include azo compounds (2,2'-azobisisobutyronitrile, 2,2'-azobis(2,4-dimethylvaleronitrile) and the like) and organic peroxides (benzoyl peroxide and the like). The solvent may be a solvent capable of dissolving each monomer, and examples of the solvent (E) for the colored photosensitive resin composition of the present invention include solvents to be described later.

A solution after a reaction, of the resultant copolymer may be used as it is; a concentrated or diluted solution of the copolymer may be used; or a solid (powder) taken out from the copolymer by a method such as reprecipitation may be used. In particular, the solution after the reaction can be used as it is for preparing the colored photosensitive resin composition of the present invention by using the solvent contained in the colored photosensitive resin composition of the present invention as the solvent during the polymerization, whereby the producing process of the colored photosensitive resin composition of the present invention can be simplified.

In the resin [K2], the ratio of the structural unit derived from each of (a) to (c) in the total structural units constituting the resin [K2] is preferably the following:
the structural unit derived from (a); 2 to 45 mol %;
the structural unit derived from (b); 2 to 95 mol %; and
the structural unit derived from (c); 1 to 65 mol %,
and more preferably the following:
the structural unit derived from (a); 5 to 40 mol %;
the structural unit derived from (b); 5 to 80 mol %; and
the structural unit derived from (c); 5 to 60 mol %.

When the ratio of the structural unit of the resin [K2] falls within the above-mentioned range, there is a tendency that the storage stability of the colored photosensitive resin composition, the developability thereof during the formation of a colored pattern, and the solvent resistance, heat resistance, and mechanical strength of a color filter to be produced are excellent.

The resin [K2] can be produced in the same manner as in the method described as the producing method of the resin [K1], for example.

In the resin [K3], the ratio of the structural unit derived from each of (a) and (c) in the total structural units constituting the resin [K3] is preferably the following:
the structural unit derived from (a); 2 to 60 mol %; and
the structural unit derived from (c); 40 to 98 mol %,
and more preferably the following:
the structural unit derived from (a); 10 to 50 mol % and
the structural unit derived from (c); 50 to 90 mol %.

The resin [K3] can be produced in the same manner as in the method described as the producing method of the resin [K1], for example.

The resin [K4] can be produced by producing a copolymer of (a) and (c) and then adding a cyclic ether having 2 to 4 carbon atoms contained in (b) to a carboxylic acid and/or a carboxylic anhydride contained in (a).

The copolymer of (a) and (c) is first produced in the same manner as in the method described as the producing method of the resin [K1]. In this case, the ratio of the structural unit derived from each of (a) and (c) is preferably the same ratio as that described in the resin [K3].

Next, a cyclic ether having 2 to 4 carbon atoms contained in (b) is reacted with a part of the carboxylic acid and/or the carboxylic anhydride derived from (a) in the copolymer.

Subsequent to the production of the copolymer of (a) and (c), a nitrogen atmosphere in a flask is replaced with air, and (b), a reaction catalyst for a carboxylic acid or a carboxylic anhydride and a cyclic ether (for example, tris(dimethylaminomethyl)phenol and the like), and a polymerization inhibitor (for example, hydroquinone and the like) are placed in a flask, followed by reacting, for example, at 60 to 130° C. for 1 to 10 hours, whereby the resin [K4] can be produced.

The amount of (b) used is preferably 5 to 80 mol, and more preferably 10 to 75 mol, relative to 100 mol of (a). The amount of (b) used falls within the above-mentioned range, whereby there is a tendency that the storage stability of the colored photosensitive resin composition, the developability thereof during the formation of a pattern, and the balance of the solvent resistance, heat resistance, mechanical strength, and sensitivity of the pattern obtained are good. Since the reactivity of the cyclic ether is high, and the unreacted (b) is less likely to remain, (b) used for the resin [K4] is preferably (b1), and more preferably (b1-1).

The amount of the reaction catalyst used is preferably 0.001 to 5 parts by mass relative to 100 parts by mass of the total amount of (a), (b), and (c). The amount of the polymerization inhibitor used is preferably 0.001 to 5 parts by mass relative to 100 parts by mass of the total amount of (a), (b), and (c).

Reaction conditions such as a feeding method, a reaction temperature, and time can be appropriately adjusted in consideration of a production equipment, an amount of heat generation due to polymerization, and the like. In consideration of the production equipment, the amount of heat generation due to polymerization, and the like, the feeding method and the reaction temperature can be appropriately adjusted like the polymerization conditions.

The resin [K5] is produced by producing a copolymer of (b) and (c) in the same manner as in the above-mentioned method for producing the resin [K1] as a first step. In the same manner as in the above, a solution after a reaction, of the resultant copolymer may be used as it is; a concentrated or diluted solution of the copolymer may be used; or a solid (powder) taken out from the copolymer by a method such as reprecipitation may be used.

The ratio of the structural unit derived from each of (b) and (c) relative to the total number of moles of the total structural units constituting the copolymer is preferably the following:
the structural unit derived from (b); 5 to 95 mol %; and
the structural unit derived from (c); 5 to 95 mol %, and more preferably the following:
the structural unit derived from (b); 10 to 90 mol %; and
the structural unit derived from (c); 10 to 90 mol %.

Furthermore, the resin [K5] can be produced by reacting a carboxylic acid or a carboxylic anhydride contained in (a) with the cyclic ether derived from (b) contained in the copolymer of (b) and (c) under the same conditions as those of the producing method of the resin [K4].

The amount of (a) used which is reacted with the copolymer is preferably 5 to 80 mol relative to 100 mol of (b). Since the reactivity of the cyclic ether is high, and the unreacted (b) is less likely to remain, (b) used for the resin [K5] is preferably (b1), and more preferably (b1-1).

The resin [K6] is a resin produced by further reacting a carboxylic anhydride with the resin [K5]. A carboxylic anhydride is reacted with a hydroxy group generated by a reaction between a cyclic ether and a carboxylic acid or a carboxylic anhydride.

Examples of the carboxylic anhydride include maleic anhydride, citraconic anhydride, itaconic anhydride, 3-vinylphthalic anhydride, 4-vinylphthalic anhydride, 3,4,5,6-tetrahydrophthalic anhydride, 1,2,3,6-tetrahydrophthalic anhydride, dimethyltetrahydrophthalic anhydride, and 5,6-dicarboxybicyclo[2.2.1]hept-2-ene anhydride. The amount of the carboxylic anhydride used is preferably 0.5 to 1 mol relative to 1 mol of the amount of (a) used.

Specific examples of the resin (B) include a resin [K1] such as a 3,4-epoxycyclohexylmethyl(meth)acrylate/(meth)acrylic acid copolymer or a 3,4-epoxytricyclo[5.2.1.0$^{2.6}$] decyl acrylate/(meth)acrylic acid copolymer; a resin [K2] such as a glycidyl(meth)acrylate/benzyl(meth)acrylate/(meth)acrylic acid copolymer, a glycidyl(meth)acrylate/styrene/(meth)acrylic acid copolymer, a 3,4-epoxytricyclo [5.2.1.0$^{2.6}$]decyl acrylate/(meth)acrylic acid/N-cyclohexylmaleimide copolymer, 3,4-epoxytricyclo

[5.2.1.0$^{2.6}$]decyl acrylate/(meth)acrylic acid/N-cyclohexylmaleimide/2-hydroxyethyl(meth)acrylate copolymer, or a 3-methyl-3-(meth)acryloyloxymethyl oxetane/(meth)acrylic acid/styrene copolymer; a resin [K3] such as a benzyl(meth)acrylate/(meth)acrylic acid copolymer or a styrene/(meth)acrylic acid copolymer; a resin [K4] such as a resin produced by adding glycidyl(meth)acrylate to a benzyl(meth)acrylate/(meth)acrylic acid copolymer, a resin produced by adding glycidyl(meth)acrylate to a tricyclodecyl(meth)acrylate/styrene/(meth)acrylic acid copolymer, or a resin produced by adding glycidyl(meth)acrylate to a tricyclodecyl(meth)acrylate/benzyl(meth)acrylate/(meth)ac rylic acid copolymer; a resin [K5] such as a resin produced by reacting a tricyclodecyl(meth)acrylate/glycidyl (meth)acrylate copolymer with (meth)acrylic acid or a resin produced by reacting a tricyclodecyl(meth)acrylate/styrene/glycidyl(meth)acrylat e copolymer with (meth)acrylic acid; and a resin [K6] such as a resin produced by reacting a tricyclodecyl(meth)acrylate/glycidyl(meth)acrylate copolymer with (meth)acrylic acid to produce a resin and then reacting this resin with tetrahydrophthalic anhydride.

Among these, the resin (B) is preferably the resin [K1] and the resin [K2], and particularly preferably the resin [K2].

The weight average molecular weight of the resin (B) in terms of polystyrene content is preferably 3,000 to 100,000, more preferably 5,000 to 50,000, and still more preferably 5,000 to 30,000. When the molecular weight falls within the above-mentioned range, there is a tendency that the hardness of the color filter is improved, that the residual film ratio is increased, that the solubility of an unexposed area in a developing solution becomes good, and that the resolution of a colored pattern is improved.

The degree of dispersion [weight average molecular weight (Mw)/number average molecular weight (Mn)] of the resin (B) is preferably 1.1 to 6, and more preferably 1.2 to 4.

The acid value of the resin (B) is preferably 50 to 170 mg-KOH/g, more preferably 60 to 150 mg-KOH/g, and still more preferably 70 to 135 mg-KOH/g, in terms of solid content. The acid value as used herein is a value which is measured as an amount (mg) of potassium hydroxide required for neutralizing 1 g of the resin (B), and which can be determined by, for example, titration with an aqueous potassium hydroxide solution.

The content rate of the resin (B) is preferably 7 to 65% by mass, more preferably 13 to 60% by mass, and still more preferably 17 to 55% by mass, relative to the whole amount of the solid content. When the content rate of the resin (B) falls within the above-mentioned range, there is a tendency that the colored pattern can be formed, and that the resolution of the colored pattern and the residual film ratio are improved.

<Polymerizable Compound (C)>

The polymerizable compound (C) is a compound capable of being polymerized by the action of an active radical and/or an acid generated from the polymerization initiator (D). Examples of the polymerizable compound (C) include a compound having a polymerizable ethylenically unsaturated bond, and is preferably a (meth)acrylic acid ester compound.

Among these, the polymerizable compound (C) is preferably a polymerizable compound having three or more ethylenically unsaturated bonds. Examples of the polymerizable compound include trimethylolpropane tri(meth)acrylate, pentaerythritol tri(meth)acrylate, pentaerythritol tetra(meth)acrylate, dipentaerythritol penta(meth)acrylate, dipentaerythritol hexa(meth)acrylate, tripentaerythritol octa(meth)acrylate, tripentaerythritol hepta(meth)acrylate, tetrapentaerythritol deca(meth)acrylate, tetrapentaerythritol nona(meth)acrylate, tris(2-(meth)acryloyloxyethyl)isocyanurate, ethylene glycol-modified pentaerythritol tetra(meth)acrylate, ethylene glycol-modified dipentaerythritol hexa(meth) acrylate, propylene glycol-modified pentaerythritol tetra(meth)acrylate, propylene glycol-modified dipentaerythritol hexa(meth)acrylate, caprolactone-modified pentaerythritol tetra(meth)acrylate, and caprolactone-modified dipentaerythritol hexa(meth)acrylate.

Among these, dipentaerythritol penta(meth)acrylate and dipentaerythritol hexa(meth)acrylate are preferable.

The weight average molecular weight of the polymerizable compound (C) is preferably 150 or more and 2,900 or less, and more preferably 250 or more and 1,500 or less.

The content rate of the polymerizable compound (C) is preferably 7 to 65% by mass, more preferably 13 to 60% by mass, and still more preferably 13 to 55% by mass, relative to the whole amount of the solid content. When the content rate of the polymerizable compound (C) falls within the above-mentioned range, there is a tendency that the residual film ratio during the formation of the colored pattern and the chemical resistance of the color filter are improved.

<Polymerization Initiator (D)>

The polymerization initiator (D) is not particularly limited, as long as the polymerization initiator (D) is a compound capable of generating active radicals, an acid or the like by the action of light or heat to initiate polymerization. Any known polymerization initiator can be used. Examples of the polymerization initiator capable of generating active radicals include an alkylphenone compound, a triazine compound, an acylphosphine oxide compound, an O-acyloxime compound, and a biimidazole compound.

The O-acyloxime compound is a compound having a partial structure represented by formula (d1). Hereinafter, * represents a point of attachment.

[Formula 25]

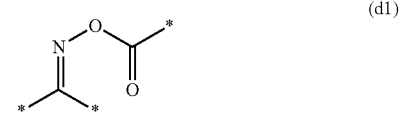

(d1)

Examples of the O-acyloxime compound include N-benzoyloxy-1-(4-phenylsulfanylphenyl)butane-1-one-2-imine, N-benzoyloxy-1-(4-phenylsulfanylphenyl)octane-1-one-2-imine, N-benzoyloxy-1-(4-phenylsulfanylphenyl)-3-cyclopentylpropane-1-one-2-imine, N-acetoxy-1-[9-ethyl-6-(2-methylbenzoyl)-9H-carbazole-3-yl]ethane-1-imine, N-acetoxy-1-[9-ethyl-6-{2-methyl-4-(3,3-dimethyl-2,4-dioxacyclopentanylmethyloxy)benzoyl}-9H-carbazole-3-yl] ethane-1-imine, N-acetoxy-1-[9-ethyl-6-(2-methylbenzoyl)-9H-carbazole-3-yl]-3-cyclopentylpropane-1-imine, and N-benzoyloxy-1-[9-ethyl-6-(2-methylbenzoyl)-9H-carbazole-3-yl]-3-cyclopentylpropane-1-one-2-imine. Commercially available products such as Irgacures OXE01 and OXE02 (all manufactured by BASF Corporation), and N-1919 (manufactured by ADEKA Corporation) may be used. Among these, the O-acyloxime compound is preferably at least one selected from the group consisting of N-benzoyloxy-1-(4-phenylsulfanylphenyl)butane-1-one-2-imine, N-benzoyloxy-1-(4-phenylsulfanylphenyl)octane-1-one-2-imine, and N-benzoyloxy-1-(4-phenylsulfanylphenyl)-3-cyclopentylpropane-1-one-2-imine, and more preferably N-benzoyloxy-1-(4-phenylsulfanylphenyl)octane-1-one-2-imine. There is a tendency that these O-acyloxime compounds provide a color filter having a high brightness.

The alkylphenone compound is a compound having a partial structure represented by formula (d2) or a partial structure represented by formula (d3). In these partial structures, the benzene ring optionally has a substituent.

[Formula 26]

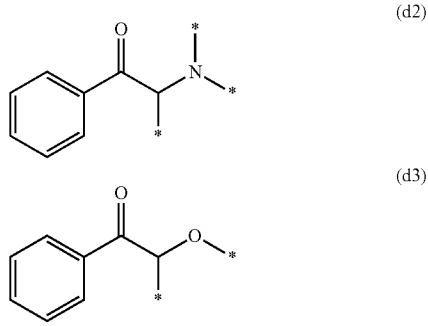

(d2)

(d3)

Examples of the compound having a partial structure represented by formula (d2) include 2-methyl-2-morpholino-1-(4-methylsulfanylphenyl)propane-1-one, 2-dimethylamino-1-(4-morpholinophenyl)-2-benzylbutane-1-one, and 2-(dimethylamino)-2-[(4-methylphenyl)methyl]-1-[4-(4-morpholinyl)phenyl]butane-1-one. Commercially available products such as Irgacures 369, 907, and 379 (all manufactured by BASF Corporation) may be used.

Examples of the compound having a partial structure represented by formula (d3) include 2-hydroxy-2-methyl-1-phenylpropane-1-one, 2-hydroxy-2-methyl-1-[4-(2-hydroxyethoxy)phenyl]propane-1-one, 1-hydroxycyclohexylphenylketone, an oligomer of 2-hydroxy-2-methyl-1-(4-isopropenylphenyl)propane-1-one, α,α-diethoxyacetophenone, and benzyl dimethyl ketal.

The alkylphenone compound is preferably a compound having a partial structure represented by formula (d2) from the viewpoint of sensitivity.

Examples of the triazine compound include 2,4-bis(trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-piperonyl-1,3,5-triazine, 2,4-bis(trichloromethyl)-6-(4-methoxystyryl)-1,3,5-triazine, 2,4-bis(trichloromethyl)-6-[2-(5-methylfuran-2-yl)ethenyl]-1,3,5-triazine, 2,4-bis(trichloromethyl)-6-[2-(furan-2-yl)ethenyl]-1,3,5-triazine, 2,4-bis(trichloromethyl)-6-[2-(4-diethylamino-2-methylphenyl)ethenyl]-1,3,5-triazine, and 2,4-bis(trichloromethyl)-6-[2-(3,4-dimethoxyphenyl)ethenyl]-1,3,5-triazine.

Examples of the acylphosphine oxide compound include 2,4,6-trimethylbenzoyldiphenylphosphine oxide. Commercially available products such as Irgacure (registered trademark) 819 (manufactured by BASF Corporation) may be used.

Examples of the biimidazole compound include 2,2'-bis(2-chlorophenyl)-4,4',5,5'-tetraphenylbiimidazole, 2,2'-bis(2,3-dichlorophenyl)-4,4',5,5'-tetraphenylbiimidazole (for example, see Japanese Patent Laid-Open No. 6-75372 and Japanese Patent Laid-Open No. 6-75373), 2,2'-bis(2-chlorophenyl)-4,4',5,5'-tetraphenyl biimidazole, 2,2'-bis(2-chlorophenyl)-4,4',5,5'-tetra(alkoxyphenyl)biimidazole, 2,2'-bis(2-chlorophenyl)-4,4',5,5'-tetra(dialkoxyphenyl) biimidazole, 2,2'-bis(2-chlorophenyl)-4,4',5,5'-tetra(trialkoxyphenyl)biimidazole (for example, see Japanese Patent No. 48-38403 and Japanese Patent Laid-Open No. 62-174204), and a biimidazole compound in which a phenyl group at the 4,4',5,5' position is substituted with a carboalkoxy group (for example, see Japanese Patent Laid-Open No. 7-10913).

Furthermore, examples of the polymerization initiator (D) include benzoin compounds such as benzoin, benzoin methyl ether, benzoin ethyl ether, benzoin isopropyl ether, and benzoin isobutyl ether; benzophenone compounds such as benzophenone, methyl o-benzoylbenzoate, 4-phenylbenzophenonne, 4-benzoyl-4'-methyldiphenyl sulfide, 3,3',4,4'-tetra(tert-butylperoxycarbonyl)benzophenone, and 2,4,6-trimethylbenzophenone; quinone compounds such as 9,10-phenanthrene quinone, 2-ethylanthraquinone, and camphorquinone; 10-butyl-2-chloroacridone, benzyl, methyl phenylglyoxylate, and a titanocene compound. These are preferably used in combination with a polymerization initiation aid (D1) (particularly, amines) to be described later.

Examples of an acid generator include onium salts such as 4-hydroxyphenyldimethylsulfonium p-toluenesulfonate, 4-hydroxyphenyldimethylsulfoniumhexafluoroantimonate, 4-acetoxyphenyldimethylsulfonium p-toluenesulfonate, 4-acetoxyphenyl-methyl-benzylsulfoniumhexafluoroantimonate, triphenylsulfonium p-toluenesulfonate, triphenylsulfonium hexafluoroantimonate, diphenyliodonium p-toluenesulfonate, and diphenyliodoniumhexafluoroantimonate, nitrobenzyl tosylates, and benzoin tosylate.

The polymerization initiator (D) is preferably a polymerization initiator containing at least one selected from the group consisting of an alkylphenone compound, a triazine compound, an acylphosphine oxide compound, an O-acyloxime compound, and a biimidazole compound, and more preferably a polymerization initiator containing an O-acyloxime compound.

The content of the polymerization initiator (D) is preferably 0.1 to 30 parts by mass, and more preferably 1 to 20 parts by mass, relative to 100 parts by mass of the whole amount of the resin (B) and the polymerizable compound (C). When the content of the polymerization initiator (D) falls within the above-mentioned range, there is a tendency that the sensitivity is increased and that the time of exposure to light is shortened, resulting in the improvement in productivity of the color filter.

<Polymerization Initiation Aid (D1)>

The polymerization initiation aid (D1) is a compound to be used for accelerating polymerization of a polymerizable compound the polymerization of which has been started by the polymerization initiator or a sensitizer. When the polymerization initiation aid (D1) is contained, the polymerization initiation aid (D1) is commonly used in combination with the polymerization initiator (D).

Examples of the polymerization initiation aid (D1) include an amine compound, an alkoxyanthracene compound, a thioxanthone compound, and a carboxylic acid compound.

Examples of the amine compound include triethanolamine, methyldiethanolamine, triisopropanolamine, methyl 4-dimethylaminobenzoate, ethyl 4-dimethylaminobenzoate, isoamyl 4-dimethylaminobenzoate, 2-dimethylaminoethyl benzoate, 2-ethylhexyl 4-dimethylaminobenzoate, N,N-dimethylparatoluidine, 4,4'-bis(dimethylamino)benzophenone (common name: Michler's ketone), 4,4'-bis (diethylamino)benzophenone, and 4,4'-bis(ethylmethylamino)benzophenone. Among these, 4,4'-bis(diethylamino)benzophenone is preferable. Commercially available products such as EAB-F (manufactured by Hodogaya Chemical Co., Ltd.), may be used.

Examples of the alkoxy anthracene compound include 9,10-dimethoxyanthracene, 2-ethyl-9,10-dimethoxyanthracene, 9,10-diethoxyanthracene, 2-ethyl-9,10-diethoxyanthracene, 9,10-dibutoxyanthracene, and 2-ethyl-9,10-dibutoxyanthracene.

Examples of the thioxanthone compound include 2-isopropylthioxanthone, 4-isopropylthioxanthone, 2,4-diethylthioxanthone, 2,4-dichlorothioxanthone, and 1-chloro-4-propoxythioxanthone.

Examples of the carboxylic acid compound include phenylsulfanylacetic acid, methylphenylsulfanylacetic acid, ethylphenylsulfanylacetic acid, methylethylphenylsulfanylacetic acid, dimethylphenylsulfanylacetic acid, methoxyphenysulfanylacetic acid, dimethoxyphenylsulfanylacetic acid, chlorophenylsulfanylacetic acid, dichlorophenylsulfanylacetic acid, N-phenylglycine, phenoxyacetic acid, naphthylthioacetic acid, N-naphthylglycine, and naphthoxyacetic acid.

When the polymerization initiation aid (D1) is used, the content thereof is preferably 0.1 to 30 parts by mass, and more preferably 1 to 20 parts by mass, relative to 100 parts by mass of the whole amount of the resin (B) and the polymerizable compound (C). When the amount of the polymerization initiation aid (D1) falls within the above-mentioned range, there is a tendency that the colored pattern can be formed with higher sensitivity, resulting in the improvement in productivity of the color filter.

<Solvent (E)>

The solvent (E) is not particularly limited, and any solvent which has been used conventionally in the art can be used. Examples of the solvent (E) include an ester solvent (a solvent which contains —COO— but does not contain —O— in its molecule), an ether solvent (a solvent which contains —O— but does not contain —COO— in its molecule), an ether ester solvent (a solvent which contains —COO— and —O— in its molecule), a ketone solvent (a solvent which contains —CO— but does not contain —COO— in its molecule), an alcohol solvent (a solvent which contains OH but does not contain —O—, —CO— nor —COO— in its molecule), an aromatic hydrocarbon solvent, an amide solvent, and dimethyl sulfoxide.

Examples of the ester solvent include methyl lactate, ethyl lactate, butyl lactate, methyl 2-hydroxy isobutanoate, ethyl acetate, n-butyl acetate, isobutyl acetate, pentyl formate, isopentyl acetate, butyl propionate, isopropyl butyrate, ethyl butyrate, butyl butyrate, methyl pyruvate, ethyl pyruvate, propyl pyruvate, methyl acetoacetate, ethyl acetoacetate, cyclohexanol acetate, and γ-butyrolactone.

Examples of the ether solvent include ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monobutyl ether, propylene glycol monomethyl ether, propylene glycol monoethyl ether, propylene glycol monopropyl ether, propylene glycol monobutyl ether, 3-methoxy-1-butanol, 3-methoxy-3-methylbutanol, tetrahydrofuran, tetrahydropyran, 1,4-dioxane, diethylene glycol dimethyl ether, diethylene glycol diethyl ether, diethylene glycol methyl ethyl ether, diethylene glycol dipropyl ether, diethylene glycol dibutyl ether, anisole, phenetol, and methyl anisole.

Examples of the ether ester solvent include methyl methoxyacetate, ethyl methoxyacetate, butyl methoxyacetate, methyl ethoxyacetate, ethyl ethoxyacetate, methyl 3-methoxypropionate, ethyl 3-methoxypropionate, methyl 3-ethoxypropionate, ethyl 3-ethoxypropionate, methyl 2-methoxypropionate, ethyl 2-methoxypropionate, propyl 2-methoxypropionate, methyl 2-ethoxy propionate, ethyl 2-ethoxypropionate, methyl 2-methoxy-2-methylpropionate, ethyl 2-ethoxy-2-methylpropionate, 3-butyl methoxyacetate, 3-methyl-3-butyl methoxyacetate, propylene glycol monomethyl ether acetate, propylene glycol monoethyl ether acetate, propylene glycol monopropyl ether acetate, ethylene glycol monomethyl ether acetate, ethylene glycol monoethyl ether acetate, diethylene glycol monoethyl ether acetate, and diethylene glycol monobutyl ether acetate.

Examples of the ketone solvent include 4-hydroxy-4-methyl-2-pentanone, acetone, 2-butanone, 2-heptanone, 3-heptanone, 4-heptanone, 4-methyl-2-pentanone, cyclopentanone, cyclohexanone, and isophorone.

Examples of the alcohol solvent include methanol, ethanol, propanol, butanol, hexanol, cyclohexanol, ethylene glycol, propylene glycol, and glycerin.

Examples of the aromatic hydrocarbon solvent include benzene, toluene, xylene, and mesitylene.

Examples of the above amide solvent include N,N-dimethylformamide, N,N-dimethylacetamide, and N-methylpyrrolidone.

Among the solvents, preferred is an organic solvent having a boiling point of 120° C. or higher and 180° C. or lower at 1 atm from the viewpoint of applicability and drying performance. The solvent is preferably propylene glycol monomethyl ether acetate, ethyl lactate, propylene glycol monomethyl ether, ethyl 3-ethoxypropionate, ethylene glycol monomethyl ether, diethylene glycol monomethyl ether, diethylene glycol monoethyl ether, 4-hydroxy-4-methyl-2-pentanone, and N,N-dimethylformamide, and more preferably propylene glycol monomethyl ether acetate, propylene glycol monomethyl ether, ethyl lactate, and ethyl 3-ethoxypropionate.

The content rate of the solvent (E) is preferably 70 to 95% by mass, and more preferably 75 to 92% by mass, relative to the whole amount of the colored photosensitive resin composition of the present invention. In other words, the total content rate of the solid content of the colored photosensitive resin composition is preferably 5 to 30% by mass, and more preferably 8 to 25% by mass. When the content rate of the solvent (E) falls within the above-mentioned range, there is a tendency that the flatness during application becomes good and the color density of the color filter formed becomes not insufficient, resulting in the achievement of good displaying properties.

<Leveling Agent (F)>

Examples of the leveling agent (F) include a silicone-based surfactant, a fluorine-based surfactant, and a silicone-based surfactant having a fluorine atom. These may have a polymerizable group at its side chain.

Examples of the silicone-based surfactant include a surfactant having a siloxane bond in its molecule. Specific examples thereof include Toray Silicone DC3PA, Toray Silicone SH7PA, Toray Silicone DC11PA, Toray Silicone SH21PA, Toray Silicone SH28PA, Toray Silicone SH29PA, Toray Silicone SH30PA, and Toray Silicone SH8400 (manufactured by Dow Corning Toray Co., Ltd.); KP321, KP322, KP323, KP324, KP326, KP340, and KP341 (manufactured by Shin-Etsu Silicone Co., Ltd.); and TSF400, TSF401, TSF410, TSF4300, TSF4440, TSF4445, TSF-4446, TSF4452, and TSF4460 (manufactured by Momentive Performance Materials Inc.).

Examples of the fluorine-based surfactant include a surfactant having a fluorocarbon chain in its molecule. Specific examples thereof include Fluorad (registered trademark) FC430 and Fluorad FC431 (manufactured by Sumitomo 3M, Ltd.); Megafac (registered trademark) F142D, Megafac F171, Megafac F172, Megafac F173, Megafac F177, Megafac F183, Megafac F554, Megafac R30, and Megafac RS-718-K (manufactured by DIC Corporation); Eftop (registered trademark) EF301, Eftop EF303, Eftop EF351, and Eftop EF352 (manufactured by Mitsubishi Materials Electronic Chemicals Co., Ltd.); Surflon (registered trademark) 5381, Surflon 5382, Surflon SC101, and Surflon SC105 (manufactured by Asahi Glass Co., Ltd.); and E5844 (manufactured by Daikin Finechemical Laboratory).

Examples of the silicone-based surfactant having a fluorine atom include a surfactant having a siloxane bond and a fluorocarbon chain in its molecule. Specific examples thereof include Megafac (registered trademark) R08, Megafac BL20, Megafac F475, Megafac F477, and Megafac F443 (manufactured by DIC Corporation).

The content rate of the leveling agent (F) is preferably 0.001% by mass or more and 0.2% by mass or less, more preferably 0.002% by mass or more and 0.2% by mass or less, and still more preferably 0.01% by mass or more and 0.2% by mass or less, relative to the whole amount of the colored photosensitive resin composition. This content rate does not include the content rate of the dispersant. When the content rate of the leveling agent (F) falls within the above-mentioned range, the flatness of the color filter can be improved.

<Other Components>

If required, the colored photosensitive resin composition of the present invention may contain an additive known in the art, such as a filler, other polymeric compound, an adhesion promoter, a light stabilizer, or a chain transfer agent.

Examples of the adhesion promoter include vinyltrimethoxysilane, vinyltriethoxysilane, vinyltris(2-methoxyethoxy)silane, 3-glycidyloxypropyltrimethoxysilane, 3-glycidyloxypropylmethyldimethoxysilane, 3-glycidyloxypropylmethyldiethoxysilane, 2-(3,4-epoxycyclohexyl)ethyltrimethoxysilane, 3-chloropropylmethyldimethoxysilane, 3-chloropropyltrimethoxysilane, 3-methacryloyloxypropyltrimethoxysilane, 3-sulfanylpropyltrimethoxysilane, 3-isocyanato propyltriethoxysilane, N-2-(aminoethyl)-3-aminopropylmethyldimethoxysilane, N-2-(aminoethyl)-3-aminopropylmethyldiethoxysilane, N-2-(aminoethyl)-3-aminopropyltrimethoxysilane, 3-aminopropyltrimethoxysilane, 3-aminopropyltriethoxysilane, N-phenyl-3-aminopropyltrimethoxysilane, and N-phenyl-3-aminopropyltriethoxysilane.

<Method for Producing Colored Photosensitive Resin Composition>

The colored photosensitive resin composition of the present invention can be prepared by, for example, mixing a colorant (A), a resin (B), a polymerizable compound (C), and a polymerization initiator (D), and a solvent (E), a leveling agent (F), a polymerization initiation aid (D1), and other component used if required.

<Method for Producing Color Filter>

Examples of the method for producing the colored pattern from the colored photosensitive resin composition of the present invention include a photolithography method, an inkjet method, and a printing method. Among these methods, a photolithography method is preferable. The photolithography method is a method in which the colored photosensitive resin composition is applied onto a substrate and then dried to form a coloring composition layer, and the coloring composition layer is then developed by exposing the coloring composition layer to light through a photomask. In the photolithography method, the photomask is not used during the exposure to light, and/or the coloring composition layer is not developed, whereby a colored coating film which is a hardened material of the coloring composition layer can be formed. The colored pattern and the colored coating film which have been formed thus are the color filter of the present invention.

The film thickness of the color filter to be prepared is not particularly limited, and can be appropriately adjusted depending on objects, applications and the like. For example, the film thickness of the color filter is 0.1 to 30 μm, preferably 0.1 to 20 μm, and more preferably 0.5 to 6 μm. When color filters have the same chromaticity, the thin color filter is advantageous for producing a lightweight thin display device.

Examples of the substrate to be used include glass substrates such as quartz glass, borosilicate glass, alumina silicate glass, and soda lime glass of which the surface is coated with silica; resin substrates such as polycarbonate, poly(methyl methacrylate), and polyethylene terephthalate; silicon; and substrates on which aluminum, silver, or a silver/copper/palladium alloy thin film or the like is formed. On these substrates, other color filter layer, a resin layer, a transistor, a circuit and the like may be formed.

The formation of each color pixel using a photolithography method can be carried out using a known or conventional device or under known or conventional conditions. For example, the color pixel can be prepared in the following manner.

First, a colored photosensitive resin composition is applied onto a substrate, and then dried by heat-drying (prebaking) and/or drying under reduced pressure to remove volatile components such as a solvent from the composition, thereby producing a smooth coloring composition layer.

Examples of the application method include a spin coat method, a slit coat method, and a slit-and-spin coat method.

The temperature to be employed when heat-drying is carried out is preferably 30 to 120° C., and more preferably 50 to 110° C. The time for the heating is preferably 10 seconds to 60 minutes, and more preferably 30 seconds to 30 minutes.

When drying under reduced pressure is carried out, the drying procedure is preferably carried out at a temperature range of 20 to 25° C. under a pressure of 50 to 150 Pa.

The film thickness of the coloring composition layer is not particularly limited, and may be selected appropriately depending on the desired film thickness of the color filter.

Next, the coloring composition layer is exposed to light through a photomask for forming a desired colored pattern. The pattern on the photomask is not particularly limited, and a pattern suitable for the intended application is used.

A light source to be used for the exposure to light is preferably a light source capable of generating light having a wavelength of 250 to 450 nm. For example, light having a wavelength of shorter than 350 nm may be cut with a filter capable of cutting light having this wavelength region, or light having a wavelength of around 436 nm, around 408 nm, or around 365 nm may be extracted selectively with a band-pass filter capable of extracting light having those wavelength region. Specific examples thereof include a mercury lamp, a light-emitting diode, a metal halide lamp, and a halogen lamp.

A light-exposing device such as a mask aligner and a stepper is preferably used because the device is capable of emitting a parallel light beam uniformly over the whole area of the exposed surface or accurately aligning the photomask to the substrate which has the coloring composition layer formed thereon.

A colored pattern is formed on the substrate by bringing the exposed coloring composition layer into contact with a developing solution to develop the coloring composition layer. By developing, an unexposed area in the coloring composition layer is dissolved in the developing solution and therefore removed. The developing solution is preferably an aqueous solution of an alkaline compound such as potassium hydroxide, sodium hydrogen carbonate, sodium carbonate, or tetramethylammonium hydroxide. The concentration of the alkaline compound in the aqueous solution is preferably 0.01 to 10% by mass, and more preferably 0.03 to 5% by mass. The developing solution may further contain a surfactant.

The developing method may be any of a paddle method, a dipping method, a spray method and the like. Furthermore, during the developing process, the substrate may be inclined at any angle.

After the developing process, the resultant product is preferably washed with water.

Furthermore, the resultant colored pattern is preferably subjected to post-baking. The temperature for the post-baking is preferably 150 to 250° C., and more preferably 160 to 235° C. The time for the post-baking is preferably 1 to 120 minutes, and more preferably 10 to 60 minutes.

The colored photosensitive resin composition of the present invention makes it possible to prepare a color filter having a high brightness, in particular, when y is 0.080 to 0.130, and x is 0.125 to 0.230, and preferably 0.125 to 0.150. It is extremely important that the brightness of the color filter is as high as possible. For example, the brightness is increased by 0.1, whereby the output of a backlight can be suppressed, which makes it possible to increase the life of a battery. A color filter having small x can be prepared, whereby a thin color filter having a wide color reproduction region can be formed. The color filter is useful as a color filter used for a display device (for example, a liquid crystal display device, an organic EL device, an electronic paper or the like) and a solid-state image sensor.

EXAMPLES

Hereinafter, the present invention will be described in more detail by Examples, and the present invention is not limited by these Examples. Percentages and parts expressing contents or amounts used in the examples are mass basis, unless otherwise specified.

Hereinafter, the structures of the compounds were confirmed by mass spectrometry (LC; model 1200, manufactured by Agilent, MASS; model LC/MSD, manufactured by Agilent).

Synthetic Example 1

The following reaction was carried out under a nitrogen atmosphere. Into a flask equipped with a cooling tube and a stirrer, 26.4 parts of potassium thiocyanate and 156 parts of acetonitrile were introduced, followed by stirring at room temperature for 30 minutes. 40.0 parts of 2,6-difluorobenzoic acid chloride (manufactured by Tokyo Chemical Industry Co., Ltd.) was added dropwise to the flask over 30 minutes, followed by stirring at room temperature for 1 hour. 30.6 parts of N-ethyl-o-toluidine (manufactured by Tokyo Chemical Industry Co., Ltd.) was added dropwise to the flask over 30 minutes, followed by stirring at room temperature for 1 hour. Into the flask, an aqueous solution containing 79.2 parts of sodium monochloroacetate dissolved in 120 parts of ion-exchange water was introduced, and 60.4 parts of an aqueous 30% sodium hydroxide solution was then introduced, followed by stirring at room temperature for 18 hours. Furthermore, 600 parts of ion-exchange water was added to the flask, followed by stirring for 1 hour, to collect a precipitated pale yellow solid by filtration. The resultant pale yellow solid was washed with 120 parts of acetonitrile, and then washed with 560 parts of ion-exchange water. The washed pale yellow solid, 156 parts of ion-exchange water, 35.0 parts of 99% acetic acid (manufactured by Wako Pure Chemical Industries, Ltd.), and 156 parts of toluene were introduced into a flask equipped with a stirrer, followed by stirring at room temperature for 2 hours. 80.8 parts of an aqueous 30% sodium hydroxide solution was added dropwise thereto over 10 minutes, followed by stirring for 5 minutes, to remove an aqueous layer through a separation procedure. 156 parts of ion-exchange water was added to the resultant organic layer for separation and washing, and 156 parts of ion-exchange water and 0.1 parts of 35% hydrochloric acid were then added for separation and washing. The resultant organic layer was concentrated using an evaporator, and then dried under reduced pressure at 35° C. to produce a compound represented by formula (B-I-1) as a white solid. The yield was 43.4 parts and the yield rate was 58.0%.

[Formula 27]

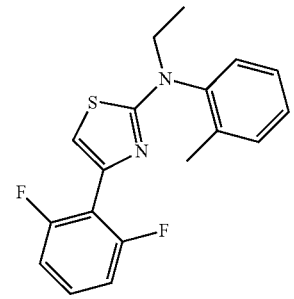

(B-I-1)

The following reaction was carried out under a nitrogen atmosphere. Into a flask equipped with a cooling tube and a stirrer, 13.2 parts of a compound represented by formula (B-I-1), 19.0 parts of a compound represented by formula (C-I-1), and 38 parts of toluene were introduced. Then, 9.2 parts of phosphorus oxychloride was added thereto, followed by stirring at 100° C. for 7 hours. The reaction mixture was then cooled to room temperature, and then diluted with 29 parts of methyl ethyl ketone. To the diluted reaction mixture, a mixed solution of 114 parts of ion-exchange water and 10 parts of an aqueous 35% hydrochloric acid solution was then poured, to remove an aqueous layer through a separation procedure. The solvent was distilled off from the resultant organic layer using an evaporator, followed by drying under reduced pressure at 60° C.

to produce a compound represented by formula (X-II-1) as a blue violet solid. The yield of the blue violet solid was 39.4 parts.

[Formula 28]

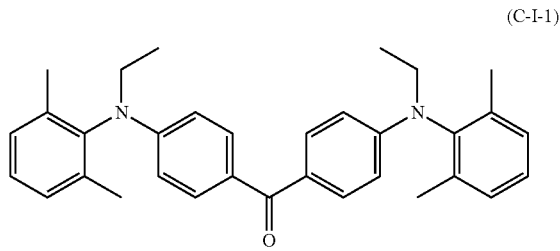

(C-I-1)

[Formula 29]

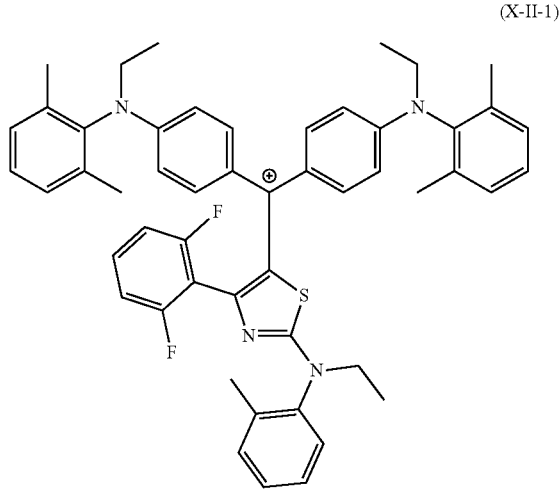

(X-II-1)

The following reaction was carried out under a nitrogen atmosphere. Into a flask equipped with a cooling tube and a stirrer, 38.4 parts of a compound represented by formula (X-II-1) and 112 parts of methylene chloride were introduced, followed by stirring for 30 minutes. The reaction solution was ice-cooled, and 31.6 parts of chlorosulfonic acid (manufactured by Tokyo Chemical Industry Co., Ltd.) was added thereto while the internal temperature was kept at 10° C. Then, the reaction solution was heated to room temperature, followed by stirring for 9 hours. Then, the reaction solution was ice-cooled, and diluted with a mixed solution of 64 parts of N,N-dimethylformamide and 4.9 parts of ion-exchange water while the internal temperature was kept at 10° C. The diluted reaction solution was poured into 1120 parts of toluene, followed by stirring for 30 minutes, so that a viscous solid precipitated. An oil layer was discharged by decantation, and 320 parts of toluene was then added to the resultant viscous solid, followed by stirring for 30 minutes. 832 parts of 20% brine was added to the viscous solid produced by discharging the oil layer by decantation, followed by stirring for 1 hour. Then, a blue solid was collected by filtration. The resultant blue solid was washed with 576 parts of 20% brine, and dried under reduced pressure at 35° C. The resultant solid and 128 parts of methanol were introduced into a flask equipped with a stirrer, stirred for 30 minutes, and then separated into a solid and a filtrate by filtration. This filtrate is defined as filtrate A3. The solid collected by filtration was washed with 192 parts of methanol, and separated into a solid and a filtrate by filtration. This filtrate is defined as filtrate B3. The filtrate A3 and the filtrate B3 were mixed. The solvent was removed from the mixture using an evaporator, followed by drying under reduced pressure at 40° C. to produce a compound represented by formula (X-I-1) as a blue violet solid. The yield of the blue violet solid was 38.3 parts.

[Formula 30]

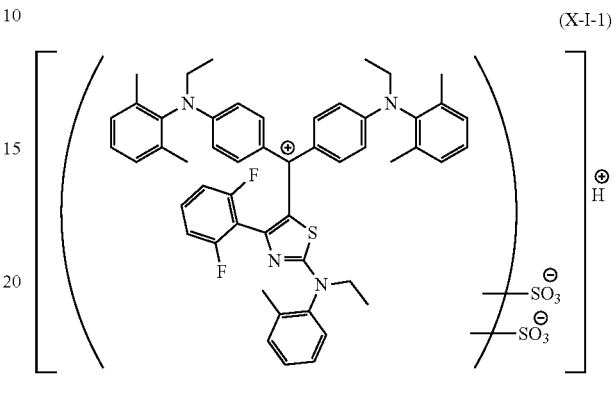

(X-I-1)

Into a flask equipped with a cooling tube and a stirrer, 28.0 parts of a compound represented by formula (X-I-1), 43.2 parts of barium chloride dihydrate, and 356 parts of ion-exchange water were added, followed by stirring at 40° C. for 2 hours. Then, the reaction suspension was filtered. Into a flask equipped with a stirrer, the solid collected by filtration and 350 parts of ion-exchange water were introduced, followed by stirring for 30 minutes. The suspension was then filtered. The resultant solid was washed with 280 parts of ion-exchange water, and then dried under reduced pressure at 60° C. to produce a compound represented by formula (A-I-1) as a blue violet solid. The yield was 24.5 parts and the yield rate was 81.7%.

[Formula 31]

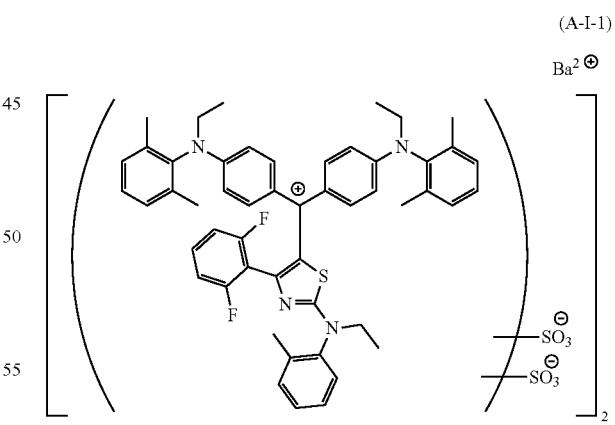

(A-I-1)

Identificiation of Compound Represented by Formula (A-I-1) (Mass spectrometry) ionization mode=ESI-: m/s= 949.5 [M−Ba+2H]⁻
Exact Mass [M−Ba]: 947.28

Resin Synthesis Example 1

A proper amount of nitrogen was flown into a flask equipped with a reflux condenser, a dropping funnel, and a stirrer to purge the inside of the flask with a nitrogen atmosphere. 141 parts of ethyl lactate and 178 parts of propylene glycol monomethyl ether acetate were placed in the flask, and the mixture was then heated to 85° C. while stirring. Then, a mixed solution of 38 parts of acrylic acid, 25 parts of a mixture (content rate: 1:1) of 3,4-epoxytricyclo [5.2.1.0$^{2,6}$]deca-8-yl acrylate, and 3,4-epoxytricyclo [5.2.1.0$^{2,6}$]deca-9-yl acrylate, 137 parts of cyclohexylmaleimide, 50 parts of 2-hydroxyethyl methacrylate, and 338 parts of propylene glycol monomethyl ether acetate was added dropwise thereto over 5 hours. Meanwhile, a mixed solution containing 5 parts of 2,2-azobisisobutyronitrile dissolved in 88 parts of propylene glycol monomethyl ether acetate was added dropwise thereto over 6 hours. After the completion of the dropwise addition, the resultant solution was held at the same temperature for 4 hours, and then cooled to room temperature to produce a copolymer (resin (B-1)) solution having a solid content of 25.6%. The produced copolymer had a weight average molecular weight Mw of 8000, a degree of dispersion of 2.1, and an acid value of 111 mg-KOH/g in terms of solid content. The resin (B-1) has the following structural unit.

[Formula 32]

The weight average molecular weight (Mw) and the number average molecular weight (Mn) of the resin in terms of polystyrene content were measured using the GPC method under the following conditions.
Device; HLC-8120GPC (manufactured by Tosoh Corporation)
Column; TSK-GELG2000HXL
Column temperature; 40° C.
Solvent; THF
Flow rate; 1.0 mL/min Solid content concentration of suspected solution; 0.001 to 0.01% by mass
Injected amount; 50 μL
Detector; RI
Reference substance for correction; TSK STANDARD POLYSTYRENE F-40, F-4, F-288, A-2500, A-500 (manufactured by Tosoh Corporation)

The ratio (Mw/Mn) of the weight average molecular weight to the number average molecular weight in terms of polystyrene content as determined above was defined as a degree of dispersion.

[Preparation of Dispersion 1]

23.1 parts of a compound represented by formula (A-I-1), 28.8 parts of a dispersant (manufactured by BYK-Chemie, BYKLPN-6919; 60% propylene glycol monomethyl ether acetate solution), 5.8 parts of a resin (B-1) (in terms of solid content), 28.9 parts of 4-hydroxy-4-methyl-2-pentanone and 202 parts of propylene glycol monomethyl ether acetate were mixed. To the mixture, 600 parts of 0.4-μm zirconia beads were added, followed by shaking for 1 hour using a paint conditioner (manufactured by LAU Corporation). Then, the zirconia beads were removed by filtration to produce a dispersion 1.

[Preparation of Pigment Dispersion (A-1)]

A pigment dispersion (A-1) containing C.I. Pigment blue 15 (α-type) was produced by mixing 12.1 parts of C.I. Pigment blue 15 (α-type), 4.2 parts of an acrylic pigment dispersant, and 83.7 parts of propylene glycol monomethyl ether acetate so as to satisfactorily disperse the pigment using a bead mill.

[Preparation of Pigment Dispersion (A-2)]

A pigment dispersion (A-2) containing C.I. Pigment blue 15:3 (β-type) was produced by mixing 12.0 parts of C.I. Pigment blue 15:3 (β-type), 3.6 parts of an acrylic pigment dispersant, and 84.4 parts of propylene glycol monomethyl ether acetate so as to satisfactorily disperse the pigment using a bead mill.

[Preparation of Pigment Dispersion (A-3)]

A pigment dispersion (A-3) containing C.I. Pigment blue 15:6 (ε-type) was produced by mixing 10.0 parts of C.I. Pigment blue 15:6 (ε-type), 3.5 parts of an acrylic pigment dispersant, and 86.5 parts of propylene glycol monomethyl ether acetate so as to satisfactorily disperse the pigment using a bead mill.

Examples 1 to 11 and Comparative Examples 1 to 5

[Preparation of Colored Photosensitive Resin Composition]

Each colored photosensitive resin composition was produced by mixing components shown in Tables 10 and 11.
Resin (B): Resin (B-1) (in terms of solid content)
Polymerizable compound (C-1): dipentaerythritol hexaacrylate (KAYARAD (registered trademark) DPHA; manufactured by Nippon Kayaku Co., Ltd.)
Polymerization initiator (D-1): N-benzoyloxy-1-(4-phenylsulfanylphenyl)octane-1-one-2-imine (Irgacure (registered trademark) OXE-01; manufactured by BASF Corporation; oxime compound)
Solvent (E):
Solvent (E-1): Ethyl lactate
Solvent (E-2): Propylene glycol monomethyl ether acetate
Leveling agent (F-1): polyether-modified silicone oil (in terms of solid content) (Toray silicone SH8400; manufactured by Dow Corning Toray Co., Ltd.)

TABLE 10

| Unit: parts | | Example 1 | Example 2 | Example 3 | Example 4 | Comparative Example 1 |
|---|---|---|---|---|---|---|
| Compound (1) | Dispersion 1 | 267 | 257 | 285 | 331 | |
| Copper phthalocyanine | Pigment dispersion (A-1) | 152 | | 74 | 192 | |
| | Pigment dispersion (A-2) | | 160 | 150 | | |
| | Pigment dispersion (A-3) | | | | | 498 |
| Resin | (B-1) | 72 | 70 | 58 | 60 | 60 |
| Polymerizable compound | (C-1) | 35 | 36 | 32 | 31 | 34 |
| Polymerization initiator | (D-1) | 19 | 19 | 17 | 17 | 18 |
| Solvent | (E-1) | 42 | 41 | 38 | 39 | 35 |
| | (E-2) | 412 | 416 | 345 | 329 | 354 |
| Leveling agent | (F-1) | 1 | 1 | 1 | 1 | 1 |
| Color characteristics | Film thickness (μm) | 2.5 | 2.5 | 2.2 | 2.2 | 2.5 |
| | x | 0.1342 | 0.1342 | 0.1342 | 0.1342 | 0.1342 |
| | y | 0.1092 | 0.1092 | 0.1092 | 0.1092 | 0.1092 |
| | Y | 13.4 | 13.9 | 13.5 | 13.4 | 12.8 |

TABLE 11

| Unit: parts | | Example 5 | Example 6 | Example 7 | Example 8 | Example 9 | Example 10 | Example 11 |
|---|---|---|---|---|---|---|---|---|
| Compound (1) | Dispersion 1 | 301 | 557 | 554 | 143 | 124 | 380 | 360 |
| Copper phthalocyanine | Pigment dispersion (A-1) | | | 43 | | 330 | 207 | |
| | Pigment dispersion (A-2) | 213 | 42 | | 319 | | | 222 |
| | Pigment dispersion (A-3) | | | | | | | |
| Resin | (B-1) | 57 | 56 | 56 | 58 | 63 | 53 | 50 |
| Polymerizable compound | (C-1) | 32 | 30 | 30 | 34 | 33 | 29 | 30 |
| Polymerization initiator | (D-1) | 17 | 16 | 16 | 18 | 18 | 15 | 16 |
| Solvent | (E-1) | 38 | 38 | 38 | 29 | 39 | 37 | 37 |
| | (E-2) | 341 | 260 | 262 | 398 | 392 | 278 | 284 |
| Leveling agent | (F-1) | 1 | 1 | 1 | 1 | 1 | 1 | 1 |
| Color characteristics | Film thickness (μm) | 3.8 | 2.5 | 2.6 | 3.3 | 2.5 | 2.2 | 2.4 |
| | x | 0.1346 | 0.1379 | 0.1379 | 0.1313 | 0.1313 | 0.1343 | 0.1343 |
| | y | 0.0917 | 0.0836 | 0.0836 | 0.1267 | 0.1267 | 0.1047 | 0.1047 |
| | Y | 10.3 | 10.8 | 10.3 | 15.0 | 14.5 | 12.6 | 13.1 |

<Preparation of Colored Coating Film>

Onto a 5-cm square glass substrate (Eagle 2000; manufactured by Corning Corporation), a colored photosensitive resin composition was applied by a spin coat method so that the film thickness after post-baking was set to 2.5 μm, and then prebaked at 100° C. for 3 minutes, to form a coloring composition layer. After cooling, the coloring composition layer was subjected to light irradiation in an exposure amount (basis: 365 nm) of 80 mJ/cm² under an air atmosphere using an exposure device (TME-150RSK; manufactured by Topcon Corporation). Then, post-baking was performed in an oven at 230° C. for 30 minutes, to produce a colored coating film.

<Evaluation of Chromaticity>

The resultant colored coating film was subjected to spectrometry with a color measurement device (OSP-SP-200; manufactured by Olympus Corporation), and a x-y chromaticity coordinate (x, y) and Y in the CIE XYZ color system were measured using a characteristic function for a C light source. The results are shown in Tables 10 and 11.

The invention claimed is:

1. A colored photosensitive resin composition comprising a colorant, a resin, a polymerizable compound, and a polymerization initiator, the colorant comprising a compound represented by formula (1) and α-type copper phthalocyanine pigment, which is selected from the group consisting of C. I. Pigment Blue 15, C. I. Pigment Blue 15:1, and C. I. Pigment Blue 15:2, and/or β-type copper phthalocyanine pigment, which is selected from the group consisting of C. I. Pigment Blue 15:3 and C. I. Pigment Blue 15:4:

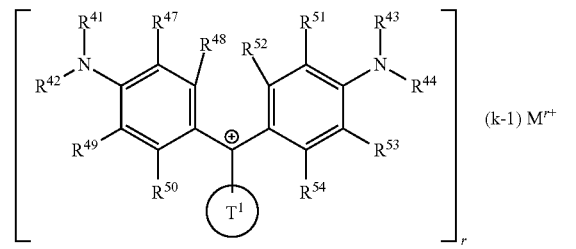

(1)

wherein

R$^{41}$ to R$^{44}$ each independently represent a hydrogen atom, a saturated hydrocarbon group having 1 to 20 carbon atoms, an aromatic hydrocarbon group having 6 to 20 carbon atoms and optionally having a substituent, or an aralkyl group having 7 to 30 carbon atoms and optionally having a substituent; the substituent which is optionally contained in the aromatic hydrocarbon group and the aralkyl group may be —SO$_3$$^-$ or —SO$_2$—N$^-$—SO$_2$—R$^f$; a hydrogen atom contained in the saturated hydrocarbon group is optionally replaced with a substituted or unsubstituted amino group or a halogen atom; when the number of carbon atoms of the saturated hydrocarbon group is 2 to 20, —CH$_2$— contained in the saturated hydrocarbon group is optionally replaced with at least one of —O— and —CO—, provide that in the saturated hydrocarbon group having 2 to 20 carbon atoms, —CH$_2$— and —CH$_2$— adjacent to each other are not simultaneously replaced with —O—, and terminal —CH$_2$— is not replaced with —O— or —CO—; R$^{41}$ and R$^{42}$ are optionally bonded to each other to form a ring together with a nitrogen atom to which they are attached; R$^{43}$ and R$^{44}$ are optionally bonded to each other to form a ring together with a nitrogen atom to which they are attached;

R$^{47}$ to R$^{54}$ each independently represent a hydrogen atom, a halogen atom, a nitro group, a hydroxy group, —SO$_3$$^-$, —SO$_2$—N$^-$—SO$_2$-R$^f$, or a saturated hydrocarbon group having 1 to 20 carbon atoms; —CH$_2$— constituting the saturated hydrocarbon group is optionally replaced with at least one of —O— and —CO—; R$^{48}$ and R$^{52}$ are optionally bonded to each other to form —NH—, —S—, or —SO$_2$—, provide that in the saturated hydrocarbon group, —CH$_2$— and —CH$_2$— adjacent to each other are not simultaneously replaced with —O—, and terminal —CH$_2$— is not replaced with —O— or —CO—;

a ring T$^1$ represents an aromatic heterocycle having 3 to 10 carbon atoms; the aromatic heterocycle optionally has a saturated hydrocarbon group having 1 to 20 carbon atoms, a substituted or unsubstituted amino group, or an aromatic hydrocarbon group having 6 to 20 carbon atoms and optionally having a substituent; the substituent which is optionally contained in the aromatic hydrocarbon group may be —SO$_3$$^-$ or —SO$_2$—N$^-$—SO$_2$-R$^f$;

M$^{r+}$ represents an r-valent metal ion;

k represents the sum of the number of —SO$_3$$^-$ and the number of —SO$_2$—N$^-$—SO$_2$-R$^f$ in the compound represented by formula (1);

r represents an integer of 1 or more;

R$^f$ represents a fluoroalkyl group having 1 to 12 carbon atoms; and the compound represented by formula (1) has at least one —SO$_3$$^-$ or —SO$_2$—N$^-$—SO$_2$-R$^f$.

2. The colored photosensitive resin composition according to claim 1, wherein a content rate of the copper phthalocyanine pigment is 10% by mass or more and 80% by mass or less in 100% by mass of the colorant.

3. A color filter formed from the colored photosensitive resin composition according to claim 1.

4. A display device comprising the color filter according to claim 3.

5. A color filter formed from the colored photosensitive resin composition according to claim 2.

\* \* \* \* \*